(12) United States Patent
Heinz et al.

(10) Patent No.: US 8,933,300 B2
(45) Date of Patent: Jan. 13, 2015

(54) ELONGASE GENE, AND PROCESS FOR THE PREPARATION OF POLYUNSATURATED FATTY ACIDS

(75) Inventors: Ernst Heinz, Hamburg (DE); Thorsten Zank, Hamburg (DE); Ulrich Zähringer, Borstel (DE); Jens Lerchl, Ladenburg (DE); Andreas Renz, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1858 days.

(21) Appl. No.: 11/682,269

(22) Filed: Mar. 5, 2007

(65) Prior Publication Data

US 2008/0160054 A1    Jul. 3, 2008

Related U.S. Application Data

(62) Division of application No. 10/182,634, filed as application No. PCT/EP01/01346 on Feb. 8, 2001, now Pat. No. 7,544,859.

(30) Foreign Application Priority Data

| Feb. 9, 2000 | (DE) | 100 05 973 |
| May 17, 2000 | (DE) | 100 23 893 |
| Dec. 19, 2000 | (DE) | 100 63 387 |

(51) Int. Cl.
| *C12N 15/82* | (2006.01) |
| *A01H 5/00* | (2006.01) |
| *C12N 1/20* | (2006.01) |
| *C07H 21/04* | (2006.01) |
| *C12N 9/10* | (2006.01) |
| *C12P 7/64* | (2006.01) |

(52) U.S. Cl.
CPC .......... *C12N 9/1029* (2013.01); *C12N 15/8247* (2013.01); *C12P 7/6427* (2013.01); *C12P 7/6472* (2013.01)
USPC ........ 800/281; 800/298; 435/252.3; 536/23.2

(58) Field of Classification Search
None
See application file for complete search history.

(56) References Cited

U.S. PATENT DOCUMENTS

| 4,873,316 A | 10/1989 | Meade |
| 4,987,071 A | 1/1991 | Cech |
| 5,116,742 A | 5/1992 | Cech |
| 5,169,770 A | 12/1992 | Chee |
| 5,187,267 A | 2/1993 | Comai |
| 5,376,543 A | 12/1994 | Chee |
| 5,504,200 A | 4/1996 | Hall |
| 5,608,152 A | 3/1997 | Kridl |

FOREIGN PATENT DOCUMENTS

| EP | 249 676 | 12/1987 |
| EP | 264 166 | 4/1988 |
| EP | 397 667 | 6/1989 |
| EP | 335 528 | 10/1989 |
| EP | 375 091 | 6/1990 |
| EP | 388 186 | 9/1990 |
| EP | 424 047 | 4/1991 |
| EP | A 0 264 166 | 8/1996 |
| WO | 84/02913 | 8/1984 |
| WO | 91/13980 | 9/1991 |
| WO | 93/21334 | 10/1993 |
| WO | 95/15387 | 6/1995 |
| WO | 95/15389 | 6/1995 |
| WO | 95/16783 | 6/1995 |
| WO | 95/18222 | 7/1995 |
| WO | 95/19443 | 7/1995 |
| WO | 95/23230 | 8/1995 |
| WO | 95/23290 | 8/1995 |
| WO | 96/12814 | 5/1996 |
| WO | 96/13582 | 5/1996 |
| WO | 97/06250 | 2/1997 |
| WO | 97/20078 | 6/1997 |
| WO | 98/01572 | 1/1998 |
| WO | 98/13487 | 4/1998 |

(Continued)

OTHER PUBLICATIONS

Doerks et al, TIG 14(6): 248-250, Jun. 1998.*

(Continued)

*Primary Examiner* — Elizabeth McElwain
(74) *Attorney, Agent, or Firm* — Novak Druce Connolly Bove + Quigg LLP

(57) ABSTRACT

The invention relates to novel elongase genes with the sequences stated in sequence SEQ ID NO:1, SEQ ID NO: 3, SEQ ID NO: 5 and SEQ ID NO: 7 or their homologs, derivatives or analogs, to a gene construct comprising this gene or its homologs, derivatives and analogs, and to its use. The invention also relates to vectors or transgenic organisms comprising an elongase gene with the sequence SEQ ID NO:1, SEQ ID NO: 3, SEQ ID NO: 5 and SEQ ID NO: 7 or its homologs, derivatives and analogs. The invention furthermore relates to the use of the elongase gene sequences alone or in combination with further elongases and/or further fatty acid biosynthesis genes. The present invention relates to a novel elongase gene with the sequence SEQ ID NO:1 or its homologs, derivatives and analogs. Furthermore, the invention relates to a process for the preparation of polyunsaturated fatty acids and to a process for introducing DNA into organisms which produce large amounts of oils and, in particular, oils with a high content of unsaturated fatty acids. Moreover, the invention relates to an oil and/or a fatty acid preparation with a higher content of polyunsaturated fatty acids with at least two double bonds and/or a triacylglycerol preparation with a higher content of polyunsaturated fatty acids with at least two double bonds.

19 Claims, 16 Drawing Sheets

(56) References Cited

FOREIGN PATENT DOCUMENTS

| | | |
|---|---|---|
| WO | 98/45461 | 10/1998 |
| WO | 98/46763 | 10/1998 |
| WO | 98/46764 | 10/1998 |
| WO | 98/46765 | 10/1998 |
| WO | 98/46776 | 10/1998 |
| WO | 98/54954 | 12/1998 |
| WO | 99/16890 | 4/1999 |
| WO | 99/46394 | 9/1999 |
| WO | 99/64616 | 12/1999 |
| WO | 00/12720 | 3/2000 |
| WO | 00/23604 | 4/2000 |

OTHER PUBLICATIONS

Brenner, S.E., TIG 15(4): 132-133, Apr. 1999.*
Bork et al, TIG 12(10): 425-427, Oct. 1996.*
van de Loo et al, PNAS, USA 92:6743-6747, Jul. 1995.*
Broun et al, Science 282:1315-1317, Nov. 13, 1998.*
Gutcho et al., Chemicals by Fermentation, Park Ridge, N.J., Noyes Data Corp., 1973.
Gruber et al., in Methods in plant molecular biology and biotechnology / edited by Bernard R. Glick, John E. Thompson. Boca Raton : CRC Press, 1993.
Christie et al., Advances in Lipid Methodology 2—The Oily Press, Dundee, Scotland (1993).
Falciatore et al., Marine Biotechnology 1 (3), 1999: 239-251.
Dunahay et al., Genetic Transformationa of Diatoms, J. Phycol., 31, 1995: 1004-1012.
Plant Molecular Biology and Biotechnology (CRC Press, Boca Raton, Florida), Chapter 6/7, p. 71-119 (1993).
White, F.F., Vectors for Gene Transfer in Higher Plats; in Transgenic Plants, vol. 1, Engineering and Utilization, Eds.: Kung and R. Wu, Academic Press, 1993, 15-36.
Jenes, B. et al., Techniques for Gene Transfer, in: Transgenic Plants, vol. 1, Engineering and Utilization, Eds.: Kung and R. Wu, Academic Press, 1993, 128-143.
Potrykus, Annu. Rev. Plant Physiol. Plant Malec. Biol. 42 (1991), 205-225.
Kuninaka, A. Nucleotides and related compounds, p. 561-612, in Biotechnology, vol. 6 (1996), Eds.: Rehm et al., VCH: Weinheim.
Ullmann's Encyclopedia of Industrial Chemistry, vol. A27, Vitamins, p. 443-613 (1996), VCH: Weinheim.
Ong, A.S., Niki E. Packer L., (1995), Nutrition, Lipids, Health and Disease Proceedings of the UNESCO/Confederation of Scientific and Technological Associations in Malaysia and the Society for Free Radical Research—Asia, held on Sep. 1-3, 1994 in Penang, Malaysia, AOCS Press, Champaign, IL X, 374 X.
Gutcho et al., (1983), in Chemicals by Fermentation, Noyes Data Coropration, ISBN: 0818805086.
Bamberg et al., Q. Rev. Biophys., vol. 26, 1993: 1-25.
Gennis, R.B., (1989) Pores, Channels and Transporters, in: Biomembranes, Molecular Structure and Function, Springer Heidelberg, p. 270-322.
Nikaido, H. and Saler, H. (1992) Transport proteins in bacteria: common themes in their design, Science 258: 936-942.
Neidhardt, F.C. et al., (1996) *E. coli* and *Salmonella*, ASM Press: Washington, D.C., p. 612-636.
Lengeler et al., (Eds.;) (1999) Biology of Procaryotes, Thieme: Stuttgart, New York.
Magnuson, K. et al., (1993) Microbiological Reviews, 57: 522-542.
Kinney, 1997, Genetic Engineering, Eds.: J.K. Setlow, 19: 149-166.
Ohlrogge and Browse, 1995, Plant Cell 7: 957-970.
Shanklin and Cahoon, 1998, Annu. Rev. Plant Physiol. Plant Mol. Biol., 49: 611-641.
Voelker, 1996, Genetic Engineering, Eds.: J.K. Seltow, 18: 111-113.
Gerhardt, 1992, Prog. Lipid R. 31: 397-417.
Gühnemann-Schaefer & Kindl, 1995, Prog. Lipid Res., 34: 267-342.
Stymne et al., 1993, in: Biochemistry and Molecular Biology of Membrane and Storage Lipids of Plants, Eds.: Murata and Somerville, Rockville, American Society of Plant Physiologists, 150-158.
Murphy & Ross, 1998, Plant Journal., 13 (1): 1-16.
Michal, G. (1999), Biochemical Pathways: An Atlas of Biochemistry and Molecular Biology, John Wiley & Sons.
Simopoulos, 1999, Am. J. Clin. Nutr. 70 (3. Suppl.): 560-569.
Takahata et al., Biosc. Biotechnol. Biochem., 1998, 62 (11): 2079-2085.
Willich and Winther, 1995, Deutsche Medizinische Wochenschrift 120 (7): 229 ff.
Chapman, 1998, Trends in Plant Science, 3 (11): 419-426.
Wang et al., Plant Physiology, 120, 1999: 645-651.
Sambrook et al., Molecular Cloning: A Laboratory Manual, Cold Spring Harbor Laboratory, Cold Spring Harbor, NY, 1989.
Chirgwin et al., Biochemistry 18, 1979: 5294-5299.
Hames and Higgins (Eds.), 1985, Nucleic Acids Hybridization: A Practical Approach, IRL Press at Oxford University Press, Oxford.
Brown (Ed.), 1991, Essential Molecular Biology: A Practical Approach, IRL Press at Oxford University Press, Oxford.
Gaultier et at, Nucleic Acids Res., 15, 1987: 6625-6641.
Inoue et al., Nucleic Acids Res., 15, 1987: 6131-6148.
Inoue et al., FEBS Lett., 215, 1987: 327-330.
Haselhoff and Gerlach, Nature, 334, 1998: 585-591.
Bartel et al., Science, 261, 1993: 1411-1418.
Helene, C. (1991) Anticancer Drug Res., 6 (6), 569-584.
Helene et al., (1992) Ann. N.Y. Acad. Sci , 660: 27-36.
Maher, L.J. (1992) Bioassays 14 (12): 807-815.
Franck et al., Cell, 21, 1980: 285-294.
Ward et al., Plant. Mol. Biol., 22, 1993: 361-366.
Gatz et al., Plant J., 2, 1992: 397-404.
Stockhaus et al., EMBO J., 8, 1989: 2445-2450.
Baeumlein et al., Plant J., 2, 2, 1992: 233-239.
Goeddel et al.., Gene Expression Technology: Methods in Enzymology 185, Academic Press, San Diego, CA 1990.
Grubber and Crosby, 1993, in: Methods in Plant Molecular Biology and Biotechnology, CRC Press, Boca Raton, Florida, Eds.: Glick and Thompson, Chapter 7, 89-108.
Ramanos et al., Yeast, 8, 1992: 432-488.
Van Den Hondel et al., 1991, Heterologous gene expression in filamentous fungi, in: More et al., "Gene Manipulations in Fungi", in J.W. Bennet & L.L. Lasure, Eds., p. 396-428, Academic Press: San Diego.
Van Den Hondel et al., "Gene transfer systems and vector development for filamentous fungi", 1991 in: Applied Molecular Genetics of Fungi, Peberdy, J.F. et al., Eds., p. 1-28, Cambridge University Press: Cambridge.
Schmidt, R. and Willmitzer L., Plant Cell Rep., 1998: 583-586.
Amann et al.., 1998, Gene 69: 301-315.
Studier et al., Gene Expression Technology: Methods in Enzymology 185, Academic Press, San Diego, California 1990, 60-89; Stratagene, Amsterdam, Netherlands.
Wada et al., Nucleic Acid. Res., 20, 1992: 2111-2118.
Baldari et al., Embo J. 6, 1987: 229-234.
Kurjan and Herskowitz, Cell, 30, 1982: 933-943.
Schultz et al., Gene, 54, 1987: 113-123.
Smith et al., Mol. Cell Biol., 3, 1983: 2156-2165.
Pouwels, P.H. et al., Cloning Vectors, Elsevier, Amsterdam-New York-Oxford, 1985, ISBN 0 444 904018.
Seed, B. Nature, 1987, 329: 840.
Kaufman et al., 1987, 329:840.
Pinkert et al., Genes Dev., 1, 1987: 268-277.
Calame and Eaton, Adv. Immunol., 43, 1988: 235-275.
Winoto and Baltimore, EMBO J., 8, 1989: 729-733.
Banerji et al., Cell, 33, 1983: 729-740.
Queen and Baltimore, Cell, 33, 1983: 741-748.
Byrne and Ruddle, PNAS, 86, 1989: 5473-5477.
Edlund et al., Science, 230, 1985: 912-916.
Kessel and Gruss, Science, 249, 1990: 374-379.
Campes and Tilghman, Genes De., 3, 1989: 537-546.
Falciatore et al., Marine Biotechnology 1 (3), 1999:. 239-251.
Becker et al., Plant Mol. Biol., 20, 1992: 1195-1197.

(56) References Cited

OTHER PUBLICATIONS

Bevan, M.W., Nucl. Acids Res., 12, 1984: 8711-8721.
Gielen et al., EMBO J. 3, 1984: 835 ff.
Gallie et al., Nucl. Acid Res., 15, 1987: 8693-8711.
Benfey et al., EMBO J., 8 1989: 2195-2202.
Kermode, Crit. Rev. Plant Sci., 15, 4, 1996: 285-423.
Gatz et al., Plant J. 2, 1992: 397-404.
Baeumlein et al., Mol. Gen. Genet., 225 (3), 1991: 459-467.
Weintraub et al., Reviews—Trends in Genetics, Bd. 1 (1), 1986.
Cole-Strauss et al., Nucl. Acid. Res., 27 (5), 1999: 1323-1330.
Kmiec, Gene Therapy, 1999, American Scientist, 87 (3): 240-247.
Capecchl, Cell, 51, 1987: 503.
Strepp et al., Proc. Natl. Acad. Sci. USA, 95 (8), 1998: 4368-4373.
Narang, S.A., Tetrahedron, 39, 1983: 3.
Itakura et al., Science, 198, 1984: 1056.
Ike et al., Nucleic Acids Res., 11., 1983: 477.
Arkin and Yourvan, Proc. Natl. Acad. Sci. USA, 89, 1992: 7811-7815.
Delgrave et al., Protein Engineering, 6 (3), 1993: 327-331.
Eroshin et al., Mikrobiologiya, vol. 65, No. 1, 1996: 31-36.
Köhler and Milstein, Nature, 256, 1975: 485.
Galfrö, Meth. Enzymol., 73, 1981.
Alberts, Molecular Biology of the Cell, $3^{rd}$ Edition (1994), e.g. Chapter 17.
Milner, Nature Medicin 1, 1995: 879-880.
Hupp, Cell, 83, 1995: 237-245.
Gibbs, Cell, 79, 1994: 193-198.
Groves, J.T., Curr, Opin. Chem. Biol., 3 (2), 1999: 226-235.
Kaiser, Michaelis and Mitchell, Methods in Yeast Genetics, Cold Spring Harbor Laboratory Press, 1994, ISN 0-87969-451-3.
El-Sheekh, Biologia Plantarum, 42, 1999: 209-216.
Apt et al., Molecular and General Genetics, 252 (5), 1996: 872-879.
Guillard, R.R.L., 1975, "Culture of phytoplankton for feeding marine invertebrates", in: Smith, W.L. and Chanley, M.H. (Eds.) Culture of marine Invertebrate Animals, NY Plenum Press, pp. 29-60.
Von Engel, Am. J. Bot., 55, 1968: 438-446.
Logemann et al., Anal. Biochem., 163, 1987: 21.
Reski et al., Mol. Gen. Genet., 224, 1994: 352-359.
Altschul et al., Nucl. Acid. Res., 25, 1997: 3389-3402.
Henikoff & Henikoff, Proc. Natl. Acad. Sci. USA, 89, 1992: 10915-10919.
Toke & Martin, J. Biol. Chem., 271, 1996: 18413-18422.
Koncz and Schell, Mol. Gen. Genet., 204, 1986: 383-396.
Deblaere et al., Nucl. Acid. Res., 13, 1984: 4777-4788.
Gelvin et al., Plant Molecular Biology Manual, Second Edition, Dordrecht Kluwer Academic Publ., 1995, in Sect., Ringbuch Zentrale Signatur: BT11, ISBN 0-7923-2731-4.
Glick et al., Methods in Plant Molecular Biology and Biotechnology, Boca Raton: CRC Press, 1993, ISBN 0-8493-5164-2.
Moloney et al., Plant Cell Report, 8, 1989: 238-242.
De Block et al., Plant Physiol, 91, 1989: 694-701.
Mlynarova et al., Plant Cell Report, 13, 1994: 282-285.
Freeling and Walbot, The maize handbook, 1993: ISBN 3-540-97826-7, Springer Verlag New York.
Höfgen and Willmitzer, Plant Science, 66, 1990: 221-230.
Rupp, W.D. (1996), DNA repair mechanisms, in: *Escherichia coli* and *Salmonella*, p. 2277-2294, Eds.: Neidhardt et al., ASM Press, Washington, DC.
Greener et al., Strategies, 7, 1994: 32-34.
Ausubel et al., (Eds.), 1985, Current Protocols in Molecular Biology, John Wiley & Sons, New York.
Bormann et al., Mol. Microbiol., 6, 1992: 317-326.
Amasino, Anal. Biochem., 152, 1986: 304.
Ullman, Encyclopedia of Industrial Chemistry, Bd. A2, S. 89-90 mid S. 443-613, VCH: Wienheim (1985).
Fallon, A., et al., (1987) "Applications of HPLC in Biochemistry" in: Laboratory Techniques in Biochemistry and Molecular Biology, Bd. 17.
Rehm et al. (1993) Biotechnology, Bd. 3, Chapter III: "Product recovery and purification", S. 469-714, VCH: Weinheim.
Belter, P.A., et al., (1998) Bioseparations: downstream processing for Biotechnology, John Wiley and Sons.
Kennedy, J.F., und Cabral, J.M.S., (1992) Recovery processes for biological Materials, John Wiley and Sons.
Shaeiwitz, J.A., und Henry J.D. (1988) Biochemical Separations, in: Ullmann's Encyclopedia of Industrial Chemistry, Bd. B3; Chapter 11, S. 1-27, VCH: Weinheim.
Dechow, F.J., (1989) Separation and purification techniques in biotechnology, Noyes Publications.
Cahoon et al., (1999) Proc. Natl. Acad. Sci. USA 96 (22): 12935-12940.
Browse et al., (1986) Analytic Biochemistry 152: 141-145.
Christie, William W., 1993, Advances in Lipid Methodology, Ayr/Schotland: Oily Press (Oily Press Lipid Library; 2).
Christie, William W., Gas Chromatography and Lipids. A Practical Guide—Ayr, Scotland: Oily Press, 1989, Repr. 1992, IX, 307S. (Oily Press Lipid Library; 1); "Progress in Lipid Research", Oxford: Pergamon Press, 1 (1952) 16 (1977) u.d.T.; Progress in the Chemistry of Fats of Other Lipids CODEN.
Kozak, M., (1986) Cell 44, p. 283-292.
Riggs, M.G., & McLachlan, A., (1986) BioTechniques 4, p. 310-313.
Bailey, J.E., & Ollis, D.F., Biochemical Engineering Fundamentals, McGraw-Hill: New York (1986).
Patek et al., (1994) Appl. Environ. Microbiol. 60:133-140.
Malakhova et al., (1996) Bioteknologiya, 11: 27-32.
Schmidt et al., (1998) Bioprocess Engineer, 19: 67-70.
Michal, G., (1999) Biochemical Pathways: An Atlas of Biochemistry and Molecular Biology, John Wiley and Sons.
Fallon, A., et al., (1987) Applications of HPLC in Biochemistry, in: Laboratory Techniques in Biochemistry and Molecular Biology, Bd. 17.
Millar et al., Plant Journal, vol. 12, No. 1, 1997: 121-131.
Database EM_EST Online!, EMBL Heidelberg, AC/ID AW156099, Nov. 9, 1999, Quatrano et al., "ga22h08.y1 Moss EST library PPU Physcomitrella patens cDNA clone", XP002174837.
Zank et al., Biochem. Soc. Transact., vol. 28, No. 6, 2000: 654-658.
Broun et al., Science 282: 1315-1317, Nov. 13, 1998.
Van De Loo et al., PNAS, USA 92: 6743-6747, Jul. 1995.
Doerks et al., TIG 14 (6): 248-250, Jun. 1998.
Smith et al., Nature Biotechnology 15: 1222-1223, Nov. 15, 1997.
Brenner, SE, TIG 15 (4): 132-133, Apr. 1999.
Bork et al., TIG 12 (10): 425-427, Oct. 1996.

* cited by examiner

Fig. 1   Alignment of the yeast elo1 peptide (upper row) with
         Physcomitrella patens PpPSE1

```
 49 dfeftvgkqplseprpvllfiamyyvvifggrslvk.......sckplkl  91
    |  ||  . ||:.|  :..|  ::  ||   :|     . .| |
 32 DTPTTKGLPLVDSPTPIVLGVSVYLTIVIGGLLWIKARDLKPRASEPFLL  81

92 rfisqvhnlmltsvsflwlilmveqmlpivyrhglyfavcnveswtqpme 141
    . :  ||||   ..|   :  .  |   |:|: |:    |  . .  |
 82 QALVLVHNLFCFALSLYMCVGIAYQ..AITWRYSLWGNAYNPKH..KEMA 127

142 tlyylnymtkfvefadtvlmvlkh..rkltflhtyhhgatallcy...nq 186
    | || ||.|:||| |||:|:||    |.:.||| |||  .|: :   .
128 ILVYLFYMSKYVEFMDTVIMILKRSTRQISFLHVYHHSSISLIWWAIAHH 177

187 lvgytavtwvpvtlnlavhvlmywyyflsa........sgirvwwkawvt 228
    |   |   |    ||  ||||||  ||||.|          ..|  :.|
178 APGGEAY.W.SAALNSGVHVLMYAYYFLAACLRSSPKLKNKYLFWGRYLT 225

229 rlqivqfmldlivvyyvlyqkivaayfknactpqcedclgsmtaiaagaa 278
    . |.  ||||.|:  ||  :   |   ||           ||       |
226 QFQMFQFMLNLVQAYYDM..KTNAPY......PQ........WLIKILFY 259

279 iltsylflfisfyievykrgsasgkkk 305
    :  |  ||||  .||::  | :    ||.|
260 YMISLLFLFGNFYVQKYIKPS.DGKQK
```

| identical amino acid
./: chemically equivalent

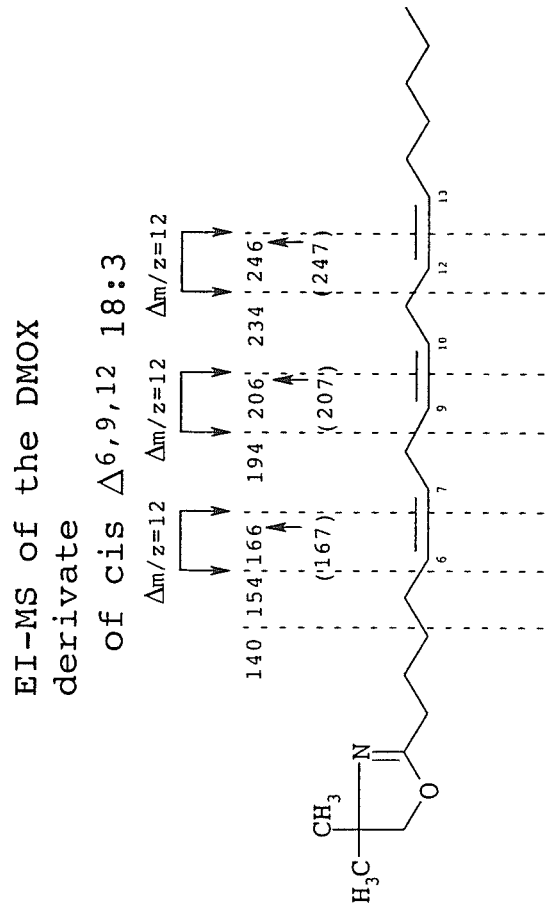
Fig. 3a: DMOX derivative of cis $\Delta^{6,9,12}$ 18:3

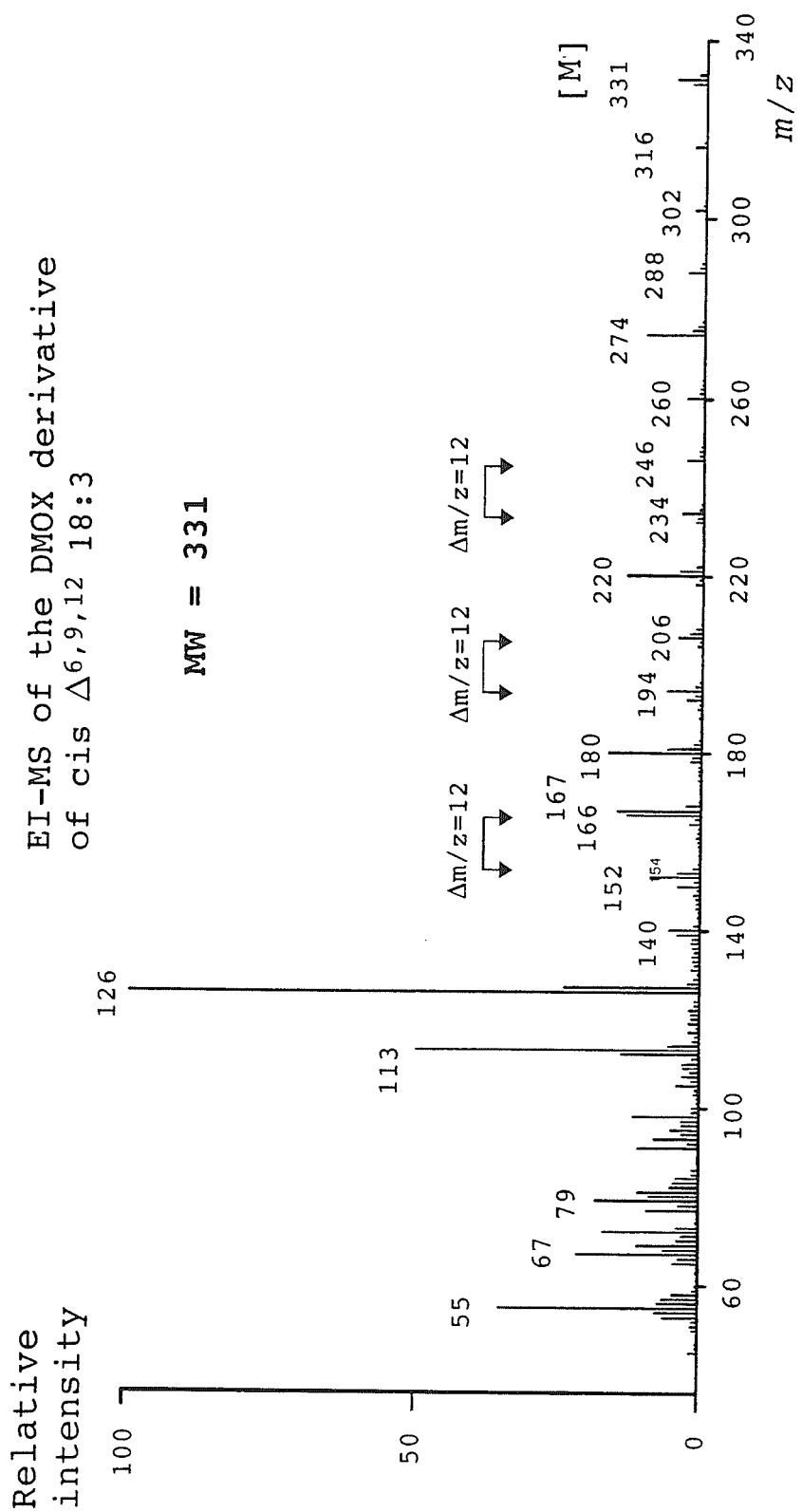
Fig. 3b: Mass spectrum of the DMOX derivative of cis $\Delta^{6,9,12}$ 18:3

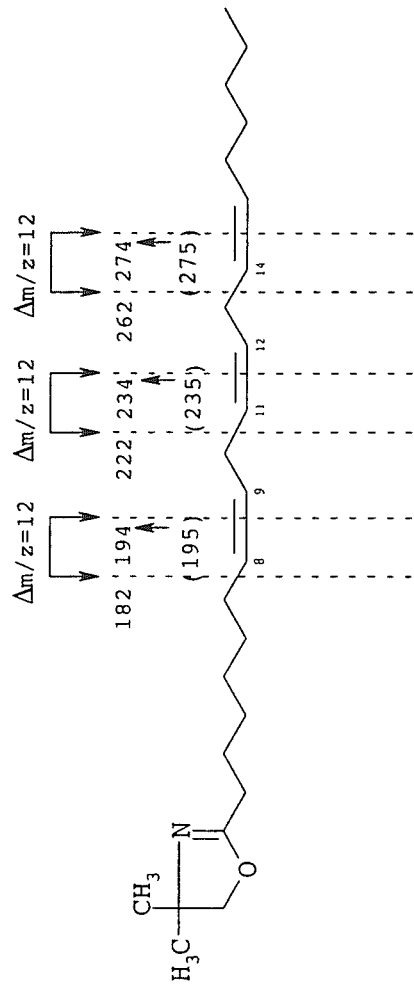
Fig. 4a: DMOX derivative of cis Δ8,11,14 20:3

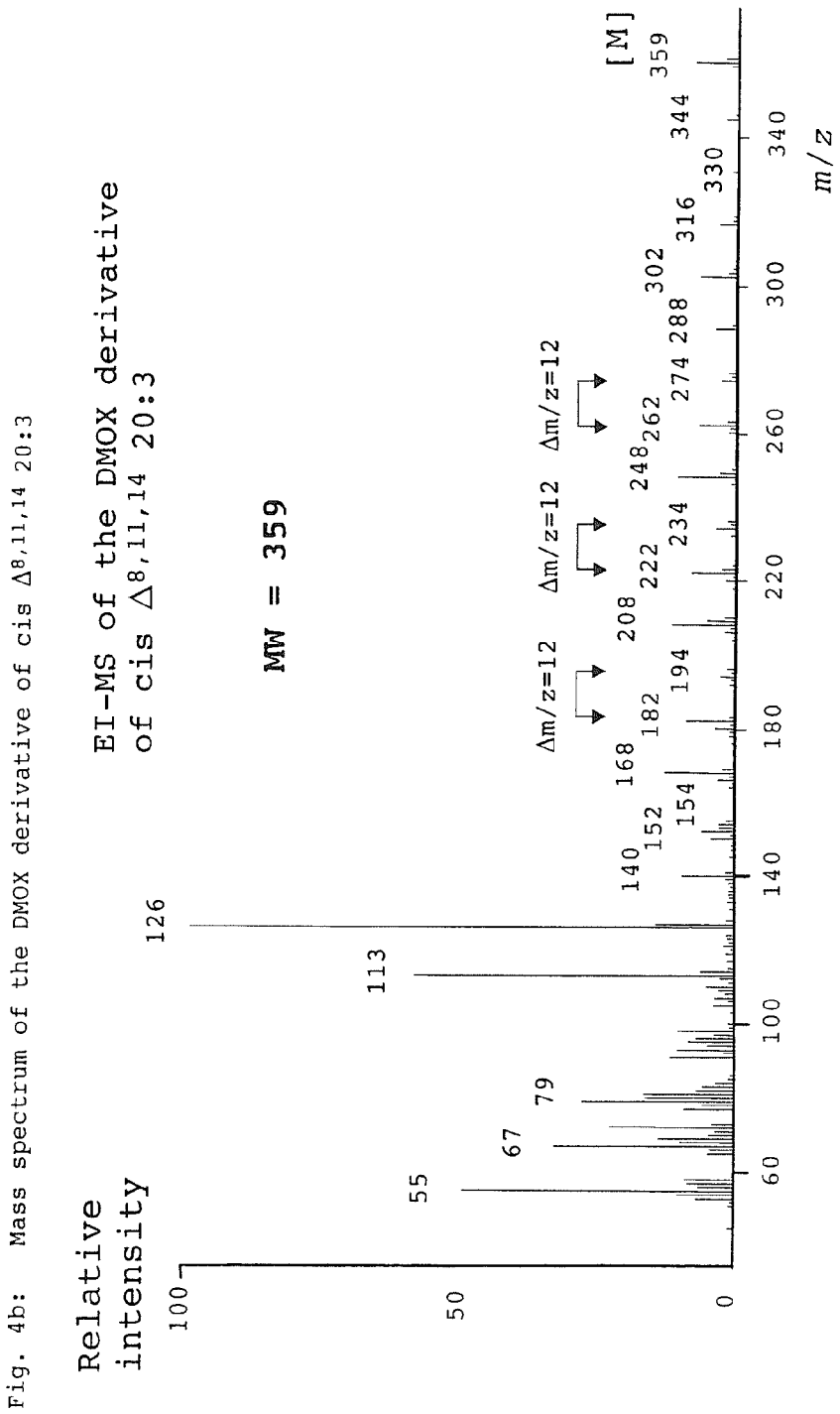
Fig. 4b: Mass spectrum of the DMOX derivative of cis $\Delta^{8,11,14}$ 20:3

Fig. 5:

```
Pp_PSE1: KHKEMAILVLYLFYMSKYVEFMDTVIMILKRSTRQISFLHVYHHSSISLIWWAIAHHAPGG
         KH   ++  LF +SK  E+ DTV++I+K +  ++ FLHV HH++     W    H
Tc_PSE1: KHPHFQLISLLFALSKIWEWFDTVLLIVKGN--KLRFLHVLHHATT--FWLYAIDHIFLS

Pp_PSE1: EAYWSAALNSGVHVLMYAYYFLAACLRSSPKLKNKYLFWGRYLTQFQMFQFMLNL-----
         +  A+N+ +H +MYA+YF        R  PK    +      TQ Q+ QF+ ++
Tc_PSE1: SIKYGVAVNAFIHTVMYAHYF-----RPFPKGLRPLI------TQLQIVQFIFSIGIHTA

Pp_PSE1: VQAYYDMKTNAPYPQWLIKILFYYMISLLFLFGNFYVQKYI
         +  +YD +     W    + +++   L LF NFY+Q+Y+
Tc_PSE1: IYWHYDCEPLVHTHFWEYVTPYLFVVPFLILFLNFYLQQYV
```

Fig. 6:

Pp_PSE1: LNSGVHVLMYAYYFLAA

+N+VH +MYAYY A

Tc_PSE2: INASVHAIMYAYYAFTA

Fig. 7:

Pp_PSE1: AILVYLFYMSKYVEFMDTVIMILKRSTRQISFLHVYHHSSISLIWW-AIA-HHAPGGEAY
         A+ + LF  SK  E MDTV +ILK    +++ FL  YHH+++ L  W A+A   + PG
Cc_PSE1: ALALCLFCFSKIPELMDTVFLILKG--KKVRFLQWYHHATVMLFCWLALATEYTPG---L

Pp_PSE1: WSAALNSGVHVLMYAYYFL 203
         W AA N  VH +MY Y+FL
Cc_PSE1: WFAATNYFVHSIMYMYFFL 339

Fig. 8   Alignment of the polypeptide sequence PpPSE1 and Tc_PSE2

```
Pp_PSE1:   1 MEVVERFYGELDGKVSQGVNAL.LGSFGVELTDTPTTKGLPLVDSPTPIV  49
               |  |..  | . |.      ||       . |
Tc_PSE2:   1 ..............VISGLDLLPVLSWETMKFDTAEVVSVWLRTHMWVPF  36

50 LGVSVYLTIVIGGLLWIKAR...DL.KPRASEPFLLQALVLVHNLFCFAL  95
             |  :|| :: |    :.. |   || || |.       | . : ..:
          37 LMCFIYLVVIFGIQYYMEDRKEFDLRKPLAA....WSAFLAIFSIGASIR  82

96 SLYMCVGIAYQAITWRYSLWGNAYNP..KHKEMAILVYLFYMSKYVEFMD 143
             .. . . .|:  |  : | |.  |         :    |  || | .|
          83 TVPVLLKMLYEKGT.HHVLCGDTRNDWVIDNPAGVWTMAFIFSKIPELID 131

144 TVIMILKRSTRQISFLHVYHHSSISLI.WWAIAHHAPGGEAYWSAALNSG 192
             |. ..:|::   |.:  || |||  .: |  |  |  |  |   ||:|.
         132 TLFIVLRK..RKLITLHWYHHVTVLLFCWHAWATFALTGIVF..AAINAS 177

193 VHVLMYAYYFLAACLRSSPKLKNKYLFWGRYLTQFQMFQFMLNLVQAY.. 240
             || :|||||   ||   |       |    |:|  |. | ..     :
         178 VHAIMYAYYAFTA.LGYRP...TSYAI...YITLIQIMQMVVGTAVTFYI 220

241 .YDMKTNAPYP.......QW..LIK..............ILFYYMI...S 263
              |||    | |       | |   | |              :|  ..  |
         221 GYDMAFVTPQPFRLDMKLNWDPLSKGENTEPTCKGANSSNAIFGVIMYAS 270

264 LLFLFGNFYVQKYIKPSDGKQKGAKTE. 290
             |:||  |:   |::|        ||
         271 YLYLFCLFFYMAYLRPKKSTPAAKKTN. 297
```

| identical amino acid
./: chemically equivalent

Figure 9: Comparison of the polypeptide sequence CC_PSE1 with Tc_PSE2

```
  6 MTEKRGLQFTICGSTGELVQNLQDGPTALALCLFCFSKIPELMDTVFLIL  55
    | .:|    :|| |     . | |  .   | |||||||.||.|::|
 90 MLYEKGTHHVLCGDTRN..DWVIDNPAGVWTMAFIFSKIPELIDTLFIVL 137

56 KGKKVRFLQWYHHATVMLFCWLALATEYTPGLWFAATNYFVHSIMYMYFF 105
    : :|.  |  |||| ||:||||  | ||    |: ||| |  !|.||| |:
138 RKRKLITLHWYHHVTVLLFCWHAWATFALTGIVFAAINASVHAIMYAYY. 186

106 LMTFKTAAKVVKPIAPLITIIQIAQMVWGLIVN.....GIAITT...F.. 145
       |       | ||:||| ||| | |      .|  |   |
187 ..AFTALGYRPTSYAIYITLIQIMQMVVGTAVTFYIGYDMAFVTPQPFRL 234

146 ............FTTGACQ.IQSVTVYSAIVMYASYFYLFSQLFLEAY  180
                |  |.  |       ::|||||  ||| |   | ||
235 DMKLNWDPLSKGENTEPTCKGANSSNAIFGVIMYASYLYLFCLFFYMAY  283
```

| identical amino acid
./: chemically equivalent

Fig. 10

|         | Motif 1  | Motif 2  | Motif 3  | Motif 4  |
|---------|----------|----------|----------|----------|
| Pp_PSE1 |          | FLHVYHH  | LMYAYYF  | FGNFYVQ  |
| Tc_PSE1 |          | FLHVLHH  | LMYAHYF  | FLNFYLQ  |
| Tc_PSE2 | FSKIPEL  | TLHWYHH  | IMYAYFF  |          |
| Cc_PSE1 | FSKIPEL  | FLQWYHH  | IMYMYFF  |          |

Consensus: FSKIPEL    FLHWYHH    LMYAYYF  FGNFYVQ
Variation:                   T QVL     I   MHF    L    L

ELONGASE GENE, AND PROCESS FOR THE PREPARATION OF POLYUNSATURATED FATTY ACIDS

This is a Divisional application of application Ser. No. 10/182,634 filed on Jul. 31, 2002 (now U.S. Pat. No. 7,544,859), the entire disclosure of which is hereby incorporated by reference, which is a national stage entry of PCT/EP01/01346 filed on Feb. 8, 2001.

FIELD OF THE INVENTION

The invention relates to a novel elongase gene with the sequences stated in sequence SEQ ID NO:1, SEQ ID NO:3, SEQ ID NO:5, SEQ ID NO:7, SEQ ID NO:9 and SEQ ID NO:11 or their homologs, derivatives or analogs, to a gene construct comprising this gene or its homologs, derivatives and analogs, and to its use. The invention also relates to vectors or transgenic organisms comprising an elongase gene with the sequence SEQ ID NO:1, SEQ ID NO:3, SEQ ID NO:5, SEQ ID NO:7, SEQ ID NO:9 and SEQ ID NO:11, or its homologs, derivatives and analogs. The invention furthermore relates to the use of the elongase gene sequences alone or in combination with further elongases and/or further fatty acid biosynthesis genes. The present invention relates to a novel elongase gene with the sequence SEQ ID NO:1 or its homologs, derivatives and analogs.

Furthermore, the invention relates to a process for the preparation of polyunsaturated fatty acids and to a process for introducing DNA into organisms which produce large amounts of oils and, in particular, oils with a high content of unsaturated fatty acids. Moreover, the invention relates to an oil and/or a fatty acid preparation with a higher content of polyunsaturated fatty acids with at least two double bonds and/or a triacylglycerol preparation with a higher content of polyunsaturated fatty acids with at least two double bonds.

BACKGROUND OF THE INVENTION

Certain products and byproducts of naturally occurring metabolic processes in cells can be used for a wide spectrum of industries, including the animal feed industry, food industry, cosmetics industry and pharmaceuticals industry. These molecules, which are joinly referred to as "fine chemicals", also include lipids and fatty acids, amongst which the polyunsaturated fatty acids constitute an example of one class. Polyunsaturated fatty acids (PUFAs) are added, for example, to children's formula to increase its nutritional value. For example, PUFAs have a positive effect on the cholesterol level in the blood of humans and are therefore suitable for protection against heart disease. Fine chemicals and polyunsaturated fatty acids (PUFAs) can be isolated from animal sources, for example fish, or microorganisms. Culturing these microorganisms allows large amounts of one or more of the desired molecules to be produced and isolated.

Microorganisms which are especially suitable for preparing PUFAs are microorganisms such as Thraustochytria or Schizochytria strains, algae such as *Phaeodactylum tricornutum* or *Cryptecodinium* species, Ciliata such as *Stylonychia* or *Colpidium*, fungi such as *Mortierella, Entomophthora* or *Mucor*. A number of mutant strains of the microorganisms in question which produce a series of desirable compounds, including PUFAs, have been developed by strain selection. The selection of strains with an improved production of a certain molecule is, however, a time consuming and difficult procedure. Also disadvantageous is the fact that only specific unsaturated fatty acids, or only a specific fatty acid spectrum, can be produced by a defined microorganism.

As an alternative, fine chemicals can suitably be produced on a large scale via the production of plants which have been developed in such a way that they produce the abovementioned PUFAs. Plants which are particularly well suited to this purpose are oil crops which contain large amounts of lipid compounds, such as oilseed rape, canola, linseed, soya, sunflowers, borage and evening primrose. However, other crops which contain oils or lipids and fatty acids are well suited, as mentioned in the detailed description of the present invention. Conventional plant breeding has led to the development of a series of mutant plants which produce a spectrum of desirable lipids and fatty acids, cofactors and enzymes. However, the selection of novel plant varieties with an improved production of a certain molecule is a time-consuming and difficult procedure or even impossible if the compound does not occur naturally in the plant in question, such as in the case of polyunsaturated $C_{20}$-fatty acids, and $C_{22}$-fatty acids and those with longer carbon chains.

The invention provides novel nucleic acid molecules which are suitable for identifying and isolating elongase genes of PUFA biosynthesis and which can be used for the modification of oils, fatty acids, lipids, lipid-derived compounds and, most preferably, for the preparation of polyunsaturated fatty acids, since there remains a great demand for novel genes which encode enzymes which are involved in the biosynthesis of unsaturated fatty acids and which make it possible for these to be prepared on an industrial scale. In particular, there is a demand for fatty acid biosynthesis enzymes which make possible the elongation of polyunsaturated fatty acids, preferably with two or more double bonds in the molecule. The nucleic acids according to the invention encode enzymes which have this ability.

Microorganisms such as *Phaeodactylum, Colpidium, Mortierella, Entomophthora, Mucor, Crypthecodinium* and other algae and fungi and plants, in particular oil crops, are generally used in industry for the production of a large number of fine chemicals on a large scale.

As long as cloning vectors and techniques are available for the genetic manipulation of the abovementioned microorganisms and Ciliata, as disclosed in WO 98/01572 and WO 00/23604, or algae and related organisms, such as *Phaeodactylum tricornutum*, described in Falciatore et al. [1999, Marine Biotechnology 1(3):239-251]; and Dunahay et al. [1995, Genetic transformation of diatoms, J. Phycol. 31:10004-1012] and the references cited therein, the nucleic acid molecules according to the invention can be used for the recombinant modification of these organisms so that they become better or more efficient producers of one or more fine chemicals, especially unsaturated fatty acids. This improved production or production efficiency of a fine chemical can be caused by a direct effect of manipulating a gene according to the invention or by an indirect effect of this manipulation.

Mosses and algae are the only known plant systems which produce considerable amounts of polyunsaturated fatty acids, such as arachidonic acid (=ARA) and/or eicosapentaenoic acid (=EPA) and/or docosahexaenoic acid (=DHA). Mosses contain PUFAs in membrane lipids, while algae, organisms related to algae and some fungi also accumulate considerable amounts of PUFAs in the triacylglycerol fraction. Thus, nucleic acid molecules which are isolated from such strains which also accumulate PUFAs in the triacylglycerol fractions are particularly suitable for modifying the lipid and PUFA production systems in a host, in particular in microorganisms, such as the abovementioned microorganisms, and plants, such as oil crops, for example oilseed rape, canola, linseed, soya, sunflower, borage, castor-oil plant, oil palm, safflower (*Carthamus tinctorius*), coconut, peanut or cacao bean. Furthermore, nucleic acids from triacylglycerol-accumulating microorganisms can be used for identifying such DNA sequences and enzymes in other species which are suitable for modifying the biosynthesis of PUFA precursor molecules in the organisms in question. Microorganisms which accumulate PUFAs such as ARA, EPA or DHA in triacylglycerols are, in particular, microorganisms such as *Crypthecodinium cohnii* and *Thraustochytrium* species. Thraustochytria are also closely related to the Schizochytria strains in terms of phylogenetics. Even though these organisms are not closely related to mosses such as *Physcomitrella*, sequence similarities at the DNA sequence and, in particular, polypeptide level can be observed to such an extent that DNA molecules can be identified, isolated and characterized functionally in heterologous hybridization experiments, sequence alignments and experiments using the polymerase chain reaction, even from organisms which are distantly related in terms of evolution. In particular, consense sequences can be derived which are suitable for the heterologous screening or the functional complementation and prediction of gene functions in third species. The ability to identify these functions, for example to predict the substrate specificity of enzymes, can therefore be of significant importance. Furthermore, these nucleic acid molecules may act as reference sequences for mapping related genomes or for deriving PCR primers.

The novel nucleic acid molecules encode proteins termed in the present context PUFA-specific elongases (=PSEs, or PSE in the singular). These PSEs can, for example, exert a function which is involved in the metabolism (for example in the biosynthesis or in the breakdown) of compounds required for lipid or fatty acid synthesis, such as PUFAs, or which participate in the transmembrane transport of one or more lipid/fatty acid compositions, either into the cell or out of the cell.

This novel application shows the isolation of such novel elongase genes in greater detail. For the first time, we have isolated elongase genes which are suitable for producing long-chain polyunsaturated fatty acids, preferably having more than eighteen or twenty carbon atoms in the carbon skeleton of the fatty acid and/or at least two double bonds in the carbon chain while being derived from typical organisms which contain high amounts of PUFAs in the triacylglycerol fraction. This means, in the singular, a PSE gene or PSE protein or, in the plural, PSE genes or PSE proteins. Other known patent applications and publications disclose, or show, no functionally active PSE gene, even though various known patent applications exist which show the elongation of saturated fatty acids of short or medium chain length (WO 98/46776 and U.S. Pat. No. 5,475,099) or the elongation or production of long-chain fatty acids, but which then have no more than one double bond or lead to long-chain fatty acid wax esters (see WO 98/54954, WO 96/13582, WO 95/15387). The invention presented here describes the isolation of novel elongases with novel properties. Starting from the sequence stated in SEQ ID NO:1, it was possible to find further nucleic acids which encode elongases which elongate unsaturated fatty acids.

WO 99/64616, WO 98/46763, WO 98/46764 and WO 98/46765 describe the production of PUFAs in transgenic plants and demonstrate the cloning and functional expression of corresponding desaturase activities, in particular from fungi, but demonstrate no PSE-encoding gene and no functional PSE activity. The expression of the desaturase activities leads to a shift in the fatty acid spectrum in the transgenic plants, but no increased content of unsaturated fatty acids was observed. The production of a trienoic acid with $C_{18}$-carbon chain has been demonstrated and claimed with reference to gamma-linolenic acid, but the production of very long-chain polyunsaturated fatty acids (with a $C_{20}$— and longer carbon chain and of trienoic acids and higher unsaturated types) has, however, not been demonstrated to date.

To prepare long-chain PUFAs, the polyunsaturated $C_{16}$- or $C_{18}$-fatty acids must be elongated by at least two carbon atoms by the enzymatic activity of an elongase. The nucleic acid sequence SEQ ID NO:1 according to the invention enclodes the first plant elongase which is capable of elongating the $C_{16}$- or $C_{18}$-fatty acids with at least two double bonds in the fatty acid by at least two carbon atoms. After one elongation cycle, this enzyme activity leads to $C_{20}$-fatty acids, and after two, three and four elongation cycles to $C_{22}$-, $C_{24}$- or $C_{26}$-fatty acids. Longer-chain PUFAs can also be synthesized with the aid of the other elongases which are disclosed (SEQ ID NO:3, SEQ ID NO:5, SEQ ID NO:7, SEQ ID NO:9 and SEQ ID NO:11). They can be employed individually, multiply or, for example, in addition to the PUFA elongase from the moss *Physcomitrella patens* (SEQ ID NO:1) for increasing the PUFA content in a novel process for the preparation of PUFAs. The activity of the elongases according to the invention preferably leads to $C_{20}$-fatty acids with at least two double bonds in the fatty acid molecule, preferably with three or four double bonds, especially preferably three double bonds, in the fatty acid molecule and/or $C_{22}$-fatty acids with at least two double bonds in the fatty acid molecule, preferably with four, five or six double bonds, especially preferably with five or six double bonds, in the molecule. After the elongation by the enzyme according to the invention has taken place, further desaturation steps may be carried out in order to obtain the highly desaturated fatty acids. The products of the elongase activities and of the further desaturation with is a possibility therefore lead to preferred PUFAs with a higher degree of desaturation, such as docosadienoic acid, arachidonic acid, ω6-eicosatrienedihomo-γ-linolenic acid, eicosapentaenoic acid, ω3-eicosatrienoic acid, ω3-eicosatetraenoic acid, docosapentaenoic acid or docosahexaenoic acid. Substrates of the enzyme activity according to the invention are, for example, taxol acid; 7,10,13-hexadecatrienoic acid, 6,9-octadecadienoic acid, linolic acid, linolenic acid, α- or γ-linolenic acid or stearidonic acid, and also arachidonic acid, eicosatetraenoic acid, docosapentaenoic acid, eicosapentaenoic acid. Preferred substrates are linolic acid, γ-linolenic acid and/or α-linolenic acid, and also arachidonic acid, eicosatetraenoic acid, docosapentaenoic acid and eicosapentaenoic acid. Arachidonic acid, docosapentaenoic acid and eicosapentaenoic acid are especially preferred. The $C_{16}$- or $C_{18}$-fatty acids with at least two double bonds in the fatty acid can be elongated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

Of particular importance for human nutrition is conjugated linolic acid "CLA". CLA is to be understood as meaning, in particular, fatty acids such as $C18:2^{9\ cis,\ 11trans}$ or the isomer $C18:2^{10trans,\ 12\ cis}$, which can be desaturated or elongated after uptake in the body owing to human enzyme systems and can contribute to health-promoting effects. Elongases according to the invention also allow those conjugated fatty acids which have at least two double bonds in the molecule to be elongated and thus make available such health-promoting fatty acids for human nutrition. Other examples of conjugated fatty acids are alpha-parinaric acid, eleostearic acid and calendulic acid.

Given cloning vectors for use in plants and in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, Vol. 1, Engineering and Utilization, Ed.: Kung and R. Wu, Academic Press, 1993, 15-38; B. Jenes et al., Techniques for Gene Transfer, in: Transgenic Plants, Vol. 1, Engineering and Utilization, Ed.: Kung and R. Wu, Academic Press (1993), 128-143; Potrykus, Annu. Rev. Plant Physiol. Plant Molec. Biol. 42 (1991), 205-225)), the nucleic acids according to the invention can be used for the recombinant modification of a broad spectrum of plants so that they become a better, more efficient or modified producer of one or more lipid-derived products, such as PUFAs. This improved production or production efficiency of a lipid-derived product, such as PUFAs, can be caused by the direct effect of the manipulation or by an indirect effect of this manipulation.

There exists a series of mechanisms by which the modification of a PSE protein according to the invention can directly affect yield, production and/or production efficiency of a fine chemical from an oil crop or a microorganism, owing to a modified protein. The number or activity of the PSE protein or PSE gene can be increased so that greater quantities of these compounds are produced de novo since the organisms lacked this activity and biosynthesis ability prior to introduction of the gene in question. Also, the use of various, divergent sequences, i.e. sequences which differ at the DNA sequence level, may be advantageous in this context.

The introduction of a PSE gene or a plurality of PSE genes to an organism or a cell can not only increase the biosynthesis flow toward the end product, but also increase, or create de novo, the corresponding triacylglycerol composition. Equally, the number or activity of other genes which are involved in the import of nutrients required for the biosynthesis of one or more fine chemicals (for example fatty acids, polar and neutral lipids) may be increased, so that the concentration of these precursors, cofactors or intermediates is increased within the cells or within the storage compartment, thus further increasing the ability of the cells to produce PUFAs, as described hereinbelow. Fatty acids and lipids themselves are desirable as fine chemicals; optimization of the activity, or increasing the number, of one or more PSEs which are involved in the biosynthesis of these compounds, or destroying the activity of one or more PSEs which are involved in the breakdown of these compounds, can make possible an increase in yield, production and/or production efficiency of fatty acid molecules and lipid molecules from plants or microorgansims.

The mutagenesis of the PSE gene according to the invention may also lead to a PSE protein with modified activities which directly or indirectly affect the production of one or more desired fine chemicals. For example, the number or activity of the PSE gene according to the invention can be increased, so that the normal metabolic waste products or byproducts of the cell (whose quantity might be increased owing to the overproduction of the desired fine chemical) are exported in an efficient manner before they destroy other molecules or processes within the cell (which would reduce cell viability) or would interfere with the biosynthetic pathways of the fine chemical (thus reducing yield, production or production efficiency of the desired fine chemical). Furthermore, the relatively large intracellular quantities of the desired fine chemical themselves may be toxic to the cell or may interfere with enzyme feedback mechanisms, such as allosteric regulation; for example, they might increase the allocation of the PUFA into the triacylglycerol fraction owing to an increased activity or number of other enzymes or detoxifying enzymes of the PUFA pathway which follow downstream; the viability of the seed cells might increase which, in turn, leads to better development of cells in culture or to seeds which produce the desired fine chemical. Alternatively, the PSE gene according to the invention can be manipulated in such a way that the corresponding quantities of the various lipid molecules and fatty acid molecules are produced. This can have a decisive effect on the lipid composition of the cell membrane and generates novel oils in addition to the occurrence of PUFAs which have been synthesized de novo. Since each type of lipid has different physical properties, a change in the lipid composition of a membrane can substantially modify membrane fluidity. Changes in membrane fluidity can have an effect on the transport of molecules via the membrane and on cell integrity, both of which have a decisive effect on the production of fine chemicals. In plants, moreover, these changes can also have an effect on other traits such as the tolerance to abiotic and biotic stress situations.

Biotic and abiotic stress tolerance is a general trait which it is desirable to impart to a broad spectrum of plants such as maize, wheat, rye, oats, triticale, rice, barley, soybean, peanut, cotton, oilseed rape and canola, cassava, pepper, sunflower and tagetes, Solanaceae plants such as potato, tobacco, aubergine and tomato, *Vicia* species, pea, alfalfa, shrub plants (coffee, cacao, tea), *Salix* species, trees (oil palm, coconut) and perennial grasses and fodder crops. As a further embodiment according to the invention, these crops are also preferred target plants for genetic engineering. Very especially preferred plants according to the invention are oil crops such as soybean, peanut, oilseed rape, canola, sunflower, safflower, trees (oil palm, coconut) or crops such as maize, wheat, rye, oats, triticale, rice, barley, alfalfa, or shrub plants (coffee, cacao, tea).

Accordingly, one aspect of the invention relates to isolated nucleic acid molecules (for example cDNAs), encompassing nucleotide sequences which encode a PSE or several PSEs or biologically active parts thereof, or nucleic acid fragments which are suitable as primers or hybridization probes for the detection or amplification of PSE-encoding nucleic acids (for example DNA or mRNA). In a specially preferred embodiment, the nucleic acid molecule encompasses one of the nucleotide sequences shown in SEQ ID NO:1, SEQ ID NO:3, SEQ ID NO:5, SEQ ID NO:7, SEQ ID NO:9 and SEQ ID NO:11, or the coding region or a complement of one of these nucleotide sequences. In other especially preferred embodiments, the isolated nucleic acid molecule according to the invention encompasses a nucleotide sequence which hybridizes with a nucleotide sequence as shown in the sequence SEQ ID NO:1, SEQ ID NO:3, SEQ ID NO:5, SEQ ID NO:7, SEQ ID NO:9 and SEQ ID NO:11, or a part thereof or which has at least approximately 50%, preferably at least approximately 60%, more preferably at least approximately 70%, 80% or 90% and even more preferably at least approximately 95%, 96%, 97%, 98%, 99% or more homology thereto. In other preferred embodiments, the isolated nucleic acid molecule encodes one of the amino acid sequences shown in the sequence SEQ ID NO:2, SEQ ID NO:4, SEQ ID NO:6, SEQ ID NO:8, SEQ ID NO:10 and SEQ ID NO:12. Preferably, the preferred PSE gene according to the invention also has at least one of the PSE activities described herein.

In a further embodiment, the isolated nucleic acid molecule encodes a protein or part thereof, the protein or the part thereof comprising an amino acid sequence which has sufficiently homology with an amino acid sequence of the sequence SEQ ID NO:2, SEQ ID NO:4, SEQ ID NO:6, SEQ ID NO:8, SEQ ID NO:10 and SEQ ID NO:12, that the protein or the part thereof retains a PSE activity. Preferably, the protein or the part thereof which is encoded by the nucleic acid molecule retains the ability to participate in the metabolism of compounds required for the synthesis of cell membranes of plants or in the transport of molecules via these membranes. In one embodiment, the protein encoded by the nucleic acid molecule has at least approximately 50%, preferably at least approximately 60% and more preferably at least approximately 70%, 80% or 90% and most preferably at least approximately 95%, 96%, 97%, 98%, 99% or more homology with an amino acid sequence of the sequence SEQ ID NO:2, SEQ ID NO:4, SEQ ID NO:6, SEQ ID NO:8, SEQ ID NO:10 and SEQ ID NO:12. In a further preferred embodiment, the protein is a full-length protein, parts of which are essentially homologous to a complete amino acid sequence of SEQ ID NO:2, SEQ ID NO:4, SEQ ID NO:6, SEQ ID NO:8, SEQ ID NO:10 and SEQ ID NO:12, (which is due to the open reading frame shown in SEQ ID NO:1, SEQ ID NO:3, SEQ ID NO:5, SEQ ID NO:7, SEQ ID NO:9 and SEQ ID NO:11) and which can be isolated in its full length by methods and experiments with which the skilled worker is familiar.

In another preferred embodiment, the isolated nucleic acid molecule originates from *Phytophthora infestans, Physcomitrella patens, Crypthecodinium cohnii* or *Thraustochytrium* and encodes a protein (for example a PSE fusion protein) comprising a biologically active domain which has at least approximately 50% or more homology with an amino acid sequence of the sequence SEQ ID NO:2, SEQ ID NO:4, SEQ ID NO:6, SEQ ID NO:8, SEQ ID NO:10 and SEQ ID NO:12 and retains the ability to participate in the metabolism of compounds required for the synthesis of cell membranes of plants or in the transport of molecules via these membranes or which has at least one of the elongation activities resulting in PUFAs such as ARA, EPA or DHA or their precursor molecules or one of the activities listed in Table 1, and also encompasses heterologous nucleic acid sequences which encode a heterologous polypeptide or regulatory proteins.

one nucleotide molecule according to the invention and host cells into which these vectors have been introduced, in particular microorganisms, plant cells, plant tissues, plant organs or intact plants. In one embodiment, such a host cell can store fine chemicals, in particular PUFAs; to isolate the desired compound, the cells are harvested. The compound (oils, lipids, triacylglycerides, fatty acids) or the PSE can then be isolated from the medium or from the host cell which, in the case of plants, are cells comprising or storing the fine chemicals, most preferably cells of storage tissues such as seed coats, tubers, epidermis cells and seed cells.

Yet another aspect of the invention relates to a genetically modified plant, preferably an oil crop as mentioned above, especially preferably a rapeseed, linseed or *Physcomitrella patens* plant into which a PSE gene has been introduced. In one embodiment, the genome of oilseed rape, linseed or *Physcomitrella patens* has been modified by introducing, as transgene, a nucleic acid molecule according to the invention encoding a wild-type or mutated PSE sequence. In another embodiment, an endogenous PSE gene in the genome of the donor organisms *Physcomitrella patens, Phytophthora infestans, Crypthecodinium* or *Thraustochytrium* has been modified, that is to say functionally destroyed, for example by homologous recombination with a modified PSE gene or by mutagenesis and detection by means of DNA sequences. In a preferred embodiment, the plant organism belongs to the genus *Physcomitrella, Ceratodon, Funaria*, oilseed rape or linseed, with *Physcomitrella*, oilseed rape or linseed being preferred. In a preferred embodiment, *Physcomitrella*, oilseed rape or linseed is also used to produce a desired compound such as lipids or fatty acids, with PUFAs being especially preferred.

In yet another preferred embodiment, the moss *Physcomitrella patens* can be used for demonstrating a function of an elongase gene using homologous recombination on the basis of the nucleic acids described in the present invention.

TABLE 1

Fatty acid profile of five transgenic yeast strains in mol %. The proportions of γ-linolenic acid which has been added and taken up are emphasized by numbers printed in bold, those of the elongated products are underlined and those of the elongated γ-linolenic acid are emphasized by numbers printed in bold (last line).

| Fatty acids [mol %] | pYES2 | pY2PSE1a | pY2PSE1b | pY2PSE1c | pY2PSE1d |
|---|---|---|---|---|---|
| 16:0 | 17.0 | 17.6 | 16.4 | 16.3 | 17.6 |
| 16:1$\Delta^9$ | 28.0 | 26.8 | 28.0 | 27.9 | 25.1 |
| 18:0 | 6.5 | 6.0 | 6.4 | 5.6 | 6.1 |
| 18:1$\Delta^9$ | 25.9 | 23.5 | 27.0 | 25.2 | 21.4 |
| 18:3$\Delta^{6,9,12}$ | 22.6 | 15.7 | 13.2 | 16.4 | 22.8 |
| 20:3$\Delta^{8,11,14}$ | — | 10.3 | 9.0 | 8.6 | 7.1 |
| 18:3$\Delta^{6,9,12}$ Elongation | — | 39.6 | 40.5 | 34.4 | 23.7 |

In another embodiment, the isolated nucleic acid molecule is at least 15 nucleotides in length and hybridizes under stringent conditions with a nucleic acid molecule comprising a nucleotide sequence of SEQ ID NO:1, SEQ ID NO:3, SEQ ID NO:5, SEQ ID NO:7, SEQ ID NO:9 and SEQ ID NO:11. The isolated nucleic acid molecule preferably corresponds to a naturally occurring nucleic acid molecule. More preferably, the isolated nucleic acid molecule encodes naturally occurring *Crypthecodinium, Phytophthora* or *Thraustochytrium* PSE or a biologically active part thereof.

A further aspect of the invention relates to vectors, for example recombinant expression vectors, comprising at least Yet another aspect of the invention relates to an isolated PSE gene or a part, for example a biologically active part, thereof. In a preferred embodiment, the isolated PSE or a part thereof can participate in the metabolism of compounds required for the synthesis of cell membranes in a microorganism or a plant cell or in the transport of molecules via its membranes. In a further preferred embodiment, the isolated PSE or the part thereof has sufficient homology with an amino acid sequence of SEQ ID NO:2, SEQ ID NO:4, SEQ ID NO:6, SEQ ID NO:8, SEQ ID NO:10 and SEQ ID NO:12 for this protein or the part thereof to retain the ability to participate in the metabolism of compounds required for the synthesis of cell membranes in microorganisms or plant cells or in the transport of molecules via these membranes.

The invention also provides an isolated preparation of a PSE. In preferred embodiments, the PSE gene encompasses an amino acid sequence of SEQ ID NO:2, SEQ ID NO:4, SEQ ID NO:6, SEQ ID NO:8, SEQ ID NO:10 and SEQ ID NO:12. In a further preferred embodiment, the invention relates to an isolated full-length protein which is essentially homologous with a complete amino acid sequence of SEQ ID NO:2, SEQ ID NO:4, SEQ ID NO:6, SEQ ID NO:8, SEQ ID NO:10 and SEQ ID NO:12 (which are encoded by the open reading frames shown in SEQ ID NO:1, SEQ ID NO:3, SEQ ID NO:5, SEQ ID NO:7, SEQ ID NO and SEQ ID NO:11). In a further embodiment, the protein has at least approximately 50%, preferably at least approximately 60%, more preferably at least approximately 70%, 80% or 90% and most preferably at least approximately 95%, 96%, 97%, 98%, 99% or more homology with an amino acid sequence of sequence SEQ ID NO:2, SEQ ID NO:4, SEQ ID NO:6, SEQ ID NO:8, SEQ ID NO:10 and SEQ ID NO:12. In other embodiments, the isolated PSE encompasses an amino acid sequence which has at least approximately 50% homology with one of the amino acid sequences of SEQ ID NO:2, SEQ ID NO:4, SEQ ID NO:6, SEQ ID NO:8, SEQ ID NO:10 and SEQ ID NO:12 and which can participate in the metabolism of compounds required for the synthesis of fatty acids in a microorganism or a plant cell or in the transport of molecules via these membranes or has one or more of the PUFA-elongating activities, the elongation advantageously concerning desaturated $C_{16}$- or $C_{18}$- or $C_{20}$-carbon chains with double bonds in at least two positions.

As an alternative, the isolated PSE can encompass an amino acid sequence which is encoded by a nucleotide sequence hybridizing with a nucleotide sequence of SEQ ID NO:1, SEQ ID NO:3, SEQ ID NO:5, SEQ ID NO:7, SEQ ID NO:9 and SEQ ID NO:11, for example under stringent conditions, or which has at least approximately 50%, preferably at least approximately 60%, more preferably at least approximately 70%, 80% or 90% and even more preferably at least approximately 95%, 96%, 97%, 98%, 99% or more homology thereto. It is also preferred for the preferred PSE forms also to have one of the PSE activities described herein.

The PSE polypeptide or a biologically active part thereof can be linked functionally to a non-PSE polypeptide to form a fusion protein. In preferred embodiments, this fusion protein has an activity which differs from that of PSE alone. In other preferred embodiments, this fusion protein participates in the metabolism of compounds which are required for the synthesis of lipids and fatty acids, cofactors and enzymes in microorganisms or plants, or in the transport of molecules via these membranes. In especially preferred embodiments, the introduction of this fusion protein into a host cell modulates the production of a desired compound by the cell. In a preferred embodiment, these fusion proteins also contain Δ4-, Δ5- or Δ6-, Δ8-, Δ15-, Δ17- or Δ19-desaturase activities, alone or in combination.

Another aspect of the invention relates to a process for the production of a fine chemical. This process either comprises culturing a suitable microorganism or culturing plant cells, plant tissues, plant organs or intact plants encompassing the nucleotide sequences according to the invention of SEQ ID NO:1, SEQ ID NO:3, SEQ ID NO:5, SEQ ID NO:7, SEQ ID NO:9 and SEQ ID NO:11 or their homologs, derivatives or analogs or a gene construct which compasses SEQ ID NO:1, SEQ ID NO:3, SEQ ID NO:5, SEQ ID NO:7, SEQ ID NO:9 and SEQ ID NO:11 or their homologs, derivatives or analogs, or a vector encompassing these sequences or the gene construct which brings about the expression of a PSE nucleic acid molecule according to the invention so that a fine chemical is produced. In a preferred embodiment, the process furthermore encompasses the step of obtaining a cell comprising such an elongase nucleic acid sequence according to the invention, in which a cell is transformed with an elongase nucleic acid sequence, a gene construct or a vector which bring about the expression of a PSE nucleic acid according to the invention. In a further preferred embodiment, this process furthermore comprises the step of obtaining the fine chemical from the culture. In an especially preferred embodiment, the cell belongs to the order of the Ciliata, to microorganisms such as fungi, or to the plant kingdom, in particular to oil crops, with microorganisms or oil crops being especially preferred.

A further aspect of the invention relates to methods of modulating the production of a molecule by a microorganism. These methods encompass combining the cell with a substance which modulates the PSE activity or the expression of the PSE nucleic acid so that a cell-associated activity is modified relative to the same activity in the absence of the substance. In a preferred embodiment, a metabolic pathway, or two metabolic pathways, of the cell for lipids and fatty acids, cofactors and enzymes is, or are, modulated or the transport of compounds via these membranes is modulated so that the yield or the production rate of a desired fine chemical by this microorganism is improved. The substance which modulates the PSE activity can be a substance which stimulates the PSE activity or the expression of the PSE nucleic acid or which can be used as intermediate in fatty acid biosynthesis. Examples of substances which stimulate the PSE activity or the expression of PSE nucleic acids are, inter alia, small molecules, active PSEs and nucleic acids encoding PSEs which have been introduced into the cell. Examples of substances which inhibit the PSE activity or PSE expression are, inter alia, small molecules and/or antisense PSE nucleic acid molecules.

A further aspect of the invention relates to methods of modulating the yields of a desired compound from a cell, which encompass introducing, into a cell, a wild-type or mutant PSE gene which is either kept on a separate plasmid or integrated into the genome of the host cell. In the case of integration into the genome, integration can be random or take place by recombination in such a way that the native gene is replaced by the copy which is introduced, thus modulating the production of the desired compound by the cell, or by using a gene in trans, so that the gene is functionally linked to a functional expression unit comprising at least one sequence which ensures the expression of a gene and at least one sequence which ensures the polyadenylation of a functionally transcribed gene.

In a preferred embodiment, the yields are modified. In a further embodiment, the desired chemical is increased, it being possible to reduce undesired compounds which have a negative effect. In an especially preferred embodiment, the desired fine chemical is a lipid or fatty acid, a cofactor or an enzyme. In an especially preferred embodiment, this chemical is a polyunsaturated fatty acid. More preferably, it is selected from amongst arachidonic acid (=ARA), eicosapentaenoic acid (=EPA) or docosahexaenoic acid (=DHA).

BRIEF DESCRIPTION OF THE DRAWINGS

Exemplary methods and arrangements conducted and configured according to the advantageous solutions presented herein are depicted in the accompanying drawings wherein:

FIG. 1: illustrates a sequence alognment of the yeast elo1 peptide (upper row) with *physcomitrella patens* PpSE1 (SEQ ID NO:2);

FIGS. 3a-b: illustrate the structure and mass spectra of the DMOX derivatives of cis-Δ6, 9, 12, C18:3;

FIGS. 4a-b: illustrate the structure and mass spectra of the DMOX derivatives of cis-Δ8, 11, 14, C20:3;

FIG. 5: illustrates a comparison of positions 122-181, 182-236, and 237-277 of the Pp_PSE1 peptide sequence (SEQ ID NO:2) with positions 41-96, 97-145, and 146-186 of the sequence of SEQ ID NO:4, respectively;

FIG. 6: illustrates a comparison of positions 189-205 of the Pp_PSE1 peptide sequence (SEQ ID NO:2) with positions 174-190 of the sequence of SEQ ID NO:6;

FIG. 7: illustrates a comparison of positions 127-184, and 185-203 of the Pp_PSE1 peptide sequence (SEQ ID NO:2) with positions 33-87, and 88-106 of the sequence of the sequence of Cc_PSE1 (SEQ ID NO:8), respectively;

FIG. 8: illustrates a comparison of positions 1-49, 50-95, 96-143, 144-192, 193-240, 241-263, and 264-290 of the Pp_PSE1 peptide sequence (SEQ ID NO:2) with positions 1-36, 37-82, 83-131, 132-177, 178-220, 221-270, and 271-297 of the sequence of Tc_PSE2 (SEQ ID NO:6), respectively;

FIG. 9: illustrates a comparison of positions 6-55, 56-105, 106-145, and 146-180 of the Cc_PSE1 peptide sequence (SEQ ID NO:8) with positions 90-137, 138-186, 187-234, and 235-283 of the sequence of Tc_PSE2 (SEQ ID NO:6), respectively; and FIG. 10: illustrates sequence motifs.

DETAILED DESCRIPTION OF THE INVENTION

Figure 2A:
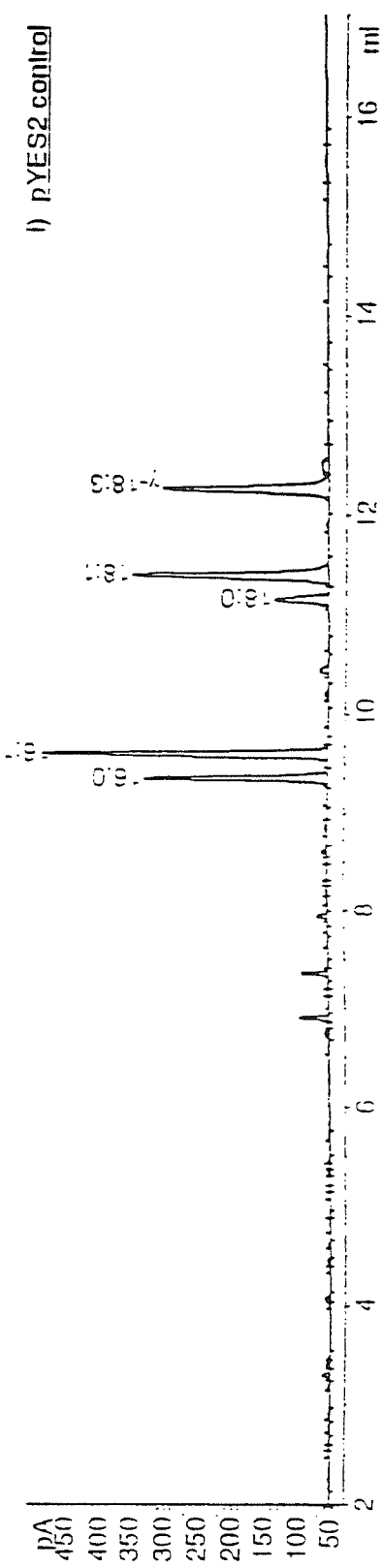
FIGS. 2a-2e: illustrate GC analyses of FAMEs which from total lipids of yeast transformed with pYES2 (i/control) and pY2PSE1 (ii-iv-c+d) in each case transformed with pY2PSE1A, pY2PSE1B, pY2PSE1C, and pY2PSE1D.

The present invention provides PSE nucleic acids and PSE protein molecules which participate in the metabolism of lipids and fatty acids, PUFA cofactors and enzymes in the moss *Physcomitrella patens, Phytophthora infestans, Crypthecodinium* or *Traustochytrium* or in the transport of lipophilic compounds via membranes. The compounds according to the invention can be used for modulating the production of fine chemicals from organisms, for example microorganisms, such as ciliates, fungi, yeasts, bacteria, algae, and/or plants such as maize, wheat, rye, oats, triticale, rice, barley, soybean, peanut, cotton, *Brassica* species, such as oilseed rape, canola and turnip rape, pepper, sunflower, borage, evening primrose and tagetes, Solanaceae plants such as potato, tobacco, aubergine and tomato, *Vicia* species, pea, cassava, alfalfa, shrub plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) or they can have an indirect effect which nevertheless leads to an increased yield, production and/or production efficiency of a desired compound or to a decrease in undesired compounds (for example when the modulation of the lipid and fatty acid, cofactor and enzyme metabolism leads to changes in yield, production and/or production efficacy or in the composition of the desired compounds within the cells, which, in turn, may affect the production of one or more fine chemicals). Aspects of the invention are illustrated in greater detail hereinbelow.

I. Fine Chemicals and PUFAs

The term "fine chemicals" is known in the art and encompasses molecules which have been produced by an organism and which are used in a variety of industries such as, by way of example but not by way of limitation, the pharmaceuticals industry, agroindustry, food industry and cosmetics industry. These compounds encompass lipids, fatty acids, cofactors and enzymes and the like (as described, for example, in Kuninaka, A. (1996) Nucleotides and related compounds, pp. 561-612, in Biotechnology Vol. 6, Rehm et al., Ed.: VCH Weinheim and references cited therein), lipids, saturated and unsaturated fatty acids (for example arachidonic acid), vitamins and cofactors (as described in Ullmann's Encyclopedia of Industrial Chemistry, Vol. A27, Vitamins, pp. 443-613 (1996): VCH Weinheim, and references cited therein; and Ong, A. S., Niki, E., & Packer, L. (1995) Nutrition, Lipids, Health and Disease Proceedings of the UNESCO/Confederation of Scientific and Technological Associations in Malaysia and the Society for Free Radical Research—Asia, held Sep. 1-3, 1994 in Penang, Malaysia, AOCS Press (1995)), enzymes and all other chemicals described by Gutcho (1983) in Chemicals by Fermentation, Noyes Data Corporation, ISBN: 0818805086 and references cited therein. The metabolism and the uses of certain fine chemicals are illustrated in greater detail hereinbelow.

The combination of various precursor molecules and biosynthetic enzymes leads to the production of various fatty acid molecules, which has a decisive effect on membrane composition. It can be assumed that PUFAs are not only just incorporated into triacylglycerol, but also into membrane lipids.

Membrane synthesis is a well characterized process in which a number of components, inclusive of lipids as part of the bilayer membrane, are involved. The production of novel fatty acids such as PUFAs can therefore generate novel properties of membrane functions within a cell or an organism.

Cell membranes serve a multiplicity of functions in a cell. First and foremost, a membrane delimits the contents of a cell from the environment, thus imparting integrity to the cell. Membranes can also act as barriers against the influx of dangerous or undesired compounds or else against the efflux of desired compounds.

For more detailed descriptions of involvements of membranes and the mechanisms involved, see Bamberg, E., et al. (1993) Charge transport of ion pumps on lipid bilayer membranes, Q. Rev. Biophys. 26:1-25; Gennis, R. B. (1989) Pores, Channels and Transporters, in: Biomembranes, Molecular Structure and Function, Springer: Heidelberg, pp. 270-322; and Nikaido, H., and Saier, H. (1992) Transport proteins in bacteria: common themes in their design, Science 258:936-942, and the citations contained in each of these references.

Lipid synthesis can be divided into two parts: the synthesis of fatty acids and their binding to sn-glycerol-3-phosphate, and the addition or modification of a polar head group. Customary lipids used in membranes encompass phospholipids, glycolipids, sphingolipids and phosphoglycerides. Fatty acid synthesis starts with the conversion of acetyl-CoA either into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydration reactions to give a saturated fatty acid molecule with the desired chain length. The production of the unsaturated fatty acids from these molecules is catalyzed by specific desaturases, either aerobically by means of molecular oxygen or anaerobically (as regards fatty acid synthesis in microorganisms, see F. C. Neidhardt et al. (1996) *E. coli* and *Salmo-* nella. ASM Press: Washington, D.C., pp. 612-636 and references contained therein; Lengeler et al. (Ed.) (1999) Biology of Procaryotes. Thieme: Stuttgart, New York, and the references contained therein, and Magnuson, K., et al. (1993) Microbiological Reviews 57:522-542 and the references contained therein).

Examples of precursors for PUFA biosynthesis are linolic and linolenic acid. These $C_{18}$ carbon fatty acids must be elongated to $C_{20}$ or $C_{22}$ to give fatty acids of the eicosa and docosa chain type. Various desaturases such as enzymes which have Δ6 desaturase, Δ5- and Δ4-desaturase activity can lead to arachidonic acid, eicosapentaenoic acid and docosahexaenoic acid and various other long-chain PUFAs which can be extracted and used for various purposes in food and feed, cosmetic or pharmaceutical applications.

To produce long chain PUFAs, the polyunsaturated $C_{16}$- or $C_{18}$- or $C_{20}$-fatty acids must, as mentioned above, be elongated by at least two carbon atoms by the enzymatic activity of an elongase. The nucleic acid sequences according to the invention encode first microbial elongases from typical producers containing PUFA in the triacylglycerol fraction, which elongases are capable of elongating the $C_{16}$- or $C_{18}$- or $C_{20}$-fatty acids with at least two double bonds in the fatty acid by at least two carbon atoms or which convert these, for example sequentially in succession, by converting a $C_{16}$- or $C_{18}$-fatty acid into a $C_{20}$-fatty acid and then a $C_{20}$- into a $C_{22}$- or higher even numbered fatty acid containing units with 2 C atoms. After one elongation cycle, this enzyme activity leads to $C_{20}$-fatty acids, and after two, three and four elgonation cycles to $C_{22}$-, $C_{24}$- or $C_{26}$-fatty acids. Longer PUFAs can also be synthesized with the elongase according to the invention. The activity of the elongases according to the invention preferably leads to $C_{20}$- and/or $C_{22}$-fatty acids with at least two double bonds in the fatty acid molecule, $C_{20}$-fatty acids, preferably with three, four or five double bonds, especially preferably three double bonds, in the fatty acid molecule, $C_{22}$-fatty acids, preferably with three, four, five or six double bonds, especially preferably five or six double bonds, in the fatty acid molecule. After elongation with the enzyme according to the invention, further desaturation steps may be carried out. Thus, the products of the elongase activities and of the further desaturation which is possible lead to preferred PUFAs with a higher degree of desaturation, such as docosadienoic acid, arachidonic acid, ω6-eicosatrienedihomo-γ-linolenic acid, eicosapentaenoic acid, ω3-eicosatrienoic acid, ω3-eicosatetraenoic acid, docosapentaenoic acid or docosahexaenoic acid. Examples of substrates of this enzyme activity according to the invention are taxol acid, 7,10,13-hexadecatrienoic acid, 6,9-octadecadienoic acid, linolic acid, γ-linolenic acid, pinolenic acid, α-linolenic acid, arachidonic acid, eicosapentaenoic acid or stearidonic acid. Preferred substrates are linolic acid, γ-linolenic acid and/or α-linolenic acid or arachidonic acid, eicosatetraenoic acid or eicosapentaenoic acid. The $C_{16}$- or $C_{18}$- or $C_{20}$-fatty acids with at least two double bonds in the fatty acid can be elongated by the enzyme activity according to the invention in the form of the free fatty acid or in the form of the esters, such as phospholipids, glycolipids, sphingolipids, phosphoglycerides, monoacylglycerol, diacylglycerol or triacylglycerol.

Furthermore, fatty acids must subsequently be transported to various locations and incorporated into the triacylglycerol storage lipid. Another important step in lipid synthesis is the transfer of fatty acids to the polar head groups, for example by glycerol fatty acid acyltransferase (see Frentzen, 1998, Lipid, 100(4 5):161-166).

For publications on plant fatty acid biosynthesis, desaturation, lipid metabolism and the membrane transport of fatty compounds, beta-oxidation, fatty acid modification and cofactors, triacylglycerol storage and assembly inclusive of the references cited therein, see the following articles: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: JK Setlow, 18:111-13; Gerhardt, 1992, Prog. Lipid R. 31:397-417; Gühnemann Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150 158, Murphy & Ross 1998, Plant Journal. 13(1):1-16.

Vitamins, cofactors and "nutraceuticals", such as PUFAs, encompass a group of molecules which higher animals can no longer synthesize and therefore have to take up, or which higher animals can no longer synthesize themselves to a sufficient degree and must therefore take up additionally, even though they are readily synthesized by other organisms such as bacteria. The biosynthesis of these molecules in organisms which are capable of producing them, such as in bacteria, has been more or less characterized (Ullmann's Encyclopedia of Industrial Chemistry, "Vitamins", Vol. A27, pp. 443-613, VCH Weinheim, 1996; Michal, G. (1999) Biochemical Pathways: An Atlas of Biochemistry and Molecular Biology, John Wiley & Sons; Ong, A. S., Niki, E., & Packer, L. (1995) "Nutrition, Lipids, Health and Disease" Proceedings of the UNESCO/Confederation of Scientific and Technological Associations in Malaysia and the Society for Free Radical Research Asia, held Sep. 1-3, 1994, in Penang, Malaysia, AOCS Press, Champaign, Ill. X, 374 pp).

The abovementioned molecules are either biologically active molecules themselves or precursors of biologically active substances which act either as electron carriers or as intermediates in a multiplicity of metabolic pathways. Besides their nutritional value, these compounds also have a significant industrial value as colorants, antioxidants and catalysts or other processing auxiliaries. (For a review over structure, activity and industrial applications of these compounds, see, for example, Ullmann's Encyclopedia of Industrial Chemistry, "Vitamins", Vol. A27, pp. 443-613, VCH Weinheim, 1996). Polyunsaturated fatty acids have a variety of functions and health promoting effects, for example in the case of coronary heart disease, inflammatory mechanisms, children's nutrition and the like. For publications and references including the references cited therein, see: Simopoulos, 1999, Am. J. Clin. Nutr. 70 (3rd Suppl.):560-569, Takahata et al., Biosc. Biotechnol. Biochem. 1998, 62(11):2079-2085, Willich and Winther, 1995, Deutsche Medizinische Wochenschrift 120(7):229 et seq.

II. Elements and Processes of the Invention

The present invention is based at least in part on the discovery of novel molecules termed herein PSE nucleic acid and PSE protein molecules, which exert an effect on the production of cell membranes in *Physcomitrella patens, Crypthecodinium cohnii, Phytophthora infestans, Thraustochytrium* and/or *Ceratodon purpureus* and, for example, have an effect on the movement of molecules via these membranes. In one embodiment, the PSE molecules participate in the metabolism of compounds required for the synthesis of cell membranes in organisms such as microorganisms and plants or indirectly affect the transport of molecules via these membranes. In a preferred embodiment, the activity of the PSE molecules according to the invention for regulating the production of membrane components and membrane transport has an effect on the production of the desired fine chemical by this organism. In an especially preferred embodiment, the activity of the PSE molecules according to the invention is modulated so that the yield, production and/or production efficiency of the metabolic pathways of microorganisms or plants which regulate the PSEs according to the invention are modulated and the transport efficiency of compounds through the membranes is modified, which either directly or indirectly modulates the yield, production and/or production efficiency of a desired fine chemical by microorganisms and plants.

The term PSE or PSE polypeptide encompasses proteins which participate in the metabolism of compounds required for the synthesis of cell membranes in organisms such as microorganisms and plants or in the transport of molecules via these membranes. Examples of PSEs are disclosed in SEQ ID NO:1, SEQ ID NO:3, SEQ ID NO:5, SEQ ID NO:7, SEQ ID NO:9 and SEQ ID NO:11 or their homologs, derivatives or analogs. The terms PSE or PSE nucleic acid sequence(s) encompass nucleic acid sequences which encode a PSE and part of which can be a coding region and also corresponding 5'- and 3'-untranslated sequence regions. Examples of PSE genes are the sequences shown in SEQ ID NO:1, SEQ ID NO:3, SEQ ID NO:5, SEQ ID NO:7, SEQ ID NO:9 and SEQ ID NO:11. The terms production and productivity are known in the art and encompass the concentration of the fermentation product (for example of the desired fine chemical) which is formed within a certain period and in a certain fermentation volume (for example kg product per hour per liter). The term production efficiency encompasses the time required for achieving a particular product quantity (for example the time required by the cell to establish a particular throughput rate of a fine chemical). The term yield or product/carbon yield is known in the art and encompasses the efficiency with which the carbon source is converted into the product (i.e. the fine chemical). This is usually expressed as, for example, kg product per kg carbon source. Increasing the yield or production of the compound increases the amount of the molecules obtained or of the suitable molecules of this compound obtained in a specific quantity of culture over a defined period. The terms biosynthesis or biosynthetic pathway are known in the art and encompass the synthesis of a compound, preferably of an organic compound, by a cell from intermediates, for example in a multi-step process which is subject to strong regulation. The terms catabolism or catabolic pathway are known in the art and encompass the cleavage of a compound, preferably of an organic compound, by a cell into catabolites (in general smaller or less complex molecules), for example in a multi-step process which is subject to strong regulation. The term metabolism is known in the art and encompasses the totality of the biochemical reactions which take place in an organism. The metabolism of a certain compound (for example the metabolism of a fatty acid) thus encompasses the totality of the biosynthetic, modification and catabolic pathways of this compound in the cell which are relevant to this compound.

In another embodiment, the PSE molecules according to the invention can modulate the production of a desired molecule, such as a fine chemical, in a microorganism or in plants. There exists a series of mechanisms by which the modification of a PSE according to the invention can directly affect the yield, production and/or production efficiency of a fine chemical from a microorganism strain or plant strain comprising this modified protein. The number or activity of PSEs participating in the transport of molecules of fine chemicals within, or out of, the cell can be increased, so that greater amounts of these compounds are transported via membranes, from which they can be obtained and converted into each other with greater ease. Furthermore, fatty acids, triacylglycerols and/or lipids are desirable fine chemicals themselves; optimizing the activity or increasing the number of one or more PSEs according to the invention which participate in the biosynthesis of these compounds, or by interfering with the activity of one or more PSEs which participate in the catabolism of these compounds makes increasing the yield, production and/or production efficiency of fatty acid molecules and lipid molecules from organisms such as microorganisms or plants, possible.

The mutagenesis of the PSE gene according to the invention can also give rise to PSEs with modified activities which indirectly affect the production of one or more desired fine chemicals from microorganisms or plants. For example, PSEs according to the invention which participate in the export of waste products can exhibit a greater number or higher activity, so that the normal metabolic waste products of the cell (whose quantity might be increased owing to the overproduction of the desired fine chemical) are exported efficiently before they can damage the molecules in the cell (which would reduce the cell's viability) or interfere with the biosynthetic pathways of the fine chemicals (which would reduce the yield, production or production efficiency of a desired fine chemical). The relatively large intracellular amounts of the desired fine chemical themselves can furthermore be toxic to the cell, so that increasing the activity or number of transporters capable of exporting these compounds from the cell results in an increased viability of the cell in culture, which, in turn, leads to a higher number of cells in the culture which produce the desired fine chemical. The PSEs according to the invention can also be manipulated in such a way that the corresponding amounts of different lipid molecules and fatty acid molecules are produced. This can have a substantial effect on the lipid composition of the cell membrane. Since each lipid type has different physical properties, a modification of the lipid composition of a membrane can significantly modify membrane fluidity. Modifications of the membrane fluidity can affect the transport of molecules via the membrane and cell integrity, each of which has a substantial effect on the production of fine chemicals from microorganisms and plants in large scale fermentation culture. Plant membranes impart specific properties such as tolerance to high and low temperatures, salt, drought and tolerance with respect to pathogens such as bacteria and fungi. The modulation of the membrane components may therefore have a critical effect on the ability of the plants to survive under the abovementioned stress parameters. This can take place via changes in signal cascades or directly via the modified membrane composition (see, for example, Chapman, 1998, Trends in Plant Science, 3(11):419-426) and signal cascades (see Wang 1999, Plant Physiology, 120:645-651) or affect the tolerance of low temperatures, as disclosed in WO 95/18222.

The isolated nucleic acid sequences according to the invention are present, for example, in the genome of a *Thraustochytrium* strain which is available via the American Type Culture Collection (ATCC) with the strain number ATCC26185 (*Thraustochytrium*), or, in the case of *Crypthecodinium*, for example, accessible via the Provasoli-Guillard National Center for Culture of Marine Phytoplankton ((CCMP) West Boothbay Harbour, Me., USA) with the strain culture No. CCMP316. In the case of *Phytophthora infestans*, the stated nucleic acid molecules are isolated from the strain ATCC 48886.

The nucleotide sequence of the isolated *Physcomitrella, Crypthecodinium, Phytophthora infestans* or *Thraustochytrium* cDNA and the deduced amino acid sequences of the *Physcomitrella patens* PSEs are shown in SEQ ID NO:1 to SEQ ID NO:12. Computer analyses were carried out which classify and/or identify these nucleotide sequences as sequences which encode proteins participating in the metabolism of cell membrane components or which participate in the transport of compounds via cell membranes, or of PUFA biosynthesis. ESTs with the database input No. PP001019019F, CC001042041R, PI001002014R, TC002034029R, TC002034029R-11 and TC002014093R in the database of the inventor constitute the sequences according to the invention in SEQ ID NO:1, SEQ ID NO:3, SEQ ID NO:5, SEQ ID NO:7, SEQ ID NO:9 and SEQ ID NO:11. In a similar manner, the partial polypeptides were termed PP001019019F, CC001042041R, PI001002014R, TC002034029R, TC002034029R-11 and TC002014093R and constitute the sequences according to the invention in SEQ ID NO:2, SEQ ID NO:4, SEQ ID NO:6, SEQ ID NO:8, SEQ ID NO:10 and SEQ ID NO:12 in accordance with Table 2. The complete fragment insert of the ESTs TC002034029R was sequenced and resulted in SEQ ID NO:3, which is the complete sequence of TC002034029R. TC002034029R-11 describes a full length sequence of an elongase from *Thraustochytrium*. The naming of the remaining clones is similar. Also, corresponding gene names were assigned to the various clones. Abbreviations: Tc=*Thraustochytrium*, Cc=*Crypthecodinium*, Pp=*Physcomitrella patens*, P: *Phytophthora infestans*.

TABLE 2

| Name/EST name | Gene name | Polypeptide SEQ ID NO | Nucleic acid SEQ ID NO |
|---|---|---|---|
| PP001019019F | Pp_PSE1 | 2 | 1 |
| TC002034029R | Tc_PSE1 | 4 | 3 |
| TC002014093R | Tc_PSE2 | 6 | 5 |
| CC001042041R | Cc_PSE1 | 8 | 7 |
| TC002034029R-11 | Tc_PSE1_1 | 10 | 9 |
| PI001002014R | Pi_PSE1 | 12 | 11 |

The present invention also relates to proteins with an amino acid sequence which is essentially homologous with an amino acid sequence of SEQ ID NO:2, SEQ ID NO:4, SEQ ID NO:6, SEQ ID NO:8, SEQ ID NO:10 and SEQ ID NO:12. As used in the present context, a protein with an amino acid sequence which is essentially homologous with a selected amino acid sequence has at least approximately 50% homology with the selected amino acid sequence, for example the complete amino acid sequence selected. A protein with an amino acid sequence which is essentially homologous with a selected amino acid sequence can also have at least approximately 50 to 60%, preferably at least approximately 60 to 70%, more preferably at least approximately 70 to 80%, 80 to 90% or 90 to 95%, and most preferably at least approximately 96%, 97%, 98%, 99% or more homology with a selected amino acid sequence.

The PSE according to the invention or the biologically active part or the fragment thereof can participate in the metabolism of compounds required for the synthesis of cell membranes in microorganisms or plants or in the transport of molecules via these membranes or have one or more of the activities required for the elongation of $C_{16}$- or $C_{18}$- or $C_{20}$-PUFAs, so that $C_{20}$-, $C_{22}$- or $C_{24}$-PUFAs and related PUFAs are obtained.

Various aspects of the invention are described in greater detail in the subsections which follow.

a. Isolated Nucleic Acid Molecules

One embodiment of the invention comprises isolated nucleic acids derived from PUFA producing microorganisms and encoding polypeptides which elongate $C_{16}$- or $C_{18}$-fatty acids with at least two double bonds in the fatty acid by at least two carbon atoms or which elongate $C_{20}$-fatty acids with at least two double bonds in the fatty acid by at least two carbon atoms.

A further embodiment according to the invention comprises isolated nucleic acids encompassing nucleotide sequences encoding polypeptides which elongate $C_{16}$-, $C_{18}$- or $C_{20}$-fatty acids with at least two double bonds in the fatty acid and which are selected from the group consisting of a) the nucleic acid sequences shown in SEQ ID NO:1, SEQ ID NO:3, SEQ ID NO:5, SEQ ID NO:7, SEQ ID NO:9 and SEQ ID NO:11, b) a nucleic acid sequence which, in accordance with the degeneracy of the genetic code, is derived from one of the sequences shown in SEQ ID NO:1, SEQ ID NO:3, SEQ ID NO:5, SEQ ID NO:7, SEQ ID NO:9 and SEQ ID NO:11 or c) derivatives of the sequence shown in SEQ ID NO:1, SEQ ID NO:3, SEQ ID NO:5, SEQ ID NO:7, SEQ ID NO:9 and SEQ ID NO:11 which encode polypeptides of the amino acid sequence shown in SEQ ID NO:2, SEQ ID NO:4, SEQ ID NO:6, SEQ ID NO:8, SEQ ID NO:10 and SEQ ID NO:12 and which have at least 50% homology at the amino acid level without the enzymatic action of the polypeptides being substantially reduced.

The abovementioned nucleic acids according to the invention, which act as $C_{16}$-, $C_{18}$- or $C_{20}$-elongase, are derived from organisms such as ciliates, fungi, algae, plants or dinoflagellates which are capable of synthesizing PUFAs, preferably from plants or algae, especially preferably from the genus *Phytophthora*, *Physcomitrella*, *Crypthecodinium*, *Thraustochytrium* or *Schizochytrium*, most preferably from *Phytophthora infestans*, *Physcomitrella patens*, *Crypthecodinium cohnii* or *Thraustochytrium* sp., *Schizochytrium* sp. or closely related organisms.

One aspect of the invention relates to isolated nucleic acid molecules which encode PSE polypeptides or biologically active parts thereof, and to nucleic acid fragments which suffice for use as hybridization probes or primers for identifying or amplifying a PSE-encoding nucleic acid (for example PSE DNA). The term "nucleic acid molecule" as used in the present context is intended to encompass DNA molecules (for example cDNA or genomic DNA) and RNA molecules (for example mRNA) and DNA or RNA analogs which are generated by means of nucleotide analogs. This term additionally encompasses the untranslated sequence at the 3' and the 5' end of the coding gene region: at least approximately 100 nucleotides of the sequence upstream of the 5' end of the coding region and at least approximately 20 nucleotides of the sequence downstream of the 3' end of the coding gene region. The nucleic acid molecule can be single- or double-stranded, but is preferably double-stranded DNA. An "isolated" nucleic acid molecule is separated from other nucleic acid molecules which are present in the natural source of the nucleic acid. An "isolated" nucleic acid preferably has no sequences which naturally flank the nucleic acid in the genomic DNA of the organism from which the nucleic acid is derived (for example sequences located at the 5' and 3' ends of the nucleic acid). In various embodiments, the isolated PSE nucleic acid molecule can contain, for example, less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid is derived (for example a *Physcomitrella patens* cell). An "isolated" nucleic acid molecule, such as a cDNA molecule, can moreover be essentially free from other cellular material or culture medium if it is generated by recombinant techniques, or free from chemical precursors or other chemicals if it is synthesized chemically.

A nucleic acid molecule according to the invention, for example a nucleic acid molecule with a nucleotide sequence of SEQ ID NO:1, SEQ ID NO:3, SEQ ID NO:5, SEQ ID NO:7, SEQ ID NO:9 and SEQ ID NO:11 or a part thereof, can be isolated using standard techniques of molecular biology and the sequence information provided herein. Also, for example a homologous sequence or homologous, conserved sequence regions at the DNA or amino acid level can be identified with the aid of alignment algorithms. For example, a *Phytophthora, Physcomitrella, Crypthecodinium* or *Thraustochytrium* cDNA can be isolated from a *Phytophthora, Physcomitrella, Crypthecodinium* or *Thraustochytrium* library by using the complete SEQ ID NO:1, SEQ ID NO:3, SEQ ID NO:5, SEQ ID NO:7, SEQ ID NO:9 and/or SEQ ID NO:11 or a part thereof as hybridization probe and standard hybridization techniques (such as, for example, as described in Sambrook et al., Molecular Cloning: A Laboratory Manual. 2nd Ed., Cold Spring Harbor Laboratory, Cold Spring Harbor Laboratory Press, Cold Spring Harbor, N.Y., 1989). Moreover, a nucleic acid molecule encompassing a complete sequence of SEQ ID NO:1, SEQ ID NO:3, SEQ ID NO:5, SEQ ID NO:7, SEQ ID NO:9 and SEQ ID NO:11 or a part thereof can be isolated by polymerase chain reaction, where oligonucleotide primers which are generated on the basis of this sequence or parts thereof, in particular regions around His-box motifs of SEQ ID NO:2, SEQ ID NO:4, SEQ ID NO:6, SEQ ID NO:8, SEQ ID NO:10 and SEQ ID NO:12 or modifications of the same in individual, defined amino acids are used (for example, a nucleic acid molecule encompassing the complete sequence of SEQ ID NO:1, SEQ ID NO:3, SEQ ID NO:5, SEQ ID NO:7, SEQ ID NO:9 and SEQ ID NO:11 or a part thereof can be isolated by polymerase chain reaction using oligonucleotide primers which have been generated on the basis of this same sequence of SEQ ID NO:1, SEQ ID NO:3, SEQ ID NO:5, SEQ ID NO:7, SEQ ID NO:9 and SEQ ID NO:11). Furthermore, especially suitable for this purpose are those partial sequences as they are shown in FIG. 10. For example, mRNA can be isolated from cells (for example by the guanidinium thiocyanate extraction method by Chirgwin et al. (1979) Biochemistry 18:5294-5299), and cDNA can be generated by means of reverse transcriptase (for example Moloney MLV reverse transcriptase, available from Gibco/BRL, Bethesda, Md., or AMV reverse transcriptase, availabe from Seikagaku America, Inc., St. Petersburg, Fla.). Synthetic oligonucleotide primers for amplification by means of polymerase chain reaction can be generated on the basis of one of the nucleotide sequences shown in SEQ ID NO:1, 3, 5, 7, 9 or 11 or with the aid of the amino acid sequences shown in FIG. 10. A nucleic acid according to the invention can be amplified using cDNA or, alternatively, using genomic DNA as template and suitable oligonucleotide primers, in accordance with standard PCR amplification techniques. The nucleic acid thus amplified can be cloned into a suitable vector and characterized by means of DNA sequence analysis. Oligonucleotides which correspond to a PSE nucleotide sequence can be generated by standard synthesis methods, for example with an automatic DNA synthesizer.

The cDNA shown in SEQ ID NO:1, SEQ ID NO:3, SEQ ID NO:5, SEQ ID NO:7, SEQ ID NO:9 and SEQ ID NO:11 encompasses sequences which encode PSEs (i.e. the "coding region") and also 5'-untranslated sequences and 3'-untranslated sequences. Alternatively, the nucleic acid molecule can only encompass the coding region of one of the sequences in SEQ ID NO:1, SEQ ID NO:3, SEQ ID NO:5, SEQ ID NO:7, SEQ ID NO:9 and SEQ ID NO:11 or can comprise complete genomic fragments isolated from genomic DNA.

SEQ ID NO:2, SEQ ID NO:4, SEQ ID NO:6, SEQ ID NO:8, SEQ ID NO:10 and SEQ ID NO:12 are identified by the same EST input number code as SEQ ID NO:1, SEQ ID NO:3, SEQ ID NO:5, SEQ ID NO:7, SEQ ID NO and SEQ ID NO:11 for ease of correlation.

In a further preferred embodiment, an isolated nucleic acid molecule according to the invention encompasses a nucleic acid molecule which is a complement of one of the nucleotide sequences shown in SEQ ID NO:1, SEQ ID NO:3, SEQ ID NO:5, SEQ ID NO:7, SEQ ID NO and SEQ ID NO:11 or a part thereof. A nucleic acid molecule which is complementary to one of the nucleotide sequences shown in SEQ ID NO:1, SEQ ID NO:3, SEQ ID NO:5, SEQ ID NO:7, SEQ ID NO:9 and SEQ ID NO:11 is sufficiently complementary if it is capable of hybridizing with one of the sequences stated in SEQ ID NO:1, SEQ ID NO:3, SEQ ID NO:5, SEQ ID NO:7, SEQ ID NO:9 and SEQ ID NO:11, giving rise to a stable duplex.

Homologs of the new elongase nucleic acid sequences with the sequence SEQ ID NO:1, SEQ ID NO:3, SEQ ID NO:5, SEQ ID NO:7, SEQ ID NO:9 and SEQ ID NO:11 means, for example, allelic variants with at least approximately 50 to 60%, preferably at least approximately 60 to 70%, more preferably at least approximately 70 to 80%, 80 to 90% or 90 to 95%, and even more preferably at least approximately 95%, 96%, 97%, 98%, 99% or more homology with one of the nucleotide sequences shown in SEQ ID NO:1, SEQ ID NO:3, SEQ ID NO:5, SEQ ID NO:7, SEQ ID NO:9 and SEQ ID NO:11 or their homologs, derivatives or analogs or parts thereof. In a further preferred embodiment, an isolated nucleic acid molecule according to the invention encompasses a nucleotide sequence which hybridizes with one of the nucleotide sequences shown in SEQ ID NO:1, SEQ ID NO:3, SEQ ID NO:5, SEQ ID NO:7, SEQ ID NO and SEQ ID NO:11 or a part thereof, under stringent conditions. Allelic variants encompass, in particular, functional variants which can be obtained by the deletion, insertion or substitution of nucleotides from/into the sequence shown in SEQ ID NO:1, SEQ ID NO:3, SEQ ID NO:5, SEQ ID NO:7, SEQ ID NO:9 and SEQ ID NO:11, it being intended, however, for the enzyme activity of the resulting proteins which are synthesized to be advantageously retained for the insertion of one or more genes. Proteins which retain the enzymatic activity of elongase means proteins with at least 10%, preferably 20%, especially preferably 30%, very especially preferably 40% of the original enzyme activity compared with the protein encoded by SEQ ID NO:2, SEQ ID NO:4, SEQ ID NO:6, SEQ ID NO:8, SEQ ID NO:10 and SEQ ID NO:12. Elongases which retain the abovementioned activities are elongases whose enzymatic activity is not substantially reduced.

Homologs of SEQ ID NO:1, SEQ ID NO:3, SEQ ID NO:5, SEQ ID NO:7, SEQ ID NO:9 and SEQ ID NO:11 also means, for example, bacterial, fungal and plant homologs, truncated sequences, single-stranded DNA or RNA of the coding and noncoding DNA sequence.

Homologs of SEQ ID NO:1, SEQ ID NO:3, SEQ ID NO:5, SEQ ID NO:7, SEQ ID NO:9 and SEQ ID NO:11 also means derivatives such as, for example, promoter variants. The promoters upstream of the nucleotide sequences stated can be modified by one or more nucleotide substitutions, by insertion(s) and/or deletion(s), without, however, interfering with the functionality or activity of the promoters. It is furthermore possible for the activity of the promoters to be increased by modification of their sequence or for them to be replaced completely by more active promoters, even from heterologous organisms.

Moreover, the nucleic acid molecule according to the invention can only encompass part of the coding region of one of the sequences in SEQ ID NO:1, SEQ ID NO:3, SEQ ID NO:5, SEQ ID NO:7, SEQ ID NO:9 and SEQ ID NO:11, for example a fragment which can be used as probe or primer or a fragment which encodes a biologically active segment of a PSE. The nucleotide sequences determined from cloning the PSE gene of *Physcomitrella patens*, *Phytophthora infestans*, *Thraustochytrium* and *Crypthecodinium* allow the generation of probes and primers which are designed for identifying and/or cloning PSE homologs in other cell types and organisms and PSE homologs from other mosses or related species. The probe/primer normally encompasses essentially purified oligonucleotide. The oligonucleotide normally encompasses a nucleotide sequence region which hybridizes under stringent conditions with at least approximately 12, preferably approximately 16, more preferably approximately 25, 40, 50 or 75 successive nucleotides of a sense strand of one of the sequences stated in SEQ ID NO:1, SEQ ID NO:3, SEQ ID NO:5, SEQ ID NO:7, SEQ ID NO and SEQ ID NO:11, of an antisense strand of one of the sequences stated in SEQ ID NO:1, SEQ ID NO:3, SEQ ID NO:5, SEQ ID NO:7, SEQ ID NO and SEQ ID NO or its homologs, derivatives and analogs or naturally occurring mutants thereof. Primers based on a nucleotide sequence of SEQ ID NO:1, SEQ ID NO:3, SEQ ID NO:5, SEQ ID NO:7, SEQ ID NO and SEQ ID NO:11 can be used in PCR reactions for cloning PSE homologs. Probes based on the PSE nucleotide sequences can be used for detecting transcripts or genomic sequences which encode the same or homologous proteins. In preferred embodiments, the probe additionally encompasses a labeling group bound thereto, for example a radioisotope, a fluorescent compound, an enzyme or an enzyme cofactor. These probes can be used as part of a test kit for genomic markers for identifying cells which misexpress a PSE, for example by measuring an amount of a PSE-encoding nucleic acid in a cell sample, for example measuring the PSE mRNA level, or for determining whether a genomic PSE gene is mutated or deleted.

In one embodiment, the nucleic acid molecule according to the invention encodes a protein or a part thereof which encompasses an amino acid sequence which has sufficient homology with an amino acid sequence of SEQ ID NO:2, SEQ ID NO:4, SEQ ID NO:6, SEQ ID NO:8, SEQ ID NO:10 and SEQ ID NO:12 for the protein or the part thereof to retain the ability to participate in the metabolism of compounds required for the synthesis of cell membranes in microorganisms or plants or in the transport of molecules via these membranes. As used in the present context, the term "sufficient homology" relates to proteins or parts thereof whose amino acid sequences have a minimum number of amino acid residues (for example an amino acid residue with a similar side chain, such as an amino acid residue in one of the sequences of SEQ ID NO:2 to 12) which are identical with or equivalent to an amino acid sequence of SEQ ID NO:2, SEQ ID NO:4, SEQ ID NO:6, SEQ ID NO:8, SEQ ID NO:10 and SEQ ID NO:12 so that the protein or the part thereof can participate in the metabolism of compounds required for the synthesis of cell membranes in microorganisms or plants or in the transport of molecules via these membranes. As described herein, protein components of these metabolic pathways for membrane components or membrane transport systems can play a role in the production and secretion of one or more fine chemicals. Examples of these activities are also described herein. Thus, the "function of a PSE" contributes either directly or indirectly to the yield, production and/or production efficiency of one or more fine chemicals. Examples of PSE substrate specificities of the catalytic activity are stated in Table 1.

In a further embodiment, derivatives of the nucleic acid molecule according to the invention encode proteins with at least approximately 50 to 60%, preferably at least approximately 60 to 70% and more preferably at least approximately 70 to 80%, 80 to 90%, 90 to 95% and most preferably at least approximately 96%, 97%, 98%, 99% or more homology with a complete amino acid sequence of SEQ ID NO:2, SEQ ID NO:4, SEQ ID NO:6, SEQ ID NO:8, SEQ ID NO:10 and SEQ ID NO:12. The homology of the amino acid sequence was determined over the entire sequence region using the program PileUp (J. Mol. Evolution., 25, 351-360, 1987, Higgins et al., CABIOS, 5, 1989:151-153) or BESTFIT or GAP (Henikoff, S, and Henikoff, J. G. (1992). Amino acid substitution matrices from protein blocks. Proc. Natl. Acad. Sci. USA 89: 10915-10919.)

Parts of proteins encoded by the PSE nucleic acid molecules according to the invention are preferably biologically active parts of one of the PSEs. As used herein, the term "biologically active part of a PSE" is intended to encompass a segment, for example a domain/motif, of a PSE which can participate in the metabolism of compounds required for the synthesis of cell membranes in microorganisms or plants or in the transport of molecules via these membranes or which has an activity stated in Table 1. An assay of the enzymatic activity can be carried out in order to determine whether a PSE or a biologically active part thereof can participate in the metabolism of compounds required for the synthesis of cell membranes in microorganisms or plants or in the transport of molecules via these membranes. These assay methods as described in detail in Example 8 of the examples section are known to the skilled worker.

Additional nucleic acid fragments which encode biologically active segments of a PSE can be generated by isolating part of one of these sequences in SEQ ID NO:2, SEQ ID NO:4, SEQ ID NO:6, SEQ ID NO:8, SEQ ID NO:10 and SEQ ID NO:12, expressing the encoded segment of the PSE or of the peptide (for example by recombinant expression in vitro) and determining the activity of the encoded part of the PSE or of the peptide.

Moreover, the invention encompasses nucleic acid molecules which differ from one of the nucleotide sequences shown in SEQ ID NO:1, SEQ ID NO:3, SEQ ID NO:5, SEQ ID NO:7, SEQ ID NO:9 and SEQ ID NO:11 (and parts thereof) owing to the degeneracy of the genetic code and which thus encode the same PSE as the one encoded by the nucleotide sequences shown in SEQ ID NO:1, SEQ ID NO:3, SEQ ID NO:5, SEQ ID NO:7, SEQ ID NO:9 and SEQ ID NO:11. In another embodiment, an isolated nucleic acid molecule according to the invention has a nucleotide sequence which encodes a protein with an amino acid sequence shown in SEQ ID NO:2, SEQ ID NO:4, SEQ ID NO:6, SEQ ID NO:8, SEQ ID NO:10 and SEQ ID NO:12. In a further embodiment, the nucleic acid molecule according to the invention encodes a full-length PSE protein which is essentially homologous with an amino acid sequence of SEQ ID NO:2, SEQ ID NO:4, SEQ ID NO:6, SEQ ID NO:8, SEQ ID NO:10 and SEQ ID NO:12 (which is encoded by an open reading frame shown in SEQ ID NO:1, SEQ ID NO:3, SEQ ID NO:5, SEQ ID NO:7, SEQ ID NO:9 and SEQ ID NO:11) and which can be identified and isolated by customary methods.

In addition to the PSE nucleotide sequences shown in SEQ ID NO:1, SEQ ID NO:3, SEQ ID NO:5, SEQ ID NO:7, SEQ ID NO:9 and SEQ ID NO:11, the skilled worker recognizes that DNA sequence polymorphisms may exist which lead to changes in the amino acid sequences of the PSEs within a population (for example the *Physcomitrella, Phytophthora, Crypthecodinium* or *Thraustochytrium* population). These genetic polymorphisms in the PSE gene can exist between individuals within a population owing to natural variation. As used in the present context, the terms "gene" and "recombinant gene" refer to nucleic acid molecules with an open reading frame which encodes a PSE, preferably a *Phytophthora, Physcomitrella, Crypthecodinium* or *Thraustochytrium* PSE. These natural variants usually cause a variance of 1 to 5% in the nucleotide sequence of the PSE gene. All of these nucleotide variations and resulting amino acid polymorphisms in PSE which are the result of natural variation and do not alter the functional activity of PSEs are intended to come within the scope of the invention.

Nucleic acid molecules which correspond to the natural variants and non-*Physcomitrella*, -*Phytophthora*, -*Crypthecodinium* or -*Thraustochytrium* homologs, derivatives and analogs of the *Phytophthora, Physcomitrella, Crypthecodinium* or *Thraustochytrium* cDNA can be isolated in accordance with standard hybridization techniques under stringent hybridization conditions owing to their homology with the *Phytophthora, Physcomitrella, Crypthecodinium* or *Thraustochytrium* PSE nucleic acid disclosed herein using the *Physcomitrella, Phytophthora, Crypthecodinium* or *Thraustochytrium* cDNA or a part thereof as hybridization probe. In another embodiment, an isolated nucleic acid molecule according to the invention has a minimum length of 15 nucleotides and hybridizes under stringent conditions with the nucleic acid molecule which encompasses a nucleotide sequence of SEQ ID NO:1, SEQ ID NO:3, SEQ ID NO:5, SEQ ID NO:7, SEQ ID NO:9 and SEQ ID NO:11. In other embodiments, the nucleic acid has a minimum length of 25, 50, 100, 250 or more nucleotides. The term "hybridizes under stringent conditions" as used in the present context is intended to describe hybridization and wash conditions under which nucleotide sequences which have at least 60% homology with each other usually remain hybridized with each other. The conditions are preferably such that sequences which have at least approximately 65%, more preferably at least approximately 70% and even more preferably at least approximately 75% or more homology with each other usually remain hybridized with each other. These stringent conditions are known to the skilled worker and can be found in Current Protocols in Molecular Biology, John Wiley & Sons, N.Y. (1989), 6.3.1-6.3.6. A preferred, nonlimiting example of stringent hybridization conditions are hybridizations in 6× sodium chloride/sodium citrate (sodium chloride/sodium citrate=SSC) at approximately 45° C. followed by one or more wash steps in 0.2×SSC, 0.1% SDS at 50 to 65° C. It is known to the skilled worker that these hybridization conditions differ depending on the type of the nucleic acid and, for example when organic solvents are present, with regard to buffer temperature and concentration. For example, the temperature differs under "standard hybridization conditions" depending on the type of the nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably for example 0.1×SSC and 30° C. to 55° C., preferably between 45° C. and 55° C. The above-mentioned hybridization temperatures are determined for example for a nucleic acid approximately 100 bp (=base pairs) in length and a G+C content of 50% in the absence of formamide. The skilled worker knows how the hybridization conditions required can be determined with reference to textbooks, such as the one mentioned above or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

Preferably, an isolated nucleic acid molecule according to the invention which hybridizes under stringent conditions with a sequence of SEQ ID NO SEQ ID NO:3, SEQ ID NO:5, SEQ ID NO:7, SEQ ID NO and SEQ ID NO:11 corresponds to a naturally occurring nucleic acid molecule. As used in the present context, a "naturally occurring" nucleic acid molecule refers to an RNA or DNA molecule with a nucleotide sequence which occurs in nature (for example which encodes a natural protein). In one embodiment, the nucleic acid encodes a naturally occurring *Physcomitrella patens* PSE, *Phytophthora infestans* PSE, *Crypthecodinium cohnii* PSE or *Thraustochytrium* PSE.

In addition to naturally occurring variants of the PSE sequence which may exist in the population, the skilled worker furthermore recognizes that changes by means of mutation may also be introduced into a nucleotide sequence of SEQ ID NO:1, SEQ ID NO:3, SEQ ID NO:5, SEQ ID NO:7, SEQ ID NO:9 and SEQ ID NO:11, which leads to changes in the amino acid sequence of the encoded PSE without adversely affecting the functionality of the PSE protein. For example, nucleotide substitutions which lead to amino acid substitutions on "nonessential" amino acid residues can be generated in a sequence of SEQ ID NO:1, SEQ ID NO:3, SEQ ID NO:5, SEQ ID NO:7, SEQ ID NO:9 and SEQ ID NO:11. A "nonessential" amino acid residue is a residue which can be altered in a wild-type sequence of one of the PSEs (SEQ ID NO:2, SEQ ID NO:4, SEQ ID NO:6, SEQ ID NO:8, SEQ ID NO:10 and SEQ ID NO:12) without altering the activity of the PSE, while an "essential" amino acid residue is required for the PSE activity. Other amino acid residues (for example those which are not conserved, or only semi conserved, in the domain with PSE activity), however, may not be essential for the activity and can therefore probably be altered without altering the PSE activity.

Accordingly, a further aspect of the invention relates to nucleic acid molecules which encode PSEs comprising altered amino acid residues which are not essential for the PSE activity. These PSEs differ from a sequence in SEQ ID NO:2, SEQ ID NO:4, SEQ ID NO:6, SEQ ID NO:8, SEQ ID NO:10 and SEQ ID NO:12 with regard to the amino acid sequence while still retaining at least one of the PSE activities described herein. In one embodiment, the isolated nucleic acid molecule encompasses a nucleotide sequence encoding a protein, the protein encompassing an amino acid sequence with at least approximately 50% homology with an amino acid sequence of SEQ ID NO:2, SEQ ID NO:4, SEQ ID NO:6, SEQ ID NO:8, SEQ ID NO:10 and SEQ ID NO:12 and being able to participate in the metabolism of compounds required for the synthesis of cell membranes in *Phytophthora, Physcomitrella, Crypthecodinium* or *Thraustochytrium* or in the transport of molecules via these membranes. The protein encoded by the nucleic acid molecule preferably has at least approximately 50 to 60% homology with one of the sequences in SEQ ID NO:2, SEQ ID NO:4, SEQ ID NO:6, SEQ ID NO:8, SEQ ID NO:10 and SEQ ID NO:12, more preferably at least approximately 60 to 70% homology with one of the sequences in SEQ ID NO:2, SEQ ID NO:4, SEQ ID NO:6, SEQ SEQ ID NO and SEQ ID NO:12, even more preferably at least approximately 70 to 80%, 80 to 90%, 90 to 95% homology with one of the sequences in SEQ ID NO:2, SEQ ID NO:4, SEQ ID NO:6, SEQ ID NO:8, SEQ ID NO:10 and SEQ ID NO:12, and most preferably at least approximately 96%, 97%, 98% or 99% homology with one of the sequences in SEQ ID NO:2, SEQ ID NO:4, SEQ ID NO:6, SEQ ID NO:8, SEQ ID NO:10 and SEQ ID NO:12.

To determine the percentage homology of two amino acid sequences (for example one of the sequences of SEQ ID NO:2, SEQ ID NO:4, SEQ ID NO:6, SEQ ID NO:8, SEQ ID NO:10 and SEQ ID NO and a mutated form thereof) or of two nucleic acids, the sequences are written one underneath the other to allow optimal comparison (for example, gaps may be introduced into the sequence of a protein or of a nucleic acid in order to generate an optimal alignment with the other protein or the other nucleic acid). Then, the amino acid residues or nucleotides on the corresponding amino acid positions or nucleotide positions are compared. If a position in a sequence (for example one of the sequences of SEQ ID NO:2, SEQ ID NO:4, SEQ ID NO:6, SEQ ID NO:8, SEQ ID NO:10 and SEQ ID NO:12) is occupied by the same amino acid residue or the same nucleotide as the corresponding position in the other sequence (for example a mutated form of the sequence selected from SEQ ID NO:2, SEQ ID NO:4, SEQ ID NO:6, SEQ ID NO:8, SEQ ID NO:10 and SEQ ID NO:12), then the molecules are homologous at this position (i.e. amino acid or nucleic acid "homology" as used in the present context corresponds to amino acid or nucleic acid "identity"). The percentage homology between the two sequences is a function of the number of identical positions which the sequences share (i.e. % homology=number of identical positions/total number of positions ×100).

An isolated nucleic acid molecule which encodes a PSE which is homologous with a protein sequence of SEQ ID NO:2, SEQ ID NO:4, SEQ ID NO:6, SEQ ID NO:8, SEQ ID NO:10 and SEQ ID NO:12 can be generated by introducing one or more nucleotide substitutions, additions or deletions into a nucleotide sequence of SEQ ID NO:1, SEQ ID NO:3, SEQ ID NO:5, SEQ ID NO:7, SEQ ID NO:9 and SEQ ID NO:11 so that one or more amino acid substitutions, additions or deletions are introduced into the encoded protein. Mutations can be introduced into one of the sequences of SEQ ID NO:1, SEQ ID NO:3, SEQ ID NO:5, SEQ ID NO:7, SEQ ID NO:9 and SEQ ID NO:11 by standard techniques, such as site-directed mutagenesis and PCR-mediated mutagenesis. Preferably, conservative amino acid substitutions are generated at one or more of the predicted nonessential amino acid residues. In a "conservative amino acid substitution", the amino acid residue is exchanged for an amino acid residue with a similar side chain. Families of amino acid residues with similar side chains have been defined in the specialist field. These families encompass amino acids with basic side chains (for example lysine, arginine, histidine), acidic side chains (for example aspartic acid, glutamic acid), uncharged polar side chains (for example glycine, asparagine, glutamine, serine, threonine, tyrosine, cysteine), unpolar side chains, (for example alanine, valine, leucine, isoleucine, proline, phenylalanine, methionine, tryptophan), beta branched side chains (for example threonine, valine, isoleucine) and aromatic side chains (for example tyrosine, phenylalanine, tryptophan, histidine). A predicted nonessential amino acid residue in a PSE is thus preferably exchanged for another amino acid residue from the same side-chain family. As an alternative, in another embodiment, the mutations can be introduced randomly over all or part of the PSE-encoding sequence, for example by saturation mutagenesis, and the resulting mutants can be screened for the PSE activity described herein in order to identify mutants which retain PSE activity. After the mutagenesis of one of the sequences of SEQ ID NO:1, SEQ ID NO:3, SEQ ID NO:5, SEQ ID NO:7, SEQ ID NO:9 and SEQ ID NO:11, the encoded protein can be expressed recombinantly, and the activity of the protein can be determined, for example using the assay described herein (see examples section).

In addition to the nucleic acid molecules which encode the above described PSEs, a further aspect of the invention relates to isolated nucleic acid molecules which are "antisense" thereto. An "antisense" nucleic acid encompasses a nucleotide sequence which is complementary to a "sense" nucleic acid which encodes a protein, for example complementary to the coding strand of a double stranded cDNA molecule or complementary to an mRNA sequence. Accordingly, an antisense nucleic acid can bind to a sense nucleic acid via hydrogen bonds. The antisense nucleic acid can be complementary to a complete PSE-encoding strand or only to part thereof. In one embodiment, an antisense nucleic acid molecule is "antisense" to a "coding region" of the coding strand of a nucleotide sequence encoding a PSE. The term "coding region" refers to the region of the nucleotide sequence which encompasses codons which are translated into amino acid residues (for example the entire coding region which starts and ends with the stop codon, i.e. the last codon before the stop codon). In a further embodiment, the antisense nucleic acid molecule is "antisense" to a "noncoding region" of the coding strand of a nucleotide sequence encoding PSE. The term "noncoding strand" refers to 5' and 3' sequences which flank the coding region and are not translated into amino acids (i.e. which are also termed 5'- and 3'-untranslated regions).

Taking into consideration the PSE-encoding sequences disclosed herein of the coding strand (for example the sequences shown in SEQ ID NO:1, SEQ ID NO:3, SEQ ID NO:5, SEQ ID NO:7, SEQ ID NO:9 and SEQ ID NO:11), antisense nucleic acids according to the invention can be designed in accordance with the rules of the Watson Crick base pairing. The antisense nucleic acid molecule can be complementary to all of the coding region of PSE mRNA, but is more preferably an oligonucleotide which is "antisense" to only part of the coding or noncoding region of PSE mRNA. For example, the antisense oligonucleotide can be complementary to the region around the translation start of PSE mRNA. An antisense oligonucleotide can have a length of, for example, approximately 5, 10, 15, 20, 25, 30, 35, 40, 45 or 50 and more nucleotides. An antisense oligonucleotide is advantageously 15 to 25 nucleotides in length. An antisense nucleic acid according to the invention can be constructed by processes known in the art using chemical synthesis and enzymatic ligation reactions. For example, an antisense nucleic acid (for example an antisense oligonucleotide) can be synthesized chemically, making use of naturally occurring nucleotides or various modified nucleotides which are such that they increase the biological stability of the molecules or increase the physical stability of the duplex formed between the antisense and the sense nucleic acid; for example, phosphorothioate derivatives and acridin-substituted nucleotides may be used. Examples of modified nucleotides which may be used for generating the antisense nucleic acid are, inter alia, 5-fluorouracil, 5-bromouracil, 5-chlorouracil, 5-iodouracil, hypoxanthin, xanthin, 4-acetylcytosine, 5-(carboxyhydroxylmethyl)uracil, 5-carboxymethylaminomethyl 2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl 2-thiouracil, beta-D-mannosylqueosine, 5'-methoxycarboxymethyluracil, 5-methoxyuracil, 2-methylthio-N6-isopentyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, methyl uracil-5-oxyacetate, uracil-5-oxyacetic acid (v), 5-methyl 2-thiouracil, 3-(3-amino-3-N-2-carboxypropyl)uracil, (acp3)w and 2,6-diaminopurine. Alternatively, the antisense nucleic acid can be generated biologically using an expression vector to which a nucleic acid has been subcloned in antisense orientation (i.e. RNA which is transcribed by the nucleic acid introduced is in antisense orientation relative to a target nucleic acid of interest, which is described in greater detail in the subsection which follows).

The antisense nucleic acid molecules according to the invention are usually administered to a cell or generated in situ so that they hybridize with, or bind to, the cellular mRNA and/or the genomic DNA encoding a PSE, thus inhibiting expression of the protein, for example by inhibiting transcription and/or translation. Hybridization can be effected by conventional nucleotide complementarity with formation of a stable duplex or, for example in the case of an antisense nucleic acid molecule which binds DNA duplices, by specific interactions in the large cleft of the double helix. The antisense molecule can be modified in such a manner that it specifically binds to a receptor or to an antigen expressed at a selected cell surface, for example by binding the antisense nucleic acid molecule to a peptide or an antibody, each of which binds to a cell surface receptor or an antigen. The cells can also be provided with the antisense nucleic acid molecule using the vectors described herein. Vector constructs in which the antisense nucleic acid molecule is under the control of a strong prokaryotic, viral or eukaryotic promoter, inclusive of a plant promoter, are preferred for achieving sufficient intracellular concentrations of the antisense molecules.

In a further embodiment, the antisense nucleic acid molecule according to the invention is an α-anomeric nucleic acid molecule. An α-anomeric nucleic acid molecule forms specific double-stranded hybrids with complementary RNA, the strands running parallel to each other, in contrast to ordinary β-units [Gaultier et al. (1987) Nucleic Acids Res. 15:6625-6641]. Moreover, the antisense nucleic acid molecule can encompass a 2'-o-methylribonucleotide [Inoue et al. (1987) Nucleic Acids Res. 15:6131-6148] or a chimeric RNA DNA analogon [Inoue et al. (1987) FEBS Lett. 215:327-330].

In a further embodiment, an antisense nucleic acid according to the invention is a ribozyme. Ribozymes are catalytic RNA molecules with ribonuclease activity which can cleave a single-stranded nucleic acid, such as an mRNA, to which they have a complementary region. Thus, ribozymes, for example hammerhead ribozymes [described in Haselhoff and Gerlach (1988) Nature 334:585-591], can be used for the catalytic cleavage of PSE mRNA transcripts in order to inhibit the translation of PSE mRNA. A ribozyme with specificity for a PSE-encoding nucleic acid can be designed on the basis of the nucleotide sequence of a PSE cDNA disclosed herein (i.e. 38° C.k21_g07fwd in SEQ ID NO:1, SEQ ID NO:3, SEQ ID NO:5, SEQ ID NO:7, SEQ ID NO:9 and SEQ ID NO:11) or on the basis of a heterologous sequence to be isolated in accordance with the processes taught in the present invention. For example, a derivative of a Tetrahymena-L-19-IVS RNA can be constructed, in which the nucleotide sequence of the active site is complementary to the nucleotide sequence to be cleaved in PSE-encoding mRNA. See, for example, Cech et al., U.S. Pat. No. 4,987,071 and Cech et al., U.S. Pat. No. 5,116,742. As an alternative, PSE mRNA can be used for selecting a catalytic RNA with a specific ribonuclease activity from amongst a pool of RNA molecules [see, for example, Bartel, D., and Szostak, J. W. (1993) Science 261:1411-1418].

As an alternative, PSE gene expression can be inhibited by directing nucleotide sequences which are complementary to the regulatory region of a PSE nucleotide sequence (for example a PSE promoter and/or enhancer) in such a way that triple helix structures are formed, which inhibit the transcription of a PSE gene in target cells [see generally Helene, C. (1991) Anticancer Drug Res. 6(6) 569-84; Helene, C., et al. (1992) Ann. N.Y. Acad. Sci. 660:27-36; and Maher. L. J. (1992) Bioassays 14(12):807-815].

B. Gene Construct

A further embodiment of the invention is a novel gene construct comprising an isolated nucleic acid derived from *Physcomitrella, Phytophthora, Crypthecodinium* or *Thraustochytrium* and encodes a polypeptide which elongates $C_{16}$-, $C_{18}$- or $C_{20}$-fatty acids with at least two double bonds in the fatty acid by at least two carbon atoms, or which comprises the gene sequence of SEQ ID NO:1, SEQ ID NO:3, SEQ ID NO:5, SEQ ID NO:7, SEQ ID NO:9 and SEQ ID NO:11, its homologs, derivatives or analogs which are functionally linked to one or more regulatory signals, advantageously for increasing gene expression. Examples of these regulatory sequences are sequences which bind to inductors or repressors, and in this manner regulate the expression of the nucleic acid. In addition to these novel regulatory sequences, the natural regulation of these sequences before the actual structural genes may still be present and, if appropriate, have been genetically modified, so that the natural regulation has been switched off and the expression of the genes has been enhanced. However, the gene construct may also have a simpler structure, i.e. no additional regulatory signals have been inserted before the sequence SEQ ID NO:1, SEQ ID NO:3, SEQ ID NO:5, SEQ ID NO:7, SEQ ID NO:9 and SEQ ID NO:11 or their homologs and the natural promoter with its regulation has not been deleted. Instead, the natural regulatory sequence has been mutated in such a way that regulation no longer takes place and gene expression is enhanced. The gene construct may furthermore advantageously encompass one or more so-called enhancer sequences which are functionally linked to the promoter and which allow increased expression of the nucleic acid sequence. It is also possible additionally to insert advantageous sequences at the 3' end of the DNA sequences, for example further regulatory elements or terminators. The elongase genes may be present in one or more copies in the gene construct. It is advantageous for the insertion of further genes into organisms if further genes are present in the gene construct.

Advantageous regulation sequences for the novel process exist, for example, in promoters such as the cos, tac, trp, tet, trp-tet, lpp, lac, lpp-lac, lacIq, T7, T5, T3, gal, trc, ara, SP6, $\lambda\text{-}P_R$ or $\lambda\text{-}P_L$ promoter and are advantageously used in Gram-negative bacteria. Further advantageous regulatory sequences exist, for example, in Grampositive promoters amy and SPO2, in the yeast or fungal promoters ADC1, MFa, AC, P-60, CYCl, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzylsulfonamide inducible), Plant J. 2, 1992:397-404

(Gatz et al., tetracyclin-inducible), EP-A-0 335 528 (abscisic acid-inducible) or WO 93/21334 (ethanol- or cyclohexenol-inducible). Other suitable plant promoters are the cytosolic FBPase or the potato ST-LSI promoter (Stockhaus et al., EMBO J. 8, 1989, 2445), the *Glycine max* phosphoribosylpyrophosphate amidotransferase promoter (Genbank Accession No. U87999) or the node-specific promoter described in EP-A-0 249 676. Especially advantageous promoters are promoters which allow expression in tissues which are involved in fatty acid biosynthesis. Very especially advantageous are seed-specific promoters, such as the usp, the LEB4, the phaseolin or the napin promoter. Further especially advantageous promoters are seed-specific promoters which can be used for monocots or dicots which are described in U.S. Pat. No. 5,608,152 (oilseed rape napin promoter), WO 98/45461 (Arabidopsis phaseolin promoter), U.S. Pat. No. 5,504,200 (*Phaseolus vulgaris* phaseolin promoter), WO 91/13980 (Brassica Bce4-promoter), Baeumlein et al., Plant J., 2, 2, 1992:233-239 (leguminous LEB4 promoter), these promoters being suitable for dicots. The following promoters are suitable, for example, for monocots: the barley lpt-2 or lpt-1 promoter (WO 95/15389 and WO 95/23230), the barley hordein promoter, and other suitable promoters described in WO 99/16890.

In principle, it is possible to use all natural promoters with their regulatory sequences, such as those mentioned above, for the novel process. It is also possible and advantageous additionally to use synthetic promoters.

As described above, the gene construct can also encompass further genes which are to be introduced into the organisms. It is possible and advantageous to introduce into the host organisms, and to express therein, regulatory genes such as genes for inductors, repressors or enzymes which, owing to their enzymatic activity, engage in the regulation of one or more genes of a biosynthetic pathway. These genes can be of heterologous or homologous origin. The inserted genes can have their own promoter or else be under the control of the promoter of sequence SEQ ID NO:1, SEQ ID NO:3, SEQ ID NO:5, SEQ ID NO:7, SEQ ID NO:9 and SEQ ID NO:11 or its homologs, derivatives or analogs.

To express the other genes which are present, the gene construct advantageously encompasses further 3'- and/or 5'-terminal regulatory sequences for enhancing expression, and these are selected for optimal expression as a function of the host organism chosen and the gene(s).

As mentioned above, these regulatory sequences are intended to make possible the specific expression of the genes and protein expression. Depending on the host organism, this may mean, for example, that the gene is expressed or overexpressed only after induction, or that it is expressed and/or overexpressed immediately.

Moreover, the regulatory sequences or regulatory factors can preferably have an advantageous effect on the expression of the genes which have been introduced, thus enhancing it. In this manner, it is possible that the regulatory elements are advantageously enhanced at the transcriptional level, using strong transcription signals, such as promoters and/or enhancers. However, it is furthermore also possible to enhance translation, for example by improving mRNA stability. The nucleic acid sequences according to the invention are advantageously cloned into a gene construct (=expression cassette, nucleic acid construct) together with at least one reporter gene, and this gene construct is introduced into the organism via a vector or directly into the genome. This reporter gene should allow easy detectability by means of a growth, fluorescence, chemoluminescence, bioluminescence or resistance assay or via photometric measurement. Examples of reporter genes which may be mentioned are genes for resistance to antibiotics or herbicides, hydrolase genes, fluorescence protein genes, bioluminescence genes, sugar or nucleotide metabolism genes or biosynthesis genes such as the Ura3 gene, the Ilv2 gene, the luciferase gene, the β-galactosidase gene, the gfp gene, the 2-deoxyglucose-6-phosphate phosphatase gene, the β-glucuronidase gene, the β-lactamase gene, the neomycin phosphotransferase gene, the hygromycin phosphotransferase gene or the BASTA (=glufosinate resistance) gene. These genes make it possible for the transcriptional activity, and thus gene expression, to be measured and quantified readily. This allows the identification of positions in the genome which show different productivity.

The nucleic acid sequences according to the invention with SEQ ID NO:1, SEQ ID NO:3, SEQ ID NO:5, SEQ ID NO:7, SEQ ID NO:9 and SEQ ID NO:11, which encode elongases, can be present in the expression cassette (=gene construct) in one or more copies.

The expression cassette (=gene construct, nucleic acid construct) can additionally comprise at least one further nucleic acid which encodes a gene, preferably from fatty acid biosynthesis, to be introduced into the host organisms. These genes can be under separate regulation or under the same regulatory region as the genes for the elongase according to the invention. These genes are, for example, further biosynthesis genes, advantageously of fatty acid biosynthesis, which make possible an increased synthesis. Genes which may be mentioned by way of example are those for Δ19-, Δ17-, Δ15-, Δ12-, Δ9-, Δ8-, Δ6-, Δ5-, Δ4-desaturase, the various hydroxylases, Δ12-acetylenase, acyl-ACP thioesterases, β-ketoacyl-ACP synthases or β-ketoacyl-ACP reductases. The desaturase genes are advantageously used in the nucleic acid construct. Again, these genes may be present in the gene construct in one or more copies.

C. Recombinant Expression Vectors and Host Cells

A further aspect of the invention relates to vectors, preferably expression vectors, comprising a nucleic acid according to the invention or a gene construct according to the invention which encode a PSE (or part thereof). As used in the present context, the term "vector" refers to a nucleic acid molecule which can transport another nucleic acid to which it is bound. One type of vector is a "plasmid", which represents a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial origin of replication and episomal mammalian vectors). Other vectors (for example nonepisomal mammalian vectors) are integrated into the genome of a host cell upon introduction into the host cell and so replicate together with the host genome. In addition, certain vectors can govern the expression of genes to which they are functionally linked. These vectors are referred to as "expression vectors" herein. Usually, expression vectors which are suitable for recombinant DNA techniques take the form of plasmids. In the present description, "plasmid" and "vector" may be used interchangeably since the plasmid is the most frequently used form of a vector. However, the invention is intended to encompass these other forms of expression vectors, such as viral vectors (for example replication deficient retroviruses, adenoviruses and adeno-related viruses) which exert similar functions. Furthermore, the term vector is also intended to encompass other vectors known to the skilled worker, such as phages, viruses such as SV40, CMV, baculovirus, adenovirus, transposons, IS elements, phasmids, phagemids, cosmids, linear or circular DNA and RNA.

The recombinant expression vectors according to the invention encompass a nucleic acid according to the invention or a gene construct according to the invention in a form which is suitable for expressing the nucleic acid in a host cell, which means that the recombinant expression vectors encompass one or more regulatory sequences, selected on the basis of the host cells to be used for expression, which is or are functionally linked to the nucleic acid sequence to be expressed. In a recombinant expression vector, "functionally linked" means that the nucleotide sequence of interest is bound to the regulatory sequence(s) in such a way that expression of the nucleotide sequence is possible and they are bound to each other so that both sequences fulfill the predicted function which has been ascribed to the sequence (for example in an in-vitro transcription/translation system or in a host cell, when the vector is introduced into the host cell). The term "regulatory sequence" is intended to encompass promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnology, CRC Press, Boca Raton, Fla., Ed.: Glick and Thompson, Chapter 7, 89-108, including the references therein. Regulatory sequences encompass those which control the constitutive expression of a nucleotide sequence in many types of host cell and those which control the direct expression of the nucleotide sequence only in certain host cells under certain conditions. The skilled worker knows that the design of the expression vector may depend on factors such as the choice of the host cell to be transformed, the extent to which the desired protein is expressed, and the like. The expression vectors according to the invention can be introduced into host cells in order to produce proteins or peptides, including fusion proteins or fusion peptides, which are encoded by the nucleic acids as described herein (for example PSEs, mutant forms of PSEs, fusion proteins and the like).

The recombinant expression vectors according to the invention can be designed for expressing PSEs in prokaryotic or eukaryotic cells. For example, PSE genes can be expressed in bacterial cells, such as *C. glutamicum*, insect cells (using baculovirus expression vectors), yeast and other fungal cells [see Romanos, M. A., et al. (1992) "Foreign gene expression in yeast: a review", Yeast 8:423-488; van den Hondel, C.A.M.J.J., et al. (1991) "Heterologous gene expression in filamentous fungi", in: More Gene Manipulations in Fungi, J. W. Bennet & L. L. Lasure, Ed., pp. 396-428: Academic Press: San Diego; and van den Hondel, C.A.M.J.J., & Punt, P. J. (1991) "Gene transfer systems and vector development for filamentous fungi, in: Applied Molecular Genetics of Fungi, Peberdy, J. F., et al., Ed., pp. 1-28, Cambridge University Press: Cambridge], algae [Falciatore et al., 1999, Marine Biotechnology. 1, 3:239-251], ciliates of the following types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella* and *Stylonychia*, in particular of the genus *Stylonychia lemnae*, using vectors and following a transformation method as described in WO 98/01572, and cells of multicelled plants [see Schmidt, R. and Willmitzer, L. (1988) "High efficiency *Agrobacterium tumefaciens*-mediated transformation of *Arabidopsis thaliana* leaf and cotyledon explants" Plant Cell Rep.:583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Bd. 1, Engineering and Utilization, Ed.: Kung and R. Wu, Academic Press (1993), 128-43; Potrykus, Annu. Rev. Plant Physiol. Plant Molec. Biol. 42 (1991), 205-225 (and references cited therein)] or mammalian cells. Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7 promoter regulatory sequences and T7 polymerase.

In prokaryotes, proteins are usually expressed with vectors containing constitutive or inducible promoters which control the expression of fusion proteins or nonfusion proteins. Fusion vectors add a series of amino acids to a protein encoded therein, usually at the amino terminus of the recombinant protein, but also at the C terminus or fused within suitable regions in the proteins. These fusion vectors usually have three tasks: 1) to enhance the expression of recombinant protein; 2) to increase the solubility of the recombinant protein and 3) to support the purification of the recombinant protein by acting as ligand in affinity purification, for example via so-called his tags. In the case of fusion expression vectors, a proteolytic cleavage site is frequently introduced at the site where the fusion unit and the recombinant protein are linked, so that the recombinant protein can be separated from the fusion unit after purification of the fusion protein. These enzymes and their corresponding recognition sequences encompass factor Xa, thrombin and enterokinase.

Typical fusion expression vectors are, inter alia, pGEX [Pharmacia Biotech Inc; Smith, D. B., and Johnson, K. S. (1988) Gene 67:31-40], pMAL [New England Biolabs, Beverly, Mass.] and pRIT5 [Pharmacia, Piscataway, N.J.], where glutathione S-transferase (GST), maltose-E-binding protein or protein A is fused to the recombinant target protein. In one embodiment, the PSE-encoding sequence is cloned into a pGEX expression vector to generate a vector encoding a fusion protein which encompasses, from the N terminus to the C terminus, GST-thrombin cleavage site-X-protein. The fusion protein can be purified by affinity chromatography using glutathione-agarose resin. Recombinant PSE which is not fused with GST can be obtained by cleaving the fusion protein with thrombin.

Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). Target gene expression of the pTrc vector is based on transcription by host RNA polymerase from a hybrid trp-lac fusion promoter. Target gene expression from the pET 11d vector is based on transcription from a T7-gn10-lac fusion promoter which is mediated by a coexpressed viral RNA polymerase (T7 gn1). This viral polymerase is provided by the host strains BL21 (DE3) or HMS174 (DE3) by a resident λ prophage which harbors a T7 gn1 gene under the transcriptional control of the lacUV 5 promoter.

Other vectors which are suitable for use in prokaryotic organisms are known to the skilled worker; these vectors are, for example, in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III$^{113}$-B1, pgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

A strategy of maximizing the expression of recombinant protein is to express the protein in a host bacterium whose ability to cleave the recombinant protein proteolytically is disrupted [Gottesman, S., Gene Expression Technology Methods in Enzymology 185, Academic Press, San Diego, Calif. (1990) 119-128]. A further strategy is to modify the nucleic acid sequence of the nucleic acid to be inserted into an expression vector, so that the individual codons for each amino acid are those which are preferentially used in a bacterium selected for expression, such as C. glutamicum [Wada et al. (1992) Nucleic Acids Res. 20:2111-2118]. Modification of these nucleic acid sequences according to the invention is carried out by standard techniques of DNA synthesis.

In a further embodiment, the PSE expression vector is a yeast expression vector. Examples of vectors for expression in the yeast S. cerevisiae include pYepSec1 [Baldari et al. (1987) Embo J. 6:229-234], pMFa [Kurjan and Herskowitz (1982) Cell 30:933-943], pJRY88 [Schultz et al. (1987) Gene 54:113-123] and pYES2 [Invitrogen Corporation, San Diego, Calif.]. Vectors and methods for the construction of vectors which are suitable for use in other fungi, such as the filamentous fungi, include those which are described in detail in: van den Hondel, C.A.M.J.J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Ed., pp. 396-428: Academic Press: San Diego]. Further suitable-yeast vectors are, for example, pAG-1, YEp6, YEp13 or pEMBLYe23.

As an alternative, the PSEs according to the invention can be expressed in insect cells using baculovirus expression vectors. Baculovirus vectors which are available for expressing proteins in cultured insect cells (for example Sf9 cells) include the pAc series [Smith et al. (1983) Mol. Cell Biol. 3:2156-2165] and the pVL series [Lucklow and Summers (1989) Virology 170:31-39].

The abovementioned vectors are just a short review of suitable vectors which are possible. Further plasmids are known to the skilled worker and are described, for example, in: Cloning Vectors (Ed. Pouwels, P. H., et al., Elsevier, Amsterdam-New York-Oxford, 1985, ISBN 0 444 904018).

In yet a further embodiment, a nucleic acid according to the invention is expressed in mammalian cells using a mammalian expression vector. Examples of mammalian expression vectors include pCDM8 [Seed, B. (1987) Nature 329:840] and pMT2PC [Kaufman et al. (1987) EMBO J. 6:187-195]. When used in mammalian cells, the control functions of the expression vector are frequently provided by viral regulatory elements. Promoters which are usually used are derived, for example, from polyoma, adenovirus2, cytomegalovirus and simian virus 40. Other suitable expression systems for prokaryotic and eukaryotic cells can be found in Chapters 16 and 17 of Sambrook, J., Fritsch, E. F., and Maniatis, T., Molecular Cloning: A Laboratory Manual, 2nd Edition, Cold Spring Harbor Laboratory, Cold Spring Harbor Laboratory Press, Cold Spring Harbor, N.Y., 1989.

In another embodiment, the recombinant mammalian expression vector can control the expression of the nucleic acid preferably in a specific cell type (for example, tissue-specific regulatory elements are used for expressing the nucleic acid). Tissue-specific regulatory elements are known in the art. Nonlimiting examples of suitable tissue-specific promoters are, inter alia, the albumin promoter [liverspecific; Pinkert et al. (1987) Genes Dev. 1:268-277], lymphoid-specific promoters [Calame and Eaton (1988) Adv. Immunol. 43:235-275], in particular promoters of T-cell receptors [Winoto and Baltimore (1989) EMBO J. 8:729-733] and immunoglobulins [Banerji et al. (1983) Cell 33:729-740; Queen and Baltimore (1983) Cell 33:741-748], neuron-specific promoters [for example neurofilament promoter; Byrne and Ruddle (1989) PNAS 86:5473-5477], pancreas-specific promoters [Edlund et al., (1985) Science 230:912-916] and mamma-specific promoters [for example milk serum promoter; U.S. Pat. No. 4,873,316 and EP-A-0 264 166). Also included are development-regulated promoters, for example the mouse hox promoters [Kessel and Gruss (1990) Science 249:374-379] and the fetoprotein promoter [Campes and Tilghman (1989) Genes Dev. 3:537-546].

In a further embodiment, the PSEs according to the invention can be expressed in single celled plant cells (such as algae), see Falciatore et al., 1999, Marine Biotechnology 1 (3):239-251 and references cited therein, and in plant cells from higher plants (for example spermatophytes such as crops). Examples of plant expression vectors include those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary Agrobacterium vectors for plant transformation", Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, pp. 15-38. Further suitable plant vectors are described, inter alia, in "Methods in Plant Molecular Biology and Biotechnology" (CRC Press), Chapter 6/7, pp. 71-119. Advantageous vectors are so-called shuttle vectors or binary vectors, which replicate in E. coli and Agrobacterium.

A plant expression cassette preferably comprises regulatory sequences which can control gene expression in plant cells and which are functionally linked, so that each sequence can fulfill its function, such as transcriptional termination, for example polyadenylation signals. Preferred polyadenylation signals are those derived from Agrobacterium tumefaciens T-DNA, such as gene 3 of the Ti plasmid pTiACH5, which is known as octopine synthase [Gielen et al., EMBO J. 3 (1984) 835 et seq.] or functional equivalents thereof, but all other terminators which are functionally active in plants are also suitable.

Since plant gene expression is very frequently not limited to the transcriptional level, a plant expression cassette preferably comprises other functionally linked sequences, such as translation enhancers, for example the overdrive sequence, which contains the 5'-untranslated tobacco mosaic virus leader sequence, which increases the protein/RNA ratio [Gallie et al., 1987, Nucl. Acids Research 15:8693-8711].

Plant gene expression must be functionally linked to a suitable promoter which effects gene expression in a cell- or tissue-specific manner with the correct timing. Preferred promoters are those which lead to constitutive expression [Benfey et al., EMBO J. 8 (1989) 2195-2202], such as those which are derived from plant viruses such as 35S CAMV [Franck et al., Cell 21 (1980) 285-294], 19S CaMV (see also U.S. Pat. No. 5,352,605 and WO 84/02913) or plant promoters such as the Rubisco small subunit promoter described in U.S. Pat. No. 4,962,028.

Other sequences which are preferred for use for functional linkage in plant gene expression cassettes are targeting sequences, which are required for targeting the gene product in its corresponding cell compartment [for a review, see Kermode, Crit. Rev. Plant Sci. 15, 4 (1996) 285-423 and references cited therein], for example into the vacuole, the nucleus, all types of plastids such as amyloplasts, chloroplasts, chromoplasts, the extracellular space, the mitochondria, the endoplasmatic reticulum, elaioplasts, peroxisomes and other compartments of plant cells.

Plant gene expression can also be facilitated via a chemically inducible promoter [for a review, see Gatz 1997, Annu. Rev. Plant Physiol. Plant Mol. Biol., 48:89-108]. Chemically inducible promoters are particularly suitable when it is desired for gene expression to take place in a specific manner with regard to timing. Examples of such promoters are a salicylic acid-inducible promoter (WO 95/19443), a tetracyclin-inducible promoter [Gatz et al. (1992) Plant J. 2, 397-404] and an ethanol-inducible promoter.

Other suitable promoters are promoters which respond to biotic or abiotic stress conditions, for example the pathogen-induced PRP1 gene promoter [Ward et al., Plant. Mol. Biol. 22 (1993) 361-366], the heat-inducible totomato hsp80 promoter (U.S. Pat. No. 5,187,267), the low-temperature-inducible potato alpha amylase promoter (WO 96/12814) or the wound-inducible pinII promoter (EP-A-0 375 091).

Promoters which are particularly preferred are those which lead to gene expression in tissues and organs in which lipid and oil biosynthesis take place, in seed cells such as endosperm cells and cells of the developing embryo. Promoters which are suitable are the oilseed rape napin gene promoter (U.S. Pat. No. 5,608,152), the *Vicia faba* USP promoter [Baeumlein et al., Mol Gen Genet, 1991, 225 (3):459-67], the *Arabidopsis oleosin* promoter (WO 98/45461), the *Phaseolus vulgaris* phaseolin promoter (U.S. Pat. No. 5,504,200), the *Brassica* Bce4 promoter (WO 91/13980) or the legumin B4 promoter [LeB4; Baeumlein et al., 1992, Plant Journal, 2 (2):233-9], and promoters which lead to the seed-specific ex pression in monocots such as maize, barley, wheat, rye, rice and the like. Notable promoters which are suitable are the barley lpt2 or lpt1 gene promoter (WO 95/15389 and WO 95/23230), or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, and the rye secalin gene).

Promoters which are also particularly suitable are those which lead to plastid-specific expression, since plastids are the compartment in which the precursors and some end products of lipid biosynthesis are synthesized. Suitable promoters such as the viral RNA polymerase promoter are described in WO 95/16783 and WO 97/06250, and the *Arabidopsis* clpP promoter, described in WO 99/46394.

The invention furthermore provides a recombinant expression vector encompassing a DNA molecule according to the invention which is cloned into the expression vector in anti-sense orientation, i.e. the DNA molecule is functionally linked to a regulatory sequence in such a way that it allows the expression (by transcribing the DNA molecule) of an RNA molecule which is "antisense" to the PSE mRNA. Regulatory sequences may be selected which are functionally linked to a nucleic acid cloned in antisense orientation and which control the continuous expression of the antisense RNA molecule in a multiplicity of cell types, for example, viral promoters and/or enhancers or regulatory sequences may be selected which control the constitutive, tissue-specific or cell type-specific expression of antisense RNA. The antisense expression vector may be present in the form of a recombinant plasmid, phagemid or attenuated virus in which the antisense nucleic acids are produced under the control of a highly effective regulatory region whose activity can be determined by the cell type into which the vector has been introduced. For an explanation of the regulation of gene expression by means of antisense genes, see Weintraub, H., et al., Antisense-RNA as a molecular tool for genetic analysis, Reviews—Trends in Genetics, Vol. 1(1) 1986.

A further aspect of the invention relates to host cells into which a recombinant expression vector according to the invention has been introduced. The terms "host cell" and "recombinant host cell" are used interchangeably in the present context. Naturally, these terms do not only refer to the particular target cell, but also to the progeny or potential progeny of this cell. Since specific modifications may occur in subsequent generations owing to mutation or environmental effects, this progeny is not necessarily identical with the parental cell, but remains within the scope of the term as used in the present context.

A host cell may be a prokaryotic or eukaryotic cell. For example, a PSE can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms, such as *C. glutamicum*. Other suitable host cells are known to the skilled worker.

Vector DNA can be introduced into prokaryotic or eukaryotic cells via conventional transformation or transfection techniques. The terms "transformation" and "transfection", conjugation and transduction as used in the present context are intended to encompass a multiplicity of methods known in the art for introducing foreign nucleic acid (for example DNA) into a host cell, including calcium phosphate or calcium chloride coprecipitation, DEAE dextran mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd Ed., Cold Spring Harbor Laboratory, Cold Spring Harbor Laboratory Press, Cold Spring Harbor, N.Y., 1989) and other laboratory textbooks, such as Methods in Molecular Biology, 1995, Vol. 44, *Agrobacterium* protocols, Ed.: Gartland and Davey, Humana Press, Totowa, N.J.

It is known about the stable transfection of mammalian cells that only a minority of the cells integrate the foreign DNA into their genome, depending on the expression vector used and the transfection technique used. To identify and select these integrants, a gene which encodes a selectable marker (for example resistance to antibiotics) is usually introduced into the host cells together with the gene of interest. Preferred selectable markers encompass those which impart resistance to drugs such as G418, hygromycin and methotrexate, or, in plants, those which impart resistance to a herbicide such as glyphosphate or glufosinate. Further suitable markers are, for example, markers which encode genes which are involved in the biosynthesis pathways of, for example, sugars or amino acids, such as β-galactosidase, ura3 or ilv2. Markers which encode genes such as luciferase, gfp or other fluorescence genes are also suitable. These markers can be used in mutants in which these genes are not functional since they have been deleted for example by means of conventional methods. Furthermore, markers which encode a nucleic acid which encodes a selectable marker can be introduced into a host cell on the same vector as the one which encodes a PSE, or can be introduced on a separate vector. Cells which have been transfected stably with the nucleic acid introduced can be identified for example by drug selection (for example, cells which have the selectable marker integrated survive, whereupon other cells die).

To generate a homologously recombinant microorganism, a vector is generated which contains at least one segment of a PSE gene into which a deletion, addition or substitution has been introduced in order to modify the PSE gene hereby, for example to functionally disrupt it. This PSE gene is preferably a *Physcomitrella, Phytophthora, Crypthecodinium* or *Thraustochytrium* PSE gene, but a homolog or analog from other organisms, even from a mammalian, fungal or insect source, can also be used. In a preferred embodiment, the vector is designed in such a way that the endogenous PSE gene is functionally disrupted (i.e. no longer encodes a functional protein, also termed knock-out vector) upon homologous recombination. As an alternative, the vector can be designed such that the endogenous PSE gene mutates or is modified otherwise upon homologous recombination while still encoding a functional protein (for example, the upstream regulatory region can be modified in such a way that this leads to a modification of the expression of the endogenous PSE). To generate a point mutation via homologous recombination, DNA-RNA hybrids, which are also known as chimeraplasty and which are known from Cole-Strauss et al., 1999, Nucleic Acids Research 27(5):1323-1330 and Kmiec, Gene therapy, 1999, American Scientist, 87(3):240-247 can also be used.

In the vector for homologous recombination, the modified segment of the PSE gene is flanked at its 5' and 3' end by additional nucleic acid of the PSE gene, so that homologous recombination is possible between the exogenous PSE gene which is present on the vector and an endogenous PSE gene in a microorganism or a plant. The additional flanking PSE nucleic acid is sufficiently long for successful homologous recombination with the endogenous gene. Usually, several hundred base pairs up to kilobases of flanking DNA (both on the 5' and on the 3' end) are present in the vector [for a description of vectors for homologous recombination, see, for example, Thomas, K. R., and Capecchi, M. R. (1987) Cell 51:503 or for the recombination in *Physcomitrella patens* on cDNA basis, see Strepp et al., 1998, Proc. Natl. Acad. Sci. USA 95 (8):4368-4373]. The vector is introduced into a microorganism or plant cell (for example by means of polyethylene glycol-mediated DNA), and cells in which the PSE gene introduced has undergone homologous recombination with the endogenous PSE gene are selected using techniques known in the art.

In another embodiment, recombinant organisms such as microorganisms of the plants can be generated which contain selected systems which allow regulated expression of the gene introduced. The inclusion of a PSE gene in a vector, where it is placed under the control of the lac-operon, allows, for example, expression of the PSE gene only in the presence of IPTG. These regulatory systems are known in the art.

A host cell according to the invention, such as prokaryotic or eukaryotic host cells, growing either in culture or in a field, can be used for producing (i.e. expressing) a PSE. In plants, an alternative method can additionally be used by directly transferring DNA into developing flowers via electroporation or *Agrobacterium* mediated gene transfer. Accordingly, the invention furthermore provides methods of producing PSEs using the host cells according to the invention. In one embodiment, the method encompasses growing the host cell according to the invention (into which a recombinant expression vector encoding a PSE has been introduced or into whose genome a gene encoding a wild-type or modified PSE has been introduced) in a suitable medium until the PSE has been produced. In a further embodiment, the method encompasses isolating the PSEs from the medium or the host cell.

Host cells which are suitable in principle for taking up the nucleic acid according to the invention, the novel gene product according to the invention or the vector according to the invention are all prokaryotic or eukaryotic organisms. The host organisms which are used advantageously are organisms such as bacteria, fungi, yeasts, animal cells or plant cells. Further advantageous organisms are animals or, preferably, plants or parts thereof. The term "animal" is understood here as not including humans. Fungi, yeasts or plants are preferably used, especially preferably fungi or plants, very especially preferably plants such as oil crops which contain large amounts of lipid compounds, such as oilseed rape, evening primrose, castor oil plant, canola, peanut, linseed, soya, safflower, sunflower, borage, oil palm, coconut or plants such as maize, wheat, rye, oats, triticale, rice, barley, cotton, cassava, pepper, tagetes, Solanaceae plants such as potato, tobacco, aubergine and tomato, *Vicia* species, pea, alfalfa, shrub plants, (coffee, cacao, tea), *Salix* species, trees (oil palm, coconut) and perennial grasses and fodder crops. Especially preferred plants according to the invention are oil crops such as soya, peanut, oilseed rape, canola, castor oil plant, linseed, evening primrose, sunflower, safflower, trees (oil palm, coconut).

A particularly preferred aspect of the invention relates to a plant cell which comprises the polynucleotide according to the invention or the vector according to the invention. Preference is furthermore given to transgenic plants or plant tissue comprising the plant cell according to the invention. A further aspect of the present invention relates to those parts of the plants according to the invention which can be harvested and to the material suitable for propagating the transgenic plants according to the invention, containing either plant cells according to the invention which express the nucleic acid according to the invention or containing cells which have an elevated level of the protein according to the invention. In principle, all parts of a plant can be harvested, in particular flowers, pollen, fruits, seedlings, roots, leaves, seeds, tubers, stems, etc. Propagation material includes, for example, seeds, fruits, seedlings, tubers, cuttings and rhizomes.

D. Isolated PSE

A further aspect of the invention relates to isolated PSEs and biologically active parts thereof. An "isolated" or "purified" protein or a biologically active part thereof, is essentially free of cellular material when it is produced by recombinant DNA techniques, or free of chemical precursors or other chemicals when it is synthesized chemically. The term "essentially free of cellular material" encompasses PSE preparations in which the protein is separate from cellular components of the cells in which it is produced naturally or recombinantly. In one embodiment, the term "essentially free of cellular material" encompasses PSE preparations with less than approximately 30% (based on the dry weight) of non-PSE (also referred to herein as "contaminating protein"), more preferably less than approximately 20% of non-PSE, even more preferably less than approximately 10% of non-PSE and most preferably less than approximately 5% of non-PSE. When the PSE or a biologically active part thereof has been produced by recombinant technology, it is also essentially free of culture medium, i.e. the culture medium amounts to less than approximately 20%, more preferably less than approximately 10% and most preferably less than approximately 5% of the volume of the protein preparation. The term "essentially free of chemical precursors or other chemicals" encompasses PSE preparations in which the protein is separate from chemical precursors or other chemicals which are involved in the synthesis of the protein. In one embodiment, the term "essentially free of chemical precursors or other chemicals" encompasses PSE preparations with less than approximately 30% (based on the dry weight) of chemical precursors or non-PSE chemicals, more preferably less than approximately 20% of chemical precursors or non-PSE chemicals, even more preferably less than approximately 10% of chemical precursors or non-PSE chemicals and most preferably less than approximately 5% of chemical precursors or non-PSE chemicals. In preferred embodiments, isolated proteins or biologically active parts thereof exhibit no contaminating proteins from the same organism from which the PSE originates. In the case of the protein according to the invention which contains the sequence shown in SEQ ID NO: 10 or which is encoded by a gene which comprises SEQ ID NO: 9, however, it has to be taken into account that the sequence starts with two Met. In the translation of a corresponding encoding nucleic acid sequence, this may result in the expression of two derivatives of the protein according to the invention starting with the first or the second Met. The expression ratio between the two derivatives can vary between 0 and 1, depending on the type of expression or the host organism. The invention accordingly comprises PSE containing both of the derivatives mentioned, or only one of the derivatives. The two derivatives can have different activities, localizations, half-lives, regulation mechanisms, etc. These proteins are usually produced by recombinant expression, for example *Physcomitrella, Phytophthora, Cryptthecodinium* or *Thraustochytrium* PSE in plants such as *Physcomitrella patens* or the abovementioned, or microorganisms for example bacteria such as *E. coli, Bacillus subtilis, C. glutamicum*, fungi such as *Mortierella*, yeast such as *Saccharomyces*, or ciliates such as *Colpidium* or algae such as *Phaeodactylum*.

An isolated PSE according to the invention or part thereof can also participate in the metabolism of compounds required for the synthesis of cell membranes in *Physcomitrella, Phytophthora, Crypthecodinium* or *Thraustochytrium* or in the transport of molecules via these membranes. In preferred embodiments, the protein or the part thereof encompasses an amino acid sequence which has sufficient homology with an amino acid sequence of SEQ ID NO:2, SEQ ID NO:4, SEQ ID NO:6, SEQ ID NO:8, SEQ ID NO:10 and SEQ ID NO:12 for the protein or the part thereof to retain the ability to participate in the metabolism of compounds required for the synthesis of cell membranes in *Physcomitrella, Phytophthora, Crypthecodinium* or *Thraustochytrium* or in the transport of molecules via these membranes. The part of the protein is preferably a biologically active part as described herein. In a further preferred embodiment, a PSE according to the invention has one of the amino acid sequences shown in SEQ ID NO:2, SEQ ID NO:4, SEQ ID NO:6, SEQ ID NO:8, SEQ ID NO:10 and SEQ ID NO:12. In a further preferred embodiment, the PSE has an amino acid sequence which is encoded by a nucleotide sequence which hybridizes with a nucleotide sequence of SEQ ID NO:1, SEQ ID NO:3, SEQ ID NO:5, SEQ ID NO:7, SEQ ID NO:9 and SEQ ID NO:11, for example under stringent conditions. In yet another preferred embodiment, the PSE has an amino acid sequence encoded by a nucleotide sequence which has at least approximately 50 to 60%, preferably at least approximately 60 to 70%, more preferably at least approximately 70 to 80%, 80 to 90%, 90 to 95% and more preferably at least approximately 96%, 97%, 98%, 99% or more homology with one of the amino acid sequences of SEQ ID NO:2, SEQ ID NO:4, SEQ ID NO:6, SEQ ID NO:8, SEQ ID NO:10 and SEQ ID NO:12. The PSE preferred in accordance with the invention preferably also has at least one of the PSE activities described herein. For example, a preferred PSE according to the invention encompasses an amino acid sequence encoded by a nucleotide sequence which hybridizes with a nucleotide sequence of SEQ ID NO:1, SEQ ID NO:3, SEQ ID NO:5, SEQ ID NO:7, SEQ ID NO:9 and SEQ ID NO:11, for example under stringent conditions, and which can participate in the metabolism of compounds required for the synthesis of cell membranes in *Physcomitrella, Phytophthora, Crypthecodinium* or *Thraustochytrium* or in the transport of molecules via these membranes and is capable of elongating one or more polyunsaturated fatty acids with at least two double bonds and a chain length of $C_{16}$ or $C_{18}$.

In other embodiments, the PSE is essentially homologous with an amino acid sequence of SEQ ID NO:2, SEQ ID NO:4, SEQ ID NO:6, SEQ ID NO:8, SEQ ID NO:10 and SEQ ID NO:12 and retains the functional activity of the protein of one of the sequences of SEQ ID NO:2, SEQ ID NO:4, SEQ ID NO:6, SEQ ID NO:8, SEQ ID NO:10 and SEQ ID NO:12, their amino acid sequence differs, owing to natural variation or mutagenesis as described in detail in the above subsection I. In a further embodiment, the PSE is, accordingly, a protein encompassing an amino acid sequence which has at least approximately 50 to 60%, preferably at least approximately 60 to 70% and more preferably at least approximately 70 to 80%, 80 to 90%, 90 to 95% and most preferably at least approximately 96%, 97%, 98%, 99% or more homology with a complete amino acid sequence of SEQ ID NO:2, SEQ ID NO:4, SEQ ID NO:6, SEQ ID NO:8, SEQ ID NO and SEQ ID NO:12 and has at least one of the PSE activities described herein. In another embodiment, the invention relates to a complete *Physcomitrella, Phytophthora, Crypthecodinium* or *Thraustochytrium* protein which is essentially homologous with a complete amino acid sequence of SEQ ID NO:2, SEQ ID NO:4, SEQ ID NO:6, SEQ ID NO:8, SEQ ID NO:10 and SEQ ID NO:12.

Biologically active parts of a PSE encompass peptides encompassing amino acid sequences derived from the amino acid sequence of a PSE, for example an amino acid sequence shown in SEQ ID NO:2, SEQ ID NO:4, SEQ ID NO:6, SEQ ID NO:8, SEQ ID NO:10 and SEQ ID NO:12 or the amino acid sequence of a protein which is homologous with a PSE, which peptides have fewer amino acids than the full length PSE or the full-length protein which is homologous with a PSE and have at least one activity of a PSE. Biologically active parts (peptides, for example peptides with a length of, for example, 5, 10, 15, 20, 30, 35, 36, 37, 38, 39, 40, 50, 100 or more amino acids) usually encompass a domain or a motif with at least one activity of a PSE. Moreover, other biologically active parts in which other regions of the protein are deleted can be generated by recombinant techniques and studied with regard to one or more of the activities described herein. The biologically active parts of a PSE preferably encompass one or more selected domains/motifs or parts thereof with biological activity.

Some of such domains and motifs can be identified by sequence analysis, for example using computer aided methods.

The sequences according to the invention were found to contain, for example, KK motifs.

Kermode 1996, Critical Reviews in Plant Sciences 15 (4): 285-423, describes KK motifs, a double lysine, which is found mainly as KKXX or K X K XXX motif and which influences recycling from the ER to the Golgi apparatus and thus the residence time of the protein and its enzyme activity at a certain location, in particular the ER.

Double lysine motifs have also been found, for example in Δ12-desaturases (Arondel et al. 1992, Science 258:1353), and they are also present in the elongases according to the invention. In particular motifs which can be localized at the C-terminus have been described. In the sequences according to the invention, there is a noticeable accumulation of lysines at the C-terminus.

| Moss elongase PSE1: | C-terminus | KQKGAKTE |
| SEQ ID NO 4: | C-terminus | KTKKA |
| SEQ ID NO 6 | C-terminus | KKSTPAAKKTN |
| SEQ ID NO 8: | C-terminus | KHLK |

These may be a possible gene variation.

There are Lys radicals which influence targeting, addressing and localization at or in the ER. A masking of this sequence, modification or spatial modification, in the vicinity of the end of the C-terminus, for example by fusion with GFP "green fluorescent protein" may be utilized to influence compartmentalization.

PSEs are preferably produced by recombinant DNA techniques. For example, a nucleic acid molecule encoding the protein is cloned into an expression vector (as described above), the expression vector is introduced into a host cell (as described above), and the PSE is expressed in the host cell. The PSE can then be isolated from the cells by a suitable purification scheme using standard techniques of protein purification. As an alternative for the recombinant expression, a PSE, a PSE polypeptide or a PSE peptide can be synthesized chemically by standard techniques of peptide synthesis. Moreover, native PSE can be isolated from cells (for example endothelial cells), for example using an anti-PSE antibody which can be raised by standard techniques, using a PSE according to the invention or a fragment thereof.

The invention also provides chimeric PSE proteins or PSE fusion proteins. As used in the present context, a "chimeric PSE protein" or "PSE fusion protein" encompasses a PSE polypeptide which is functionally bound to a non-PSE polypeptide. A "PSE polypeptide" refers to a polypeptide with an amino acid sequence which corresponds to a PSE, while a "non-PSE polypeptide" refers to a polypeptide with an amino acid sequence which corresponds to a protein which is essentially not homologous with PSE, for example a protein which differs from PSE and which originates from the same or another organism. Within the fusion protein, the term "functionally linked" is to be understood as meaning that the PSE polypeptide and the non-PSE polypeptide are fused to each other in such a way that both sequences fulfill the predicted function which has been ascribed to the sequence used. The non-PSE polypeptide can be fused to the N terminus or the C terminus of the PSE polypeptide. In one embodiment the fusion protein is, for example, a GST-PSE fusion protein in which the PSE sequences are fused to the C terminus of the GST sequences. These fusion proteins can facilitate the purification of the recombinant PSEs. In a further embodiment, the fusion protein is a PSE which has a heterologous signal sequence at its N terminus. In certain host cells (for example mammalian host cells), expression and/or secretion of a PSE can be increased by using a heterologous signal sequence.

A chimeric PSE protein or PSE fusion protein according to the invention is produced by standard recombinant DNA techniques. For example, DNA fragments which encode different polypeptide sequences are ligated to each other in correct reading frame using conventional techniques, for example by employing blunt ends or sticky ends for ligation, restriction enzyme cleavage for providing suitable ends, filling up cohesive ends, as required, treatment with alkaline phosphatase to avoid undesired linkages, and enzymatic ligation. In a further embodiment, the fusion gene can be synthesized by conventional techniques including DNA synthesizers. As an alternative, PCR amplification of gene fragments can be carried out using anchor primers which generate complementary overhangs between successive gene fragments which can subsequently be hybridized and reamplified to give rise to a chimeric gene sequence (see, for example, Current Protocols in Molecular Biology, Ed. Ausubel et al., John Wiley & Sons: 1992). Moreover, a large number of expression vectors which already encode a fusion unit (for example a GST polypeptide) are commercially available. PSE-encoding nucleic acid can be cloned into such an expression vector so that the fusion unit is linked in correct reading frame to the PSE protein.

PSE homologs can be generated by mutagenesis, for example by specific point mutation or truncating the PSE. The term "homologs" as used in the present context refers to a variant form of PSE which acts as agonist or antagonist of the PSE activity. A PSE agonist can essentially retain the same activity as PSE, or some of the biological activities. A PSE antagonist can inhibit one or more activities of the naturally occurring PSE form, for example by competitive binding to an upstream or downstream element of the metabolic cascade for cell membrane components which encompasses the PSE, or by binding to a PSE which mediates the transport of compounds via cell membranes, thus inhibiting translocation.

In an alternative embodiment, PSE homologs can be identified by screening combinatory libraries of mutants, for example truncated mutants, of PSE with regard to PSE agonist or PSE antagonist activity. In one embodiment, a variegated library of PSE variants is generated at the nucleic acid level by combinatory mutagenesis and encoded by a variegated genetic library. A variegated library of PSE variants can be generated for example by enzymatic ligation of a mixture of synthetic oligonucleotides into gene sequences so that a degenerate set of potential PSE sequences can be expressed as individual polypeptides or, alternatively, as a set of larger fusion proteins (for example for phage display) which comprise this set of PSE sequences. There is a multiplicity of methods which can be used for generating libraries of potential PSE homologs from a degenerate oligonucleotide sequence. The chemical synthesis of a degenerate gene sequence can be carried out in a DNA synthesizer, and the synthetic gene can then be ligated into a suitable expression vector. The use of a degenerate set of genes allows all sequences which encode the desired set of potential PSE sequences to be provided in a mixture. Methods for the synthesis of degenerate oligonucleotides are known in the art [see, for example, Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477].

In addition, libraries of PSE fragments can be used for generating a variegated population of PSE fragments for screening and for the subsequent selection of homologs of a PSE. In one embodiment, a library of fragments of the coding sequence can be generated by treating a double-stranded PCR fragment of a coding PSE sequence with a nuclease under conditions under which double-strand breaks only occur approximately once per molecule, denaturing the double-stranded DNA, renaturing the DNA with the formation of double-stranded DNA which can encompass sense/antisense pairs of various products with double-strand breaks, removal of single-stranded sections from newly formed duplices by treatment with S1 nuclease, and ligating the resulting fragment library into an expression vector. This method allows an expression library to be derived which encodes N-terminal, C-terminal and internal fragments of variously sized PSEs.

A number of techniques for screening gene products in combinatory libraries which have been generated by point mutations or truncation and for screening cDNA libraries for gene products with a selected property are known in the art.

These techniques can be adapted to rapid screening of the genetic libraries which have been generated by combinatory mutagenesis of PSE homologs. The most frequently used techniques for screening large genetic libraries which can be subjected to high-throughput analysis usually encompass cloning the genetic library into replicable expression vectors, transforming suitable cells with the resulting vector library, and expressing the combinatory genes under conditions under which detecting the desired activity facilitates the isolation of the vector encoding the gene whose product has been detected. Recursive ensemble mutagenese (REM), a novel technique which increases the frequency of functional mutants in the libraries, can be used in combination with the screening assays for identifying PSE homologs [Arkin and Yourvan (1992) Proc. Natl. Acad. Sci. USA 89:7811-7815; Delgrave et al. (1993) Protein Engineering 6(3):327-331]. Combinations of the abovementioned methods can also be used advantageously.

A further known technique for modifying catalytic properties of enzymes or the genes encoding them is gene shuffling (see, for example, WO 97/20078 or WO 98/13487), which is a combination of gene fragments where this new combination can additionally be varied by erroneous polymerase chain reactions thus creating a high sequence diversity to be assayed. However, the prerequisite for using such an approach is a suitable screening system to test the resulting gene diversity for functionality.

A screening method which identifies a PUFA-dependent enzyme activity, or activities, is a prerequisite in particular for screening elongase activities. As regards elongase activities with a specificity for PUFAs, the toxicity of arachidonic acid in the presence of a toxic metabolite (here: salicylic acid or salicylic acid derivatives), can be exploited in *Mucor* species which can be transformed with desired gene constructs by known transformation methods (Eroshin et al., Mikrobiologiya, Vol. 65, No. 1, 1996, pages 31-36) to carry out a growth based primary screening. Resulting clones can then be analyzed for their lipid constituents by means of gas chromatography and mass spectroscopy in order to identify the nature and quantity of starting materials and products.

In a further embodiment, cell-based assays can be made use of for analyzing a variegated PSE library using further processes known in the art.

In a further embodiment, the present invention relates to an antibody which binds specifically to the polypeptide of the present invention or to parts, for example epitopes, of such a protein. The antibody according to the invention can be used to identify and isolate other elongases, in particular PSEs. These antibodies can be monoclonal antibodies, polyclonal antibodies or synthetic antibodies, and also fragments of these antibodies, such as, for example, Fab, Fv or scFV fragments, etc. Monoclonal antibodies can be prepared, for example, by methods such as those described originally by Köhler and Milstein in Nature 256 (1975), 485, and Galfrö in Meth. Enzymol. 73 (1981). Antibodies and fragments thereof can also be prepared, for example, according to Harlow & Lane, "Antibodies, a Laboratory Manual", CSH Press, Cold Spring Harbor, 1988. These antibodies can be used to precipitate and localize, for example, the proteins according to the invention, or to monitor the synthesis of these proteins, for example in recombinant organisms, and to identify compounds which interact with the proteins according to the invention. In many cases, the binding of antibodies to antigens is equivalent to the binding of other ligands and antiligands.

The present invention furthermore relates to a process for identifying an agonist or antagonist of elongases, in particular PSEs, comprising
a) bringing the cells which express the polypeptide of the present invention into contact with a candidate substance;
b) testing the PSE activity;
c) comparing the PSE activity with a standard activity in the absence of the candidate substance, where a PSE activity that is higher than that of the standard indicates that the candidate substance is an agonist and where a PSE activity that is lower than that of the standard indicates that the candidate substance is an antagonist.

The candidate substance mentioned can be a substance that is synthesized chemically or produced microbiologically, being present, for example, in cell extracts of, for example, plants, animals or microorganisms. The substance mentioned may furthermore be known in the prior art but hitherto unknown as increasing or repressing the activity of the PSEs. The reaction mixture may be a cell free extract or comprise a cell or cell culture. Suitable methods are known to the person skilled in the art and described in a general manner, for example, in Alberts, Molecular Biology of the cell, $3^{rd}$ edition (1994), for example Chapter 17. The substances mentioned may be added, for example, to the reaction mixture or the culture medium or be injected into the cells or sprayed onto a plant.

If a sample which comprises a substance which is active according to the method according to the invention has been identified, it is then possible either to isolate the substance directly from the original sample or to divide the sample into various groups, for example when it consists of a large number of different components, to reduce the number of different substances per sample, and then to repeat the process according to the invention with such a "subsample" of the original sample. Depending on the complexity of the sample, the steps described above can be repeated a plurality of times, preferably until the sample identified by the method according to the invention comprises only a small number of substances or only one substance. The substance identified by the method according to the invention, or derivatives thereof, are preferably formulated further, such that they are suitable for use in plant breeding or plant cells or tissue culture.

Substances which can be identified and tested by the process according to the invention can be: expression libraries, for example cDNA expression libraries, peptides, proteins, nucleic acids, antibodies, small organic substances, hormones, PNAs or the like (Milner, Nature Medicin 1 (1995), 879-880; Hupp, Cell. 83 (1995), 237-245; Gibbs, Cell. 79 (1994), 193-198 and literature quoted therein). These substances can also be functional derivatives or analogs of known inhibitors or activators. Processes for preparing chemical derivatives or analogs are known to the person skilled in the art. The known derivatives and analogs can be tested using processes of the prior art. It is furthermore possible to use computer-aided design or peptidomimetics to prepare suitable derivatives and analogs. The cell or the tissue used for the process(es) according to the invention is preferably a host cell, plant cell or a plant tissue according to the invention, as described in the embodiments above.

Correspondingly, the present invention also relates to a substance which was identified by the process according to the invention mentioned above. The substance is, for example, a homolog of the PSE according to the invention. Homologs of the PSEs can be generated by mutagenesis, for example by point mutation or deletion of PSE. Here, the term "homolog" is used to mean a variant form of the PSEs which acts as agonist or antagonist for the PSE activity. An agonist may have substantially the same or part of the biological activity of the PSEs. An antagonist of the PSEs may inhibit one or more activities of the naturally occurring forms of the PSEs, for example bind competitively to a downstream or upstream member of the metabolic paths of fatty acid synthesis including the PSEs, or bind to PSEs and reducing or inhibiting the activity in the process.

Accordingly, the present invention also relates to an antibody or a fragment thereof as described herein which inhibits the activity of the PSEs according to the invention.

One aspect of the present invention relates to an antibody which specifically recognizes or binds to the above-described agonist or antagonist according to the invention.

A further aspect relates to a composition which comprises the anti body, the stop or the antisense molecule identified by the process according to the invention.

E. Uses and Processes/Methods According to the Invention

The nucleic acid molecules, proteins, protein homologs, fusion proteins, antibodies, primers, vectors and host cells described herein can be used in one or more of the methods which follow: identification of *Physcomitrella patens, Crypthecodinium, Phytophthora infestans* or *Thraustochytrium* and related organisms, genome mapping of organisms which are related with *Physcomitrella, Phytophthora, Crypthecodinium* or *Thraustochytrium*, identification and localization of *Physcomitrella, Phytophthora, Crypthecodinium* or *Thraustochytrium* sequences of interest, evolutionary studies, determination of PSE protein regions required for the function, modulation of a PSE activity; modulation of the metabolism of one or more cell membrane components; modulation of the transmembrane transport of one or more compounds, and modulation of the cellular production of a desired compound such as a fine chemical. The PSE nucleic acid molecules according to the invention have a multiplicity of uses. Firstly, they can be used for identifying an organism as *Physcomitrella, Phytophthora, Crypthecodinium* or *Thraustochytrium* or a close relative of these. They can also be used for identifying the presence of *Physcomitrella, Crypthecodinium, Phytophthora* or *Thraustochytrium* or a relative of these in a mixed population of microorganisms. The invention provides the nucleic acid sequences of a series of *Physcomitrella, Phytophthora, Crypthecodinium* or *Thraustochytrium* genes; the presence or absence of this organism can be determined by screening the extracted genomic DNA of a culture of a uniform or mixed population of microorganisms under stringent conditions with a probe covering a region of a *Physcomitrella, Crypthecodinium, Phytophthora* or *Thraustochytrium* gene which is unique for this organism, or of parts of this gene. *Physcomitrella, Crypthecodinium, Phytophthora* or *Thraustochytrium* themselves are used for the commercial production of polyunsaturated acids. Moreover, the nucleic acids according to the invention are suitable for the production of PUFAs, also in other organisms, in particular when it is intended for the resulting PUFAs to be incorporated into the triacylglycerol fraction.

Furthermore, the nucleic acid and protein molecules according to the invention can act as marker for specific regions of the genome. They are not only suitable for mapping the genome, but also for functional studies of *Physcomitrella, Phytophthora, Crypthecodinium* or *Thraustochytrium* proteins. To identify the genome region to which a certain DNA-binding protein of *Physcomitrella, Crypthecodinium, Phytophthora* or *Thraustochytrium* binds, the *Physcomitrella, Crypthecodinium, Phytophthora* or *Thraustochytrium* genome can be fragmented, for example, and the fragments incubated with the DNA-binding protein. Those which bind the protein can additionally be screened with the nucleic acid molecules according to the invention, preferably with readily detectable markers; the binding of such a nucleic acid molecule to the genome fragment makes possible the localization of the fragment on the genome map of *Physcomitrella, Phytophthora, Crypthecodinium* or *Thraustochytrium* and, if this is carried out repeatedly with different enzymes, facilitates a rapid determination of the nucleic acid sequence to which the protein binds. Moreover, the nucleic acid molecules according to the invention can have sufficient homology with the sequences of related species for these nucleic acid molecules to be able to act as markers for the construction of a genomic map in related fungi or algae.

The PSE nucleic acid molecules according to the invention are also suitable for evolutionary studies and studies of the protein structure. The metabolic and transport processes in which the molecules according to the invention are involved are utilized by a large number of prokaryotic and eukaryotic cells; the evolutionary degree of relatedness of the organisms can be determined by comparing the sequences of the nucleic acid molecules according to the invention which those which encode similar enzymes from other organisms. Accordingly, such a comparison allows the determination of which sequence regions are conserved and which are not conserved, which may be helpful when determining regions of the protein which are essential for enzyme function. This type of determination is valuable for protein engineering studies and may provide a clue of how much mutagenesis the protein can tolerate without losing its function.

Manipulation of the PSE nucleic acid molecules according to the invention can lead to the production of PSEs with functional differences to the wild-type PSEs. The efficacy or activity of these proteins can be improved; they may be present in the cell in larger numbers than usual; or their efficacy or activity can be reduced. An improved efficacy or activity means, for example, that the enzyme has a higher selectivity and/or activity, preferably an activity which is at least 10% higher, very especially an activity which is at least 20% higher, very especially preferably an activity which is at least 30% higher, than the original enzyme.

There exists a series of mechanisms by which modification of a PSE according to the invention can directly affect yield, production and/or production efficacy of a fine chemical comprising such a modified protein. Obtaining fine chemical compounds from cultures of ciliates, algae or fungi on a large scale is significantly improved when the cell secretes the desired compounds, since these compounds can readily be isolated from the culture medium (in contrast to extraction from the biomass of the cultured cells). Otherwise, purification can be improved when the cell stores compounds in vivo in a specialized compartment with a sort of concentration mechanism. In plants which express PSEs, an increased transport may lead to better distribution within the plant tissue and the plant organs. Increasing the number or the activity of the transporter molecules which export fine chemicals from the cell may allow the quantity of the fine chemical produced, which is present in the extracellular medium, to be increased, thus facilitating harvesting and purification or, in the case of plants, more efficient distribution. In contrast, increased amounts of cofactors, precursor molecules and intermediates for the suitable biosynthetic pathways are required for an efficient overproduction of one or more fine chemicals. Increasing the number and/or the activity of transporter proteins involved in the import of nutrients such as carbon sources (i.e. sugars), nitrogen sources (i.e. amino acids, ammonium salts), phosphate and sulfur can improve the production of a fine chemical owing to the elimination of all limitations of the nutrients available in the biosynthetic process. Fatty acids such as PUFAs and lipids comprising PUFAs are desirable fine chemicals themselves. Optimizing the activity or increasing the number of one or more PSEs according to the invention involved in the biosynthesis of these compounds, or disrupting the activity of one or more PSEs involved in the breakdown of these compounds, can thus increase the yield, production and/or production efficacy of fatty acid and lipid molecules in ciliates, algae, plants, fungi, yeasts or other microorganisms.

The manipulation of one or more PSE genes according to the invention can likewise lead to PSEs with modified activities which indirectly affect the production of one or more desired fine chemicals from algae, plants, ciliates or fungi. The normal biochemical metabolic processes lead, for example, to the production of a multiplicity of waste products (for example hydrogen peroxide and other reactive oxygen species) which can actively disrupt these metabolic processes [for example, peroxynitrite is known to nitrate tyrosin side chains, thus inactivating some enzymes with tyrosin in the active center; Groves, J. T. (1999) Curr. Opin. Chem. Biol. 3(2); 226-235]. While these waste products are normally excreted, the cells used for fermentative production on a large scale are optimized for the overproduction of one or more fine chemicals and can therefore produce more waste products than is customary for a wild-type cell. Optimizing the activity of one or more PSEs according to the invention which are involved in the export of waste molecules allows the improvement of the viability of the cell and the maintenance of an efficient metabolic activity. Also, the presence of high intracellular amounts of the desired fine chemical can in fact be toxic to the cell, so that the viability of the cell can be improved by increasing the ability of the cell to secrete these compounds.

Furthermore, the PSEs according to the invention can be manipulated in such a way that the relative amounts of various lipid and fatty acid molecules are modified. This can have a decisive effect on the lipid composition of the cell membrane. Since each lipid type has different physical properties, the modification of the lipid composition of a membrane can significantly modify membrane fluidity. Changes in membrane fluidity can affect the transport of molecules via the membrane which, as explained above, can modify the export of waste products or of the fine chemical produced or the import of nutrients which are required. These changes in membrane fluidity can also have a decisive effect on cell integrity; cells with comparatively weaker membranes are more susceptible to abiotic and biotic stress conditions which can damage or kill the cell. Manipulation of PSEs which are involved in the production of fatty acids and lipids for membrane synthesis so that the resulting membrane has a membrane composition which is more susceptible to the environmental conditions prevailing in the cultures used for the production of fine chemicals should allow more cells to survive and multiply. Larger numbers of producing cells should manifest themselves in greater yields, higher production or higher production efficacy of the fine chemical from the culture.

The abovementioned mutagenesis strategies for PSEs intended to lead to elevated yields of a fine chemical are not to be construed as limiting; variations of these strategies are readily obvious to the skilled worker. Using these mechanisms, and with the aid of the mechanisms disclosed herein, the nucleic acid and protein molecules according to the invention can be used for generating algae, ciliates, plants, animals, fungi or other microorganisms such as *C. glutamicum* which express mutated PSE nucleic acid and protein molecules so that the yield, production and/or production efficacy of a desired compound is improved. This desired compound can be any natural product of algae, ciliates, plants, animals, fungi or bacteria which encompasses the end products of biosynthetic pathways and intermediates of naturally occurring metabolic pathways, and also molecules which do not naturally occur in the metabolism of these cells, but which are produced by the cells according to the invention.

A further embodiment according to the invention is a process for the production of PUFAs, which comprises culturing an organism which contains a nucleic acid according to the invention, a gene construct according to the invention or a vector according to the invention which encode a polypeptide which elongates $C_{16}$-, $C_{18}$- or $C_{20}$-fatty acids with at least two double bonds in the fatty acid molecule by at least two carbon atoms under conditions under which PUFAs are produced in the organism. PUFAs prepared by this process can be isolated by harvesting the organisms either from the culture in which they grow or from the field, and disrupting and/or extracting the harvested material with an organic solvent. The oil, which contains lipids, phospholipids, sphingolipids, glycolipids, triacylglycerols and/or free fatty acids with a higher PUFA content, can be isolated from this solvent. The free fatty acids with a higher content of PUFAs can be isolated by basic or acid hydrolysis of the lipids, phospholipids, sphingolipids, glycolipids and triacylglycerols. A higher content of PUFAS means at least 5%, preferably 10%, especially preferably 20%, very especially preferably 40% more PUFAs than the original organism which does not have additional nucleic acid encoding the elongase according to the invention.

The PUFAs produced by this process are preferably $C_{18}$-, $C_{20}$- or $C_{22}$-fatty acid molecules with at least two double bonds in the fatty acid molecule, preferably three, four, five or six double bonds, especially preferably three or five double bonds. These $C_{18}$-, $C_{20}$- or $C_{22}$-fatty acid molecules can be isolated from the organism in the form of an oil, lipid or a free fatty acid. Examples of suitable organisms are those mentioned above. Preferred organisms are microorganisms, animals or plants, especially preferably plants or algae, very especially preferably transgenic plants.

An embodiment according to the invention are oils, lipids or fatty acids or fractions thereof which have been prepared by the above-described process, especially preferably oil, lipid or a fatty acid composition encompassing PUFAs and originating from transgenic plants.

One embodiment of the invention are oils, lipids or fatty acids which have been prepared by the process according to the invention. Other embodiments of the invention are oil, lipid or fatty acid compositions which comprise PUFAs produced by the process according to the invention and which are derived from transgenic plants which comprise a nucleic acid, a gene construct or vector according to the invention.

A further embodiment according to the invention is the use of the oil, lipid or the fatty acid composition in feeding stuffs, foodstuffs, cosmetics or pharmaceuticals.

A further embodiment of the invention relates to a kit, comprising the nucleic acid according to the invention, the gene construct according to the invention, the amino acid sequence according to the invention, the antisense nucleic acid molecule according to the invention, the antibody and/or composition according to the invention, an antagonist or agonist prepared by the process according to the invention and/or oils, lipids and/or fatty acids according to the invention, or a fraction thereof. The kit may also comprise the host cells, organisms or plants according to the invention, or parts thereof, parts of the plants according to the invention which can be harvested, or propagation material, or else the antagonist or agonist according to the invention. The components of the kit of the present invention can be packed in suitable containers, for example together with or in buffers or other solutions. One or more of the components mentioned may be packed into one and the same container. Additionally or alternatively, one or more of the components mentioned can, for example, be absorbed on a solid surface, for example a nitrocellulose filter, glass plates, chips, nylon membranes or microtiter plates. The kit can be used for any of the methods and embodiments described herein, for example for producing host cells, transgenic plants, for detecting homologous sequences, for identifying antagonists or agonists, and the like. Furthermore, the kit may contain instructions on how to use the kit for one of the applications mentioned.

This invention is illustrated in greater detail by the examples which follow, which are not to be construed as limiting. The content of all references, patent applications, patents and published patent applications cited in this patent application is incorporated herein by reference.

EXAMPLES

Example 1

General Methods a) General Cloning Methods:

Cloning methods, such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, the culture of bacteria and the sequence analysis of recombinant DNA were carried out as described in Sambrook et al. [(1989), Cold Spring Harbor Laboratory Press: ISBN 0-87969-309-6] or Kaiser, Michaelis and Mitchell [(1994), "Methods in Yeast Genetics", Cold Spring Harbor Laboratory Press: ISBN 0-87969-451-3]. The transformation and culture of algae such as *Chlorella* or *Phaeodactylum* are carried out as described by El-Sheekh [(1999), Biologia Plantarum 42:209-216] or Apt et al. [(1996) Molecular and General Genetics 252 (5):872-9].

b) Chemicals

Unless otherwise specified in the text, the chemicals used were obtained in analytical grade quality from Fluka (Neu-Ulm), Merck (Darmstadt), Roth (Karlsruhe), Serva (Heidelberg) and Sigma (Deisenhofen). Solutions were prepared using pure pyrogen free water, referred to in the following text as $H_2O$, from a Milli-Q water system water purification unit (Millipore, Eschborn). Restriction endonucleases, DNA-modifying enzymes and molecular biology kits were obtained from AGS (Heidelberg), Amersham (Brunswick), Biometra (Gottingen), Boehringer (Mannheim), Genomed (Bad Oeynhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). Unless otherwise specified, they were used following the manufacturer's instructions.

c) Cell Material

The present studies were carried out using a *Thraustochytrium* strain which is available via the American Type Culture Collection (ATCC) with the strain number ATCC26185 (Thraustochytrium) or, in the case of *Crypthecodinium*, from the Provasoli-Guillard National Center for Culture of Marine Phytoplankton ((CCMP) West Boothbay Harbour, Me., USA), with the strain culture No. CCMP316. The algae were cultured in the dark at 25 degrees Celsius in glass tubes into which air was passed in from the bottom. As an alternative, *Thraustochytrium* was grown as described in detail by Singh & Ward (1997, Advances in Microbiology, 45, 271-311).

The culture medium used for *Crypthecodinium* was the f/2 culture medium supplemented with 10% organic medium of Guillard, R. R. L. [1975; Culture of phytoplankton for feeding marine invertebrates. In: Smith, W. L. and Chanley, M. H. (Eds.) Culture of marine Invertebrate animals, NY Plenum Press, pp. 29-60.]. It comprises 995.5 ml of (artificial) salt water 1 ml $NaNO_3$ (75 g/l), 1 ml $NaH_2PO_4$ (5 g/l), 1 ml trace metal solution, 1 ml Tris/Cl pH 8.0, 0.5 ml f/2 vitamin solution Trace metal solution: $Na_2EDTA$ (4.36 g/l), $FeCl_3$ (3.15 g/l), Primary Trace metals: $CuSO_4$ (10 g/l), $ZnSO_4$ (22 g/l), $CoCl_2$ (10 g/l), $MnCl_2$ (18 g/l), $NaMoO_4$ (6.3 g/l)

f/2 vitamin solution: biotin: 10 mg/l, thiamin 200 mg/l, vitamin B12 0.1 mg/l org medium: sodium acetate (1 g/l), glucose (6 g/l), sodium succinate (3 g/l), Bacto tryptone (4 g/l), yeast extract (2 g/l)

d) Moss Material (=Plant Material)

For this study, plants of the species *Physcomitrella patens* (Hedw.) B.S.G. from the collection of the department for genetic studies, University of Hamburg, were used. They are derived from strain 16/14, which had been collected by H.L.K. Whitehouse in Gransden Wood, Huntingdonshire (England) and subcultured by Engel (1968, Am J Bot 55, 438-446) from a spore. Proliferation of the plants was done by means of spores and by regenerating the gametophytes. The protonema developed from the haploid spore into chloroplast-rich chloronema and chloroplast-depleted caulonema, which budded after approximately 12 days. These buds grew into gametophores with antheridia and archegonia. Fertilization gave rise to diploid sporophyte with short seta and spore capsule in which the meiospores mature.

e) Plant Culture

Plants were grown in a controlled environment cabinet at an air temperature of 25° C. and a light intensity of 55 $\mu mol^{-1}$ $m^{-2}$ (white light; Philips TL 65W/25 fluorescent tube) and a light/dark region of 16/8 hours. The moss was grown either in liquid culture using Reski and Abel's modified knop medium (1985, Planta 165, 354-358) or on solid knop medium using 1% Oxoid agar (Unipath, Basingstoke, England).

The protonemata used for RNA and DNA isolation were grown in aerated liquid cultures. The protonemata were comminuted every 9 days and transferred into fresh culture medium.

f) Cultivation of *Phytophthora infestans*

Initially, a cDNA library of *Phytophthora infestans* was prepared. To this end, it is possible to obtain strain ATCC 48886 from the American Type Culture Collection Rockville, USA. As a variation of the culture protocol described for the strain ATCC 48886, *Phytophthora* spores were washed with cold, doubly distilled water and kept in a fridge for 6 hours to induce sporulation. The material was then transferred into pea medium. To this end, 150 g of deep-frozen peas (Iglu, obtainable from local supermarkets) were autoclaved under sterile conditions and 1 liter of water for 20 minutes. The material was grown in 100-ml-flasks at room temperature, on an orbitalshaker (200 rpm). After two days, 2 flasks were filtered off and the filter residue was comminuted in liquid nitrogen, using mortar and pestle, and for the following 4 days, this procedure was repeated for in each case 2 flasks.

Example 2

Isolation of Total DNA from Plants and Microorganisms Such as *Thraustochytrium* and *Crypthecodinium* for Hybridization Experiments The details on the isolation of total DNA refer to the work-up of plant material with a fresh weight of one gram.

CTAB buffer: 2% (w/v) N-acetyl-N,N,N-trimethylammonium bromide (CTAB); 100 mM Tris-HCl, pH 8.0; 1.4 M NaCl; 20 mM EDTA.

N-Laurylsarcosine buffer: 10% (w/v) N-laurylsarcosine; 100 mM Tris-HCl, pH 8.0; 20 mM EDTA.

The plant material or *Crypthecodinium* or *Thraustochytrium* cell material was triturated under liquid nitrogen in a mortar to give a fine powder and transferred into 2 ml Eppendorf vessels. The frozen plant material was then covered with a layer of 1 ml of decomposition buffer (1 ml CTAB buffer, 100 ml N-laurylsarcosine buffer, 20 ml β-mercaptoethanol and 10 ml proteinase K solution, 10 mg/ml) and incubated at 60° C. for one hour with continuous shaking. The homogenate obtained was distributed into two Eppendorf vessels (2 ml) and extracted twice by shaking with an equal volume of chloroform/isoamyl alcohol (24:1). For phase separation, centrifugation was carried out at 8000×g and RT (=room temperature=-23° C.) for 15 minutes in each case. The DNA was then precipitated at -70° C. for 30 minutes using ice-cold isopropanol. The precipitated DNA was sedimented at 4° C. and 10,000 g for 30 minutes and resuspended in 180 ml of TE buffer (Sambrook et al., 1989, Cold Spring Harbor Laboratory Press: ISBN 0-87969-309-6). For further purification, the DNA was treated with NaCl (1.2 M final concentration) and precipitated again at -70° C. for 30 minutes using twice the volume of absolute ethanol. After a wash step with 70% ethanol, the DNA was dried and subsequently taken up in 50 ml of $H_2O$+RNase (50 mg/ml final concentration). The DNA was dissolved overnight at 4° C. and the RNase cleavage was subsequently carried out for 1 hour at 37° C. The DNA was stored at 4° C.

Example 3

Isolation of Total RNA and Poly(A)+ RNA from Plants and Microorganisms (*Crypthecodinium* and *Thraustochytrium*)

Total RNA was isolated from plants such as linseed and oilseed rape by a method described by Logemann et al (1987, Anal. Biochem. 163, 21). The total RNA from moss can be obtained from protonema tissue using the GTC method (Reski et al., 1994, Mol. Gen. Genet., 244:352-359).

RNA Isolation from *Crypthecodinium* and *Thraustochytrium*:

Frozen samples of algae (-70° C.) are triturated in an ice-cold mortar under liquid nitrogen to give a fine powder. 2 volumes of homogenization medium (12.024 g sorbitol, 40.0 ml 1M Tris-HCl, pH 9 (0.2 M); 12.0 ml 5 M NaCl (0.3 M), 8.0 ml 250 mM EDTA, 761.0 mg EGTA, 40.0 ml 10% SDS are made up to 200 ml with $H_2O$ and the pH is brought to 8.5) and 4 volumes of phenol with 0.2% mercaptoethanol are added to the frozen cell powder at 40-50° C. while mixing thoroughly. Then, 2 volumes of chloroform are added and the mixture is stirred vigorously for 15 minutes. The mixture is centrifuged for 10 minutes at 10,000 g and the aqueous phase is extracted with phenol/chloroform (2 vol/2 vol) and then with chloroform.

The resulting volume of the aqueous phase is treated with 1/20 volume of 4 M sodium acetate (pH 6) and 1 volume of (ice-cold) isopropanol, and the nucleic acids are precipitated at -20° C. The mixture is centrifuged for 30 minutes at 10,000 g and the supernatant is removed by suction. This is followed by a wash step with 70% EtOH and another centrifugation step. The sediment is taken up in Tris borate buffer (80 mM Tris borate buffer, 10 mM EDTA, pH 7.0). The supernatant is then treated with 1/3 vol of 8 M LiCl, mixed are incubated for 30 minutes at 4° C. After recentrifugation, the sediment is washed with 70% ethanol, centrifuged, and the sediment is dissolved in RNase free water.

Poly(A)+-RNA is isolated using Dyna Beads® (Dynal, Oslo, Finland) following the instructions in the manufacturer's protocol.

After the RNA or poly(A)+-RNA concentration has been determined, the RNA is precipitated by adding 1/10 volume 3 M sodium acetate, pH 4.6 and 2 volumes of ethanol and stored at -70° C.

For the analysis, 20 μg portions of RNA are separated in a formaldehyde-containing 1.5% strength agarose gel and transferred to nylon membranes (Hybond, Amersham). Specific transcripts are detected as described by Amasino ((1986) Anal. Biochem. 152, 304)).

Isolation of Total RNA and Poly (A)+ RNA from *Phytophthora infestans*:

Total RNA was obtained using the RNeasy Plant Total RNA kit (Quiagen, Milden) and the buffer contained therein, following the instructions of the manufacturer. From the total RNA thus obtained, the poly-(A)+ RNA was isolated using the Poly Attract in RNA Isolation System III from Promega (Heidelberg), following the instructions of the manufacturer.

Example 4

Construction of the cDNA Library

To construct the cDNA library from *Physcomitrella*, *Crypthecodinium* and *Thraustochytrium*, respectively, the first-strand synthesis was carried out using murine leukemia virus reverse transcriptase (Roche, Mannheim, Germany) and oligo-d(T) primers, while the second-strand synthesis was carried out by incubation with DNA polymerase I, Klenow enzyme and cleavage with RNase H at 12° C. (2 hours), 16° C. (1 hour) and 22° C. (1 hour). The reaction was quenched by incubation at 65° C. (10 minutes) and subsequently transferred to ice. Double-stranded DNA molecules were made blunt-ended with T4 DNA polymerase (Roche, Mannheim) at 37° C. (30 minutes). The nucleotides were removed by extraction with phenol/chloroform and Sephadex G50 spin columns. EcoRI/XhoI adapters (Pharmacia, Freiburg, Germany) were ligated to the cDNA ends by means of T4 DNA ligase (Roche, 12° C., overnight), recut with XhoI and phosphorylated by incubation with polynucleotide kinase (Roche, 37° C., 30 minutes). This mixture was subjected to separation on a low-melting agarose gel. DNA molecules of over 300 base pairs were eluted from the gel, extracted with phenol, concentrated on Elutip D columns (Schleicher and Schüll, Dassel, Germany), ligated to vector arms and packaged into lambda-ZAPII phages or lambda-ZAP-express phages using the Gigapack Gold kit (Stratagene, Amsterdam, the Netherlands), using the manufacturer's material and following their instructions.

The construction of a cDNA library for *Phytophthora infestans* was carried out as described above.

Example 5

DNA Sequencing and Computer Analysis cDNA libraries as described in Example 4 were used for DNA sequencing by standard methods, in particular the chain termination method using the ABI PRISM Big Dye Terminator Cycle Sequencing Ready Reaction Kit (Perkin Elmer, Weiterstadt, Germany). Following the plasmid preparation from cDNA libraries, individual random clones were sequenced via in-vivo mass excision and retransformation of DH10B on agar plates (details on materials and protocol: Stratagene, Amsterdam, the Netherlands). Plasmid DNA was prepared from E. coli cultures grown overnight in Luria broth supplemented with ampicillin (see Sambrook et al. (1989) (Cold Spring Harbor Laboratory Press: ISBN 0-87969-309-6)) using a Qiagen DNA preparation robot (Qiagen, Hilden) following the manufacturer's protocols. Sequencing primers with the following nucleotide sequences were used:

```
5'-CAGGAAACAGCTATGACC-3'    (SEQ ID NO: 13)
5'-CTAAAGGGAACAAAAGCTG-3'   (SEQ ID NO: 14)
5'-TGTAAAACGACGGCCAGT-3'    (SEQ ID NI: 15)
```

The sequences were processed and recorded using the EST-MAX standard software package which is commercially available from Bio Max (Munich, Germany). Exploiting comparative algorithms and using a searching sequence, homologous genes were searched for using the BLAST program (Altschul et al. (1997) "Gapped BLAST and PSI BLAST: a new generation of protein database search programs", Nucleic Acids Res. 25:3389-3402). One sequence from *Crypthecodinium* and *Thraustochytrium* with homologies with the search sequence of the *Physcomitrella patens* moss elongase were characterized in greater detail.

Example 6a

Identification of the Tc_PSE1 (SEQ ID NO: 3) and Tc_PSE2 (SEQ ID NO: 5) Gene (Tc=*Thraustochytrium*) and of the Cc_PSE1 (SEQ ID NO: 7) and Cc_PSE2 Gene (Cc=*Crypthecodinium cohnii*) by comparison with the *Physcomitrella patens* Pp_PSE1 (SEQ ID NO: 1) Gene The full length sequence of the Pp_PSE1 moss elongase (SEQ ID NO: 2) according to the invention (name: see also Table 2) was employed for the sequence comparisons in the TBLASTN search algorithm:

```
                                        (SEQ ID NO: 2)
MEVVERFYGE  LDGKVSQGVN  ALLGSFGVEL  TDTPTTKGLP

LVDSPTPIVL  GVSVYLTIVI  GGLLWIKARD  LKPRASEPFL

LQALVLVHNL  FCFALSLYMC  VGIAYQAITW  RYSLWGNAYN

PKHKEMAILV  YLFYMSKYVE  FMDTVIMILK  RSTRQISFLH

VYHHSSISLI  WWAIAHHAPG  GEAYWSAALN  SGVHVLMYAY

YFLAACLRSS  PKLKNKYLFW  GRYLTQFQMF  QFMLNLVQAY

YDMKTNAPYP  QWLIKILFYY  MISLLFLFGN  FYVQKYIKPS

DGKQKGAKTE.
```

The complete nucleotide sequence of the moss elongase Pp_PSE1 cDNA is composed of approximately 1200 bp. It contains an open reading frame of 873 bp which encodes 290 amino acids with a calculated molecular mass of 33.4 Da. The protein sequence only has 38.5% identity and 48.3% similarity with a *Saccharomyces cerevisiae* gene product, for example the *Saccharomyces cerevisiae* PSE1 gene product, which is required in yeast for the elongation of fatty acids with medium chain length (Toke & Martin, 1996, Isolation and characterization of a gene affecting fatty acid elongation in *Saccharomyces cerevisiae*. Journal of Biological Chemistry 271, 18413-18422).

The EST sequences CC001042041R, TC002034029R and TC002014093R were first considered as target gene amongst other candidate genes owing to initially weak homologies with the *Physcomitrella patens* elongase (see Table 2), the PSE1 gene. FIG. 5 shows the result of the comparison of the Pp_PSE1 peptide sequence with the found sequence. It is part of the nucleic acid of Seq ID NO:3 according to the invention (gene name: TcPSE1, inventors' database No. TC002034029R). Letters indicate identical amino acids, while the plus symbol denotes a chemically similar amino acid. The identities and homologies of all sequences found in accordance with the invention can be seen from the summary in Table 3.

Sequencing of the complete cDNA fragment from clone TC002034029R resulted in a sequence of 693 base pairs starting with the first base in the open reading frame. The sequence encodes a polypeptide of 195 amino acids shown in Seq ID NO:4 with a stop codon in base pair position translated from Seq ID NO:3 in base pair position 586-588. Clone TC002014093R comprises a virtually complete elongase polypeptide as can be seen from the sequence alignment in FIG. 7. Lines denote identical amino acids, while colons and dots represent chemically exchangeable, i.e. chemically equivalent, amino acids. The alignment was carried out using Henikoff & Henikoff's BLOSUM62 amino acid substitution matrix ((1992) Amino acid substitution matrices from protein blocks. Proc. Natl. Acad. Sci. USA 89: 10915-10919). Parameters used: Gap Weight: 8; Average Match: 2.912, Length Weight: 2, Average Mismatch: −2.003.

Furthermore, a second EST was identified by the sequence alignment. The alignment of the Pp_PSE1 peptide sequence with the found sequence is shown in FIG. 6. Even though the homology amongst the parameters chosen is restricted to a few amino acids, this refers to a highly conserved region of the PUFA specific elongases. The sequence of the complete cloned fragment was therefore determined.

Sequencing of the complete cDNA fragment of clone TC002014093R resulted in a sequence of 955 base pairs starting with the first base in the open reading frame. This is referred to by SEQ ID NO:5 according to the invention. The sequence encodes a polypeptide of 297 amino acids with a stop codon in base pair position 892-894 shown in accordance with the invention in SEQ ID NO: 6.

The *Crypthecodinium cohnii* EST CC001042041R which encodes the Cc_PSE1 gene was identified with the aid of the sequence PpPSE1. The isolated EST CC001042041R, shown in accordance with the invention as SEQ ID NO:7, is 708 base pairs long and has an open reading frame of 642 base pairs from the first base which encodes 214 amino acids and has a stop codon in position 643-645. The amino acid sequence up to the stop codon is shown in accordance with the invention in SEQ ID NO:8.

Besides the similarity with the PSE1 gene product, the similarity with the *Saccharomyces cerevisiae* elongase (see elo 1P), which is required in yeast for the elongation of fatty acids with medium chain length, may also be resorted to (Toke & Martin, 1996, Isolation and characterization of a gene affecting fatty acid elongation in *Saccharomyces cerevisiae*. Journal of Biological Chemistry 271, 18413-18422). Table 3 shows the identities and homologies of elongases according to the invention with each other and with the *Physcomitrella patens* and yeast elongases. The data were obtained with the aid of the GAP program as subprogram of the following software: Wisconsin Package Version 10.0 (Genetics Computer Group (GCG), Madison, Wis., USA).

TABLE 3

| Identity/ homology | Tc_PSE1 (SEQ ID NO: 4) | TC_PSE2 (SEQ ID NO: 6) | Pp_PSE1 (SEQ ID NO: 2) | Sce elo 1P |
|---|---|---|---|---|
| Cc_PSE1 | 47.1%/ 40.2% | 50.6%/ 43.5% | 38.5%/ 29.4% | 45.1%/ 33.5% |
| Tc_PSE1 | 100/100 | n.d. | 43.2%/ 32.7% | 41.9%/ 29.9% |
| Tc_PSE2 | 41.7%/ 29.5% | 100/100 | 39.2%/30.0 | 35.4%/ 27.8% |

In particular, FIGS. 5 to 10 can be used to derive the following sequence motifs as regions of high homology and corresponding consensus sequences derived therefrom which, by back translating the amino acids into three-base-pair codons, lead to oligonucleotides which can be exploited for isolating novel elongases by means of polymerase chain reaction. They are, in particular, the sequence motifs shown in FIG. 10. These motifs can be used for deriving oligonucleotides which, in combination with two oligonucleotides, can be employed in PCR experiments for isolating further elongase fragments. To do this, it is expedient to construct and synthesize one oligonucleotide matching the conventionally defined 5'-3' strand and a second one with an oligonucleotide matching the 3'-5' strand downstream. This results in a definable number of primer combinations, which is limited by permutation of the variants which are possible.

In this context, use may also be made of oligo-dT-primers and variants thereof, for example by the last base allowing specificity for a transcript pool, such as, for example, oligo dT (12-20) X, where X can be a G, C or T. Also, a second base oligo dT (12-20) XY can be made use of, where X can be a G, C or A, while the Y can be an A, G, C or T.

The above-defined sequences allow 17- to 20mer oligonucleotides to be derived which can be exploited for isolating gene fragments by varying the primer combinations and experimental parameters such as the temperature program, Mg ion concentration and the like. The resulting fragments can be cloned into suitable vectors and the sequence of resulting clones can be determined by current methods for identifying novel elongases.

Example 6b

Isolation of the cDNA Clone from *Phytophthora infestans*

The cDNA clone designated PI001002014R (SEQ ID NO:11) from *Phytophthora infestans* was identified from cDNAs sequenced at random, using homologies to PUFA elongase from the moss *Physcomitrella patens* (ATCCC 48886). The clone contains the consensus motif MyxYYF shown in FIG. 8, where, different from PUFA elongases which have hitherto been identified, a threonine radical was found as variable amino acid x. This further variation can be used for deriving PCR primers.

Example 7

Identification of Genes by Means of Hybridization (TC002034029R-11 iGenTc-PCE1)

Gene sequences can be used for identifying homologous or heterologous genes from cDNA libraries or genomic libraries.

Homologous genes (i.e. full length cDNA clones which are homologous, or homologs) can be isolated via nucleic acid hybridization using, for example, cDNA libraries: the method can be made use of in particular for isolating functionally active full length genes of SEQ ID NO:1, SEQ ID NO:3, SEQ ID NO:5, SEQ ID NO:7, SEQ ID NO:9 and SEQ ID NO:11. Depending on the frequency of the gene of interest, 100,000 up to 1,000,000 recombinant bacteriophages are plated and transferred to a nylon membrane. After denaturation with alkali, the DNA is immobilized on the membrane, for example by UV crosslinking. Hybridization is performed under highly stringent conditions. The hybridization and the wash steps are carried out in aqueous solution at an ionic strength of 1 M NaCl and a temperature of 68° C. Hybridization probes were generated for example by labeling with radioactive ($^{32}$P—) nick transcription (High Prime, Roche, Mannheim, Germany). The signals are detected by autoradiography.

Partially homologous or heterologous genes which are related but not identical can be identified analogously to the process described above using low-stringency hybridization and wash conditions. For the aqueous hybridization, the ionic strength was usually kept at 1 M NaCl, and the temperature was lowered gradually from 68 to 42° C.

The isolation of gene sequences which only exhibit homologies with an individual domain of, for example, 10 to 20 amino acids can be carried out using synthetic, radiolabeled oligonucleotide probes. Radiolabeled oligonucleotides are generated by phosphorylating the 5' end of two complementary oligonucleotides with T4 polynucleotide kinase. The complementary oligonucleotides are hybridized and ligated with each other to give rise to concatemers. The double stranded concatemers are radiolabeled for example by nick transcription. Hybridization is usually carried out under low stringency conditions using high oligonucleotide concentrations.

Oligonucleotide Hybridization Solution:
6×SSC
0.01 M sodium phosphate
1 mM EDTA (pH 8)
0.5% SDS
100 µg/ml denaturated salmon sperm DNA
0.1% dry low-fat milk During the hybridization, the temperature is lowered stepwise to 5 to 10° C. below the calculated oligonucleotide temperature or to room temperature (unless otherwise specified, RT=−23° C. in all experiments), followed by wash steps and autoradiography. Washing is carried out at extremely low stringency, for example 3 wash steps using 4×SSC. Further details are as described by Sambrook, J., et al. (1989), "Molecular Cloning: A Laboratory Manual", Cold Spring Harbor Laboratory Press, or Ausubel, F. M., et al. (1994) "Current Protocols in Molecular Biology", John Wiley & Sons.

The clone TC002034029R-11 with the gene name Tc_PCE1_1 is a full-length sequence of an elongase from *Thraustochytrium* and thus longer than the clone TC002034029R from Seq. ID No. 3 and Seq. ID No. 4. The clone was isolated using a hybridization method, as described above (Example 7). It is a DNA sequence of a length of 1 050 base pairs encoding for 271 amino acids having a start codon in base pair position 43-45 and a stop codon in base pair position 856-858.

Example 8

Identification of Target Genes by Screening Expression Libraries with Antibodies To generate recombinant protein, for example in *E. coli*, cDNA sequences are used (for example Qiagen QIAexpress pQE system). The recombinant proteins are then affinity-purified, usually via Ni-NTA affinity chromatography (Qiagen). The recombinant proteins are then used for raising specific antibodies, for example using standard techniques for immunizing rabbits. The antibodies are then affinity purified using an Ni NTA column which is presaturated with recombinant antigen, as described by Gu et al., (1994) BioTechniques 17:257 262. The antibody can then be used for screening expression cDNA libraries by immunological screening (Sambrook, J., et al. (1989), "Molecular Cloning: A Laboratory Manual", Cold Spring Harbor Laboratory Press, or Ausubel, F. M., et al. (1994) "Current Protocols in Molecular Biology", John Wiley & Sons).

Example 9

Plasmids for Plant Transformation

Binary vectors such as pBinAR can be used for plant transformation (Höfgen and Willmitzer, Plant Science 66 (1990) 221-230). The binary vectors can be constructed by ligating the cDNA in sense or antisense orientation into T DNA. 5' of the cDNA, a plant promoter activates cDNA transcription. A polyadenylation sequence is located 3' of the cDNA.

Tissue specific expression can be achieved using a tissue specific promoter. For example, seed-specific expression can be achieved by cloning in the napin or the LeB4 or the USP promoter 5' of the cDNA.

Any other seed specific promoter element can also be used. The CaMV-35S promoter may be used for constitutive expression in all of the plant.

The protein expressed can be targeted into a cellular compartment using a signal peptide, for example for plastids, mitochondria or the endoplasmatic reticulum (Kermode, Crit. Rev. Plant Sci. 15, 4 (1996) 285-423). The signal peptide is cloned 5' in correct reading frame with the cDNA in order to achieve subcellular localization of the fusion protein.

Example 10

Transformation of *Agrobacterium*

*Agrobacterium* mediated plant transformation can be carried out for example using the *Agrobacterium tumefaciens* strain GV3101 (pMP90) (Koncz and Schell, Mol. Gen. Genet. 204 (1986) 383-396) or LBA4404 (Clontech). The transformation can be carried out by standard transformation techniques (Deblaere et al., Nucl. Acids. Tes. 13 (1984), 4777-4788).

Example 11

Plant Transformation

*Agrobacterium* mediated plant transformation can be carried out using standard transformation and regeneration techniques (Gelvin, Stilton B., Schilperoort, Robert A., Plant Molecular Biology Manual, 2nd Ed., Dordrecht: Kluwer Academic Publ., 1995, in Sect., Ringbuc Zentrale Signatur: BT11 P ISBN 0-7923-2731-4; Glick, Bernard R., Thompson, John E., Methods in Plant Molecular Biology and Biotechnology, Boca Raton: CRC Press, 1993, 360 pp. ISBN 0-8493-5164-2).

For example, oilseed rape can be transformed by means of cotyledon or hypocotyledon transformation (Moloney et al., Plant Cell Report 8 (1989) 238 242; De Block et al., Plant Physiol. 91 (1989) 694-701). The use of antibiotics for the selection of *agrobacteria* and plants depends on the binary vector and the agrobacterial strain used for the transformation. The selection of oilseed rape is normally carried out using kanamycin as selectable plant marker.

*Agrobacterium* mediated gene transfer in linseed (*Linum usitatissimum*) can be carried out for example using a technique described by Mlynarova et al. (1994) Plant Cell Report 13:282-285.

The transformation of soya can be carried out for example using a technique described in EP-A-0 424 047 (Pioneer Hi-Bred International) or in EP-A-0 397 687, U.S. Pat. No. 5,376,543, U.S. Pat. No. 5,169,770 (University of Toledo).

Plant transformation using particle bombardment, polyethylene-glycol-mediated DNA uptake or via the silicon carbonate fiber technique is described, for example, by Freeling and Walbot "The maize handbook" (1993) ISBN 3-540-97826-7, Springer Verlag New York).

Example 12

Plasmids for Plant Transformation

Binary vectors such as pBinAR can be used for plant transformation (Höfgen and Willmitzer, Plant Science 66 (1990) 221-230). The binary vectors can be constructed by ligating the cDNA in sense or antisense orientation into T-DNA. 5' of the cDNA, a plant promoter activates cDNA transcription. A polyadenylation sequence is located 3' of the cDNA. Tissue specific expression can be achieved using a tissue specific promoter. For example, seed specific expression can be achieved by cloning in the napin or the LeB4 or the USP promoter 5' of the cDNA. Any other seed specific promoter element can also be used. The CaMV-35S promoter may be used for constitutive expression in all of the plants. In particular, genes encoding elongases and desaturases can be cloned into a binary vector by constructing a plurality of expression cassettes in succession in order to imitate the metabolic pathway in the plant.

Within an expression cassette, the protein expressed can be targeted into a cellular compartment using a signal peptide, for example for plastids, mitochondria or the endoplasmatic reticulum (Kermode, Crit. Rev. Plant Sci. 15, 4 (1996) 285-423). The signal peptide is cloned 5' in correct reading frame with the cDNA in order to achieve subcellular localization of the fusion protein.

Example 13

In Vivo Mutagenesis

The in vivo mutagenesis of microorganisms can be performed by passaging the plasmid DNA (or any other vector DNA) via *E. coli* or other microorganisms (for example *Bacillus* spp. or yeasts such as *Saccharomyces cerevisiae*), in which the ability of retaining the integrity of their genetic information is disrupted. Conventional mutator strains have mutations in the genes for the DNA repair system (for example mutHLS, mutD, mutT and the like; as reference, see Rupp, W. D. (1996) DNA repair mechanisms, in: *Escherichia coli* and *Salmonella*, pp. 2277-2294, ASM: Washington). These strains are known to the skilled worker. The use of these strains is illustrated for example in Greener, A., and Callahan, M. (1994) Strategies 7:32-34. Mutated DNA molecules are preferably transferred to plants after the microorganisms have been selected and tested. Transgenic plants are generated in accordance with various examples in the examples section of the present document.

Example 14

Studying the Expression of a Recombinant Gene Product in a Transformed Organism

The activity of a recombinant gene product in the transformed host organism was measured at the transcriptional and/or the translational level.

A suitable method for determining the amount of transcription of the gene (which indicates the amount of RNA available for translation of the gene product) is to carry out a northern blot as specified hereinbelow (for reference, see Ausubel et al. (1988) Current Protocols in Molecular Biology, Wiley: New York, or the abovementioned examples section) in which a primer which is designed such that it binds to the gene of interest is labeled with a detectable label (usually radioactivity or chemiluminescence) so that, when the total RNA of a culture of the organism is extracted, separated on a gel, transferred to a stable matrix and incubated with this probe, binding and the extent of binding of the probe indicates the presence as well as the quantity of the mRNA for this gene. This information indicates the degree of transcription of the transformed gene. Total cell RNA can be prepared from cells, tissues or organs by a plurality of methods, all of which are known in the art, such as, for example, the method of Bormann, E. R., et al. (1992) Mol. Microbiol. 6:317-326.

Northern Hybridization:

For the RNA hybridization, 20 µg of total RNA or 1 µg of poly(A)$^+$-RNA were separated by gel electrophoresis in 1.25% strength agarose gels using formaldehyde as described by Amasino (1986, Anal. Biochem. 152, 304), transferred to positively charged nylon membranes (Hybond N+, Amersham, Brunswick) by capillary attraction using 10×SSC, immobilized by UV light and prehybridized for 3 hours at 68° C. using hybridization buffer (10% dextran sulfate w/v, 1 M NaCl, 1% SDS, 100 mg herring sperm DNA). The DNA probe had been labeled with the Highprime DNA labeling kit (Roche, Mannheim, Germany) during the prehybridization stage using $\alpha$-$^{32}$P-dCTP (Amersham, Brunswick, Germany). The hybridization was carried out after adding the labeled DNA probe in the same buffer at 68° C. overnight. The wash steps were carried out twice for 15 minutes using 2×SSC and twice for 30 minutes using 1×SSC, 1% SDS, at 68° C. The sealed filters were exposed at −70° C. for a period of 1 to 14 days.

Standard techniques, such as a Western blot (see, for example, Ausubel et al. (1988) Current Protocols in Molecular Biology, Wiley: New York) can be employed for studying the presence or the relative quantity of protein translated by this mRNA. In this method, the total cell proteins are extracted, separated by means of gel electrophoresis, transferred to a matrix such as nitrocellulose and incubated with a probe such as an antibody which specifically binds to the desired protein. This probe is usually provided with a chemiluminescent or colorimetric label which can be detected readily. The presence and the quantity of the label observed indicates the presence and the quantity of the desired mutated protein which is present in the cell.

Example 15

Analysis of the Effect of the Recombinant Proteins on the Production of the Desired Product The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cell components for the increased production of the desired product (i.e. of lipids or a fatty acid). These analytical techniques are known to the skilled worker and encompass spectroscopy, thin layer chromatography, various staining methods, enzymatic and microbiological methods, and analytical chromatography such as high performance liquid chromatography (see, for example, Ullman, Encyclopedia of Industrial Chemistry, Vol. A2, pp. 89-90 and pp. 443-613, VCH Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III "Product recovery and purification", pp. 469-714, VCH Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J.A., and Henry, J. D. (1988) Biochemical Separations, in: Ullmann's Encyclopedia of Industrial Chemistry, Bd. B3; Chapter 11, Vol. 1-27, VCH Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940, and Browse et al. (1986) Analytic Biochemistry 152:141-145. Qualitative and quantitative lipid or fatty acid analysis is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press. Lipid Library; 1); "Progress in Lipid Research, Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for producing the desired compound, such as intermediates and byproducts, in order to determine the overall production efficiency of the compound. The analytical methods encompass measurements of the nutrient quantities in the medium (for example sugars, carbohydrates, nitrogen sources, phosphate and other ions), biomass composition and growth measurements, analysis of the production of customary metabolites of biosynthetic pathways, and measurements of gases which are generated during fermentation. Standard methods for these measurements are described in Applied Microbial Physiology; A Practical Approach, P. M. Rhodes and P. F. Stanbury, Ed., IRL Press, pp. 131-163 and 165-192 (ISBN: 0199635773) and references stated therein.

One example is the analysis of fatty acids (abbreviations: FAME, fatty acid methyl ester; GC-MS, gas liquid chromatography/mass spectrometry; TAG, triacylglycerol; TLC, thin layer chromatography).

The unambiguous detection of the presence of fatty acid products can be obtained by analyzing recombinant organisms by analytical standard methods: GC, GC-MS or TLC, as they are described on several occasions by Christie and the references therein (1997, in: Advances on Lipid Methodology, Fourth edition: Christie, Oily Press, Dundee, 119-169; 1998, gas chromatography/mass spectrometry methods, Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., ice cooled and recentrifuged followed by extraction in 0.5 M sulfuric acid in methanol with 2% dimethoxypropane for 1 hour at 90° C., which leads to hydrolyzed oil and lipid compounds which give transmethylated lipids. These fatty acid methyl esters are extracted in petroleum ether and finally subjected to GC analysis using a capillary column (Chrompack, WCOT Fused Silica, CP-Wax-52 CB, 25 µm, 0.32 mm) at a temperature gradient of between 170° C. and 240° C. for 20 minutes and 5 minutes at 240° C. The identity of the resulting fatty acid methyl esters must be defined using standards which are commercially available (i.e. Sigma).

In the case of fatty acids for which no standards are available, the identity must be demonstrated via derivatization followed by GC/MS analysis. For example, the localization of fatty acids with triple bond must be demonstrated via GC/MS following derivitization with 4,4-dimethoxyoxazolin derivatives (Christie, 1998, see above).

Example 16

Expression Constructs in Heterologous Microbial Systems

Strains, Growth Conditions and Plasmids

The *Escherichia coli* strain XL1 Blue MRF' kan (Stratagene) is used for subcloning the novel *Physcomitrella patens* elongases, such as PpPSE1. For functionally expressing this gene, we used the *Saccharomyces cerevisiae* strain INVSc 1 (Invitrogen Co.). *E. coli* is cultured at 37° C. in Luria Bertini broth (LB, Duchefa, Haarlem, the Netherlands). If necessary, ampicillin (100 mg/liter) is added, and 1.5% of agar (w/v) is added for solid LB media. *S. cerevisiae* is cultured at 30° C. either in YPG medium or in complete minimal medium without uracil (CMdum; see: Ausubel, F. M., Brent, R., Kingston, R. E., Moore, D. D., Seidman, J. G., Smith, J. A., Struhl, K., Albright, L. B., Coen, D. M., and Varki, A. (1995) Current Protocols in Molecular Biology, John Wiley & Sons, New York) together with 2% (w/v) of either raffinose or glucose. For solid media, 2% (w/v) of Bacto™ agar (Difco) are added. The plasmids used for cloning and expression are pUC18 (Pharmacia) and pYES2 (Invitrogen Co.).

Example 17

Cloning and Expression of PUFA Specific *Physcomitrella, Crypthecodinium* and *Thraustochytrium* elongases The full length genes of sequences according to the invention can be isolated as described in Example 7 and processed as illustrated hereinbelow. Concrete expression examples are shown with regard to the use.

a) Elongation of Fatty Acids by the Moss Elongase Pp_PSE1:

For expression in yeast, the *P. patens* cDNA clone PpPSE1 (earlier database sequence name: 08_ck19_b07, new name: pp001019019f), which encodes the PUFA specific elongase (PSE1) gene, was first modified in such a way that a BamHI restriction site and the yeast consensus sequence for highly effective translation (Kozak, M. (1986) Point mutations define a sequence flanking the AUG initiator codon that modulates translation by eukaryotic ribosomes, Cell 44, 283-292) was obtained next to the start codon and a BamHI restriction site was obtained which flanked the stop codon. To amplify the open reading frame, a primer pair which was complementary to its 5' and 3' ends was synthesized.

The gene of the sequence according to the invention shown in SEQ ID NO:1 was cloned into pYES by means of polymerase chain reaction, giving rise to the plasmid pYPp_PSE1:

The following oligonucleotides were employed for the PCR experiment:

```
Ppex6:   ggatccacataatggaggtcgtggagag (SEQ ID NO: 16)
         attc

Ppex6r:  ggatcctcactcagttttagctccttttt (SEQ ID NO: 17)
         gc
```

The PCR reaction was carried out with plasmid DNA of clone PP001019019F as matrix in a thermocycler (Biometra) with Pfu DNA (Stratagene) polymerase and the following temperature program: 3 minutes at 96° C. followed by 25 cycles with 30 seconds at 96° C., 30 seconds at 55° C. and 1 minute at 72° C., 1 cycle with 10 minutes at 72° C.

The correct size of the amplified DNA fragment was confirmed by agarose TBE gel electrophoresis. The amplified DNA was extracted from the gel using the QIAquick gel extraction kit (QIAGEN) and initially cloned into pUC18 using the Sure Clone Ligation Kit (Pharmacia). The fragment cloned thus was cut with BamHI and ligated into pYES, giving rise to pYPp_PSE1. The fragment orientation was checked by means of HindIII. Following the transformation of *E. coli* XL1 Blue MRF' kan, a DNA minipreparation (Riggs, M. G., & McLachlan, A. (1986) A simplified screening procedure for large numbers of plasmid mini preparation. BioTechniques 4, 310-313) of transformants was carried out, and positive clones were identified by means of BamHI restriction analysis. The sequence of the cloned PCR product was confirmed by resequencing using the ABI PRISM Big Dye Terminator Cycle Sequencing Ready Reaction Kit (Perkin-Elmer, Weiterstadt).

One clone was grown with the Nucleobond® AX 500 plasmid DNA extraction kit (Macherey Nagel, Düringen) for the DNA maxipreparation.

*Saccharomyces* INVSc1 was transformed with pYPp_PSE1 or with pYES2 as control by means of a modified PEG/lithium acetate protocol (Ausubel et al., 1995). Following selection on CMdum agar plates with 2% glucose, transformants and a pYES2 transformant were selected for further cultivation and functional expression as already stated and fed various fatty acids in the medium.

i) Lipid patterns of yeasts which are transformed with the pYES plasmid without fragment insertion or which express the Pp-PSE1 gene (data in mol %) after feeding with 250 µm hexadecatrienoic acid ($16:3^{\Delta 7c,10c,13c}$).

TABLE 4

| PYES2 | PYES2 | pYPp_PSE1 | PYPp_PSE1 |
|---|---|---|---|
| 16:0 | 11.8% | 16:0 | 11.1% |
| 16:1 | 28.7% | 16:1 | 23.9% |
| 16:3$^{\Delta 7c,10c,13c}$ | 9.2% | 16:3$^{\Delta 7c,10c,13c}$ | 12.0% |
| 18:0 | 10.6% | 18:0 | 8.6% |
| 18:1$^{\Delta 9c}$ | 34.9% | 18:1$^{\Delta 9c}$ | 20.6% |
| 18:1$^{\Delta 11c}$ | 1.1% | 18:1$^{\Delta 11c}$ | 1.4% |
| 18:3$^{\Delta 9c,12c,15c}$ | 3.7% | 18:3$^{\Delta 9c,12c,15c}$ | 21.4% | ii) Lipid patterns of yeasts which are transformed with the pYES plasmid without fragment insertion or which express the Pp-PSE1 gene (data in mol %) after feeding with 500 μm pinolenic acid (18:3$^{\Delta 6c,9c,12c}$).

TABLE 5

| PYES2 | PYES2 | pYPp_PSE1 | PYPp_PSE1 |
|---|---|---|---|
| 16:0 | 18.3% | 16:0 | 16.9% |
| 16:1$^{\Delta 9c}$ | 16.0% | 16:1$^{\Delta 9c}$ | 15.3% |
| 18:0 | 8.6% | 18:0 | 8.4% |
| 18:1$^{\Delta 9c}$ | 16.7% | 18:1$^{\Delta 9c}$ | 17.5% |
| 18:1$^{\Delta 11c}$ | 0.7% | 18:1$^{\Delta 11c}$ | 2.0% |
| 18:3$^{\Delta 5c,9c,12c}$ | 39.8% | 18:3$^{\Delta 5c,9c,12c}$ | 32.6% |
| 20:3$^{\Delta 7c,11c,14c}$ | 0% | 20:3$^{\Delta 7c,11c,14c}$ | 5.1% | iii) Lipid patterns of yeasts which are transformed with the pYES plasmid without fragment insertion or which express the Pp-PSE1 gene (data in mol %) after feeding with 500 μm stearidonic acid (18:4$^{\Delta 6c,9c,12c,15c}$).

TABLE 6

| PYES2 | pYES2 | pYPp_PSE1 | PYPp_PSE1 |
|---|---|---|---|
| 16:0 | 15.2% | 16:0 | 15.6% |
| 16:1$^{\Delta 9c}$ | 13.1% | 16:1$^{\Delta 9c}$ | 14.9% |
| 18:0 | 12.3% | 18:0 | 10.7% |
| 18:1$^{\Delta 9c}$ | 12.9% | 18:1$^{\Delta 9c}$ | 14.0% |
| 18:1$^{\Delta 11c}$ | 0.7% | 18:1$^{\Delta 11c}$ | 1.2% |
| 18:3$^{\Delta 6c,9c,12c,15c}$ | 45.4% | 18:3$^{\Delta 6c,9c,12c,15c}$ | 23.8% |
| 20:4$^{\Delta 8c,11c,14c,17c}$ | 0.4% | 20:4$^{\Delta 8c,11c,14c,17c}$ | 19.8% | iv) Lipid patterns of yeasts which are transformed with the pYES plasmid without fragment insertion or which express the Pp-PSE1 gene (data in mol %) after feeding with 500 μm linoleic acid (18:2$^{\Delta 9c,12c}$).

TABLE 7

| pYES2 | pYES2 | pYPp_PSE1 | PYPp_PSE1 |
|---|---|---|---|
| 16:0 | 7.9% | 16:0 | 8.7% |
| 16:1$^{\Delta 9c}$ | 1.2% | 16:1$^{\Delta 9c}$ | 1.3% |
| 18:0 | 5.3% | 18:0 | 5.1% |
| 18:1$^{\Delta 9c}$ | 1.3% | 18:1$^{\Delta 9c}$ | 1.3% |
| 18:2$^{\Delta 9c,12c}$ | 83.9% | 18:2$^{\Delta 9c,12c}$ | 80.4% |
| 20:2$^{\Delta 11c,14c}$ | 0.5% | 20:2$^{\Delta 11c,14c}$ | 3.2% |

B) Elongation of Fatty Acids by a *Thraustochytrium* elongase

For expression in yeast, the *Thraustochytrium* cDNA clone of SEQ ID NO: 3 (Tc_PSE2), which encodes a PUFA-specific elongase (PSE) gene, is first modified in such a way that it constitutes a functionally active polypeptide. To this end, the N-terminus of the protein is elongated at DNA level by 42 base pairs by the few missing bases from the *Physcomitrella patens* elongase. However, it is also possible only to add a start codon in the correct reading frame for the sequence.

The following oligonucleotides are employed for the PCR experiment:

```
pTCPSE2-5':
aaaggatccacataatggaggtcgtggagagattctacggtgagttggatggga
agGTCATTTCGGGCCTCGACC (SEQ ID NO: 18)
pTCPSE2-3': aaggatccctgagttttagctcccttttgctttcc (SEQ ID NO: 19)
```

In addition, both oligonucleotides contain a BamHI restriction site and the yeast consensus sequence for highly efficient translation (Kozak, M. (1986) Point mutations define a sequence flanking the AUG initiator codon that modulates translation by eukaryotic ribosomes, Cell 44, 283-292).

The PCR reaction is carried out with plasmid DNA as matrix in a thermocycler (Biometra) with Pfu DNA (Stratagene) polymerase and the following temperature program: 3 minutes at 96° C. followed by 25 cycles with 30 seconds at 96° C., 30 seconds at 55° C. and 3 minutes at 72° C., 1 cycle with 10 minutes at 72° C. and stop at 4° C.

The correct size of the amplified DNA fragment is confirmed by agarose TBE gel electrophoresis. The amplified DNA is extracted from the gel using the QIAquick gel extraction kit (QIAGEN) and ligated into the Sinai restriction site of the dephosphorylated vector pUC18 using the Sure Clone Ligation Kit (Pharmacia), giving rise to pUC-hybrid-Tc_PSE2. Following the transformation of *E. coli* XL1 Blue MRF' kan, a DNA minipreparation (Riggs, M. G., & McLachlan, A. (1986) A simplified screening procedure for large numbers of plasmid mini-preparation. BioTechniques 4, 310-313) of 24 ampicillin-resistant transformants was carried out, and positive clones were identified by means of BamHI restriction analysis. The sequence of the cloned PCR product was confirmed by resequencing using the ABI PRISM Big Dye Terminator Cycle Sequencing Ready Reaction Kit (Perkin-Elmer, Weiterstadt).

The plasmid DNA of pUC PSE1 and pUC-hybrid-Tc_PSE2 was first cleaved with BamHI and the fragments obtained were ligated into the BamHI restriction site of the dephosphorylated yeast/*E. coli* shuttle vector pYES2, giving rise to pY2 hybrid-Tc_PSE2. Following transformation of *E. coli* and DNA minipreparation from the transformants, the orientation of the DNA fragment in the vector was checked by cleavage with HindIII. One clone was grown with the Nucleobond® AX 500 plasmid DNA extraction kit (Macherey-Nagel, Düringen) for the DNA maxipreparation. *Saccharomyces* INVSc1 is transformed with pY2PSE1, pYES2, pY2-hybrid-Tc_PSE2 and pYES2 by means of a modified PEG/lithium acetate protocol (Ausubel et al., 1995). Following selection on CMdum agar plates with 2% glucose, in each case four pY2PSE1 transformants (pY2PSE1a-d), pY2-hybrid-Tc_PSE2 transformants (pY2-hybrid-Tc_PSE2 1a-d) and one pYES2 transformant are selected for further culture and functional expression.

Functional Expression of an Elongase Activity in Yeast
Preculture:

20 ml of CMdum liquid medium with 2% (w/v) raffinose were inoculated with the transgenic yeast clones (pY2-hybrid-Tc_PSE2 1a-d, pYES2) and cultured for 3 days at 30° C., 200 rpm, until an optical density at 600 nm (OD$_{600}$) of 1.5-2 had been reached.

Main Culture:

For expression, 20 ml of CMdum liquid medium with 2% raffinose and 1% (v/v) Tergitol NP 40 were supplemented with fatty acid substrates to a final concentration of 0.003% (w/v). The media are inoculated with the precultures to an OD$_{600}$ of 0.05. Expression was induced for 16 hours at an $OD_{600}$ of 0.2, using 2% (w/v) galactose, whereupon the cultures were harvested at an $OD_{600}$ of 0.8-1.2.

Fatty Acid Analysis

The overall fatty acids were extracted from yeast cultures and analyzed by means of gas chromatography. To this end, cells of 5 ml culture were harvested by centrifugation (1000× g, 10 minutes, 4° C.) and washed once with 100 mM $NaHCO_3$, pH 8.0, to remove residual medium and fatty acids. To prepare the fatty acid methyl esters (FAMEs), the cell sediments were treated for 1 hour at 80° C. with 1 M methanolic $H_2SO_4$ and 2% (v/v) dimethoxypropane. The FAMEs were extracted twice with 2 ml of petroleum ether, washed once with 100 mM $NaHCO_3$, pH 8.0, and once with distilled water, and dried with $Na_2SO_4$. The organic solvent was evaporated under a stream of argon, and the FAMEs were dissolved in 50 µl petroleum ether. The samples were separated on a ZEBRON ZB Wax capillary column (30 m, 0.32 mm, 0.25 µm; Phenomenex) in a Hewlett Packard 6850 gas chromatograph equipped with a flame ionization detector. The oven temperature was programmed from 70° C. (hold for 1 minute) to 200° C. at a rate of 20° C./minute, then to 250° C. (hold for 5 minutes) at a rate of 5° C./minute and finally to 260° C. at a rate of 5° C./minute. Nitrogen was used as the carrier gas (4.5 ml/minute at 70° C.). The fatty acids were identified by comparison with retention times of FAME standards (SIGMA).

The fatty acid patterns of five transgenic yeast strains are shown in Table 1 in mol %.

The ratios of the γ-linolenic acid which had been added and taken up are emphasized by numbers printed in bold, those of the elongated products by numbers in red and those of the elongated γ-linolenic acid by numbers printed in bold (last line).

Figure 2B:
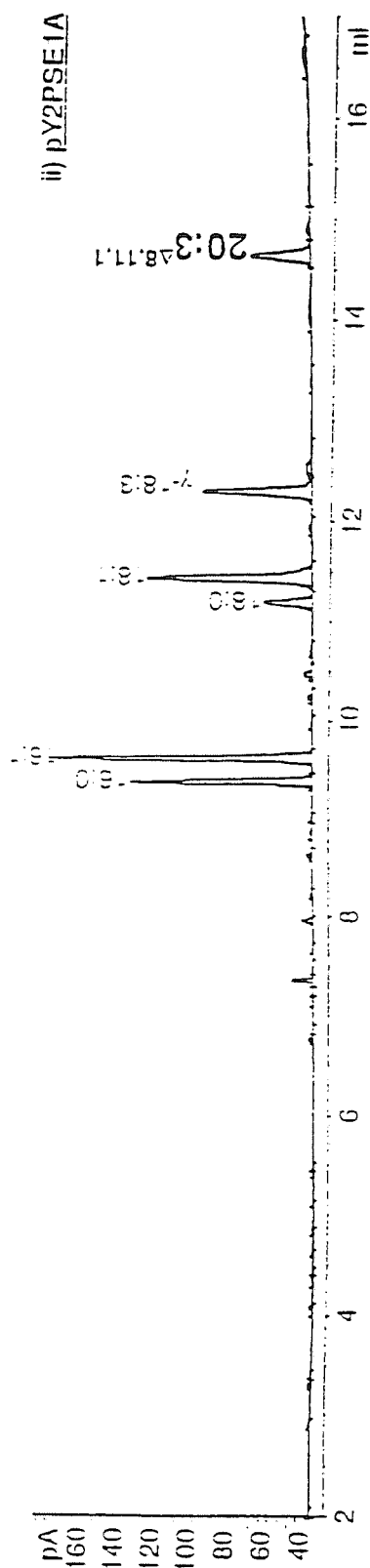
Figure 2C:
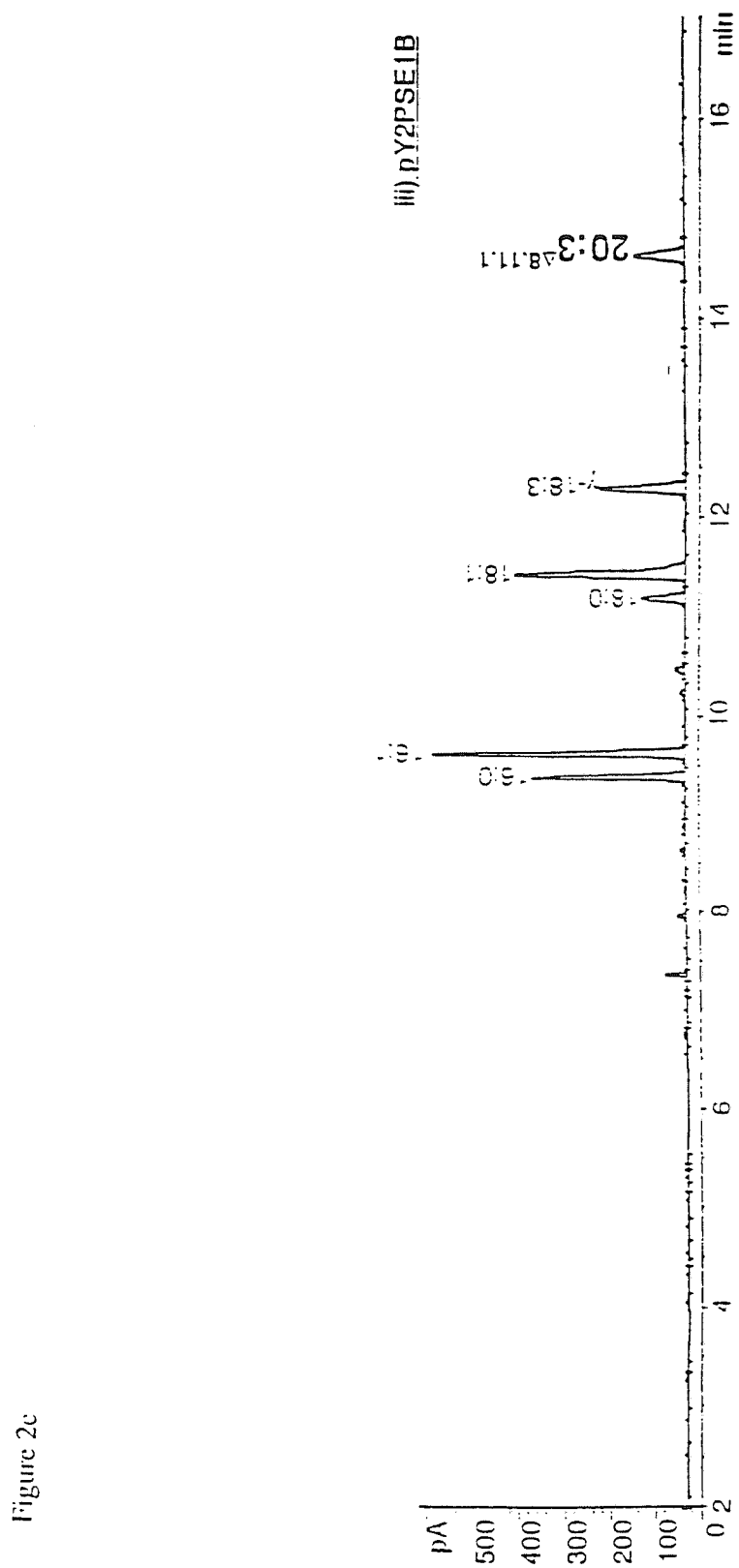
Figure 2D:
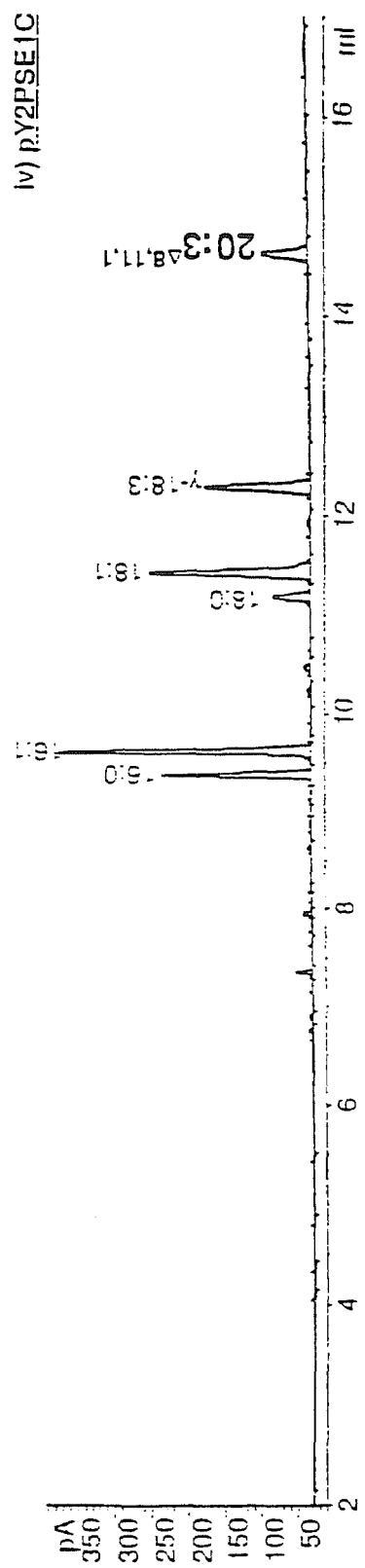
Figure 2E:
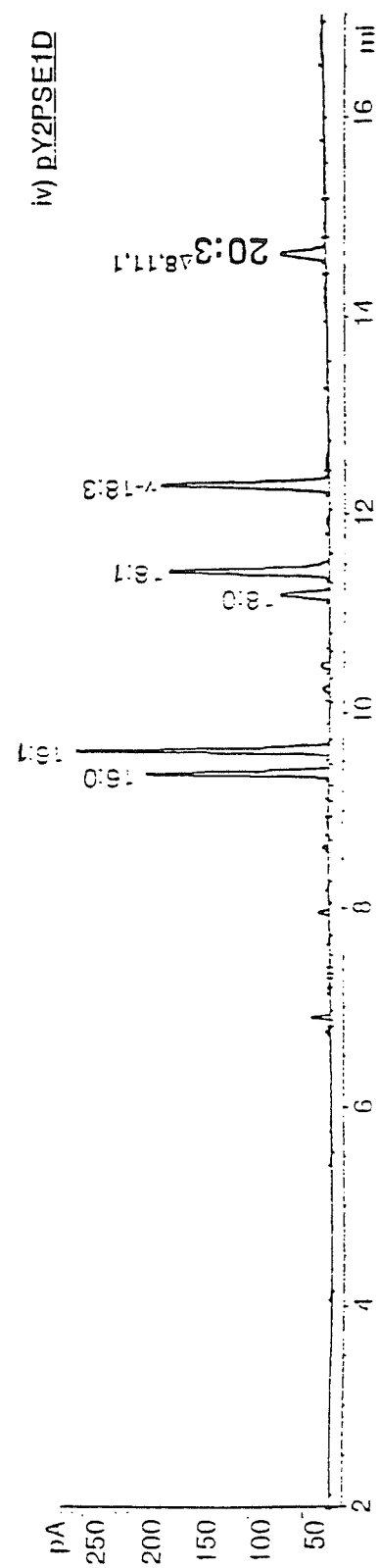

The GC analysis of FAMEs which from total lipids of the yeasts transformed with pYES2 (i/control) and pY2PSE1 (ii-iv c+d/ in each case transformed with pY2PSE1A, pY2PSE1B, pY2PSE1C, pY2PSE1D) is shown in FIG. 2a-e. For the analysis, the transgenic yeasts were cultured in the presence of γ-18:3. Table 1 shows their fatty acid patterns in mol %. The uptake of γ-18:3 is emphasized by numbers printed in bold, the elongation product dihomo-γ-linolenic acid (20:3Δ8,11,14) is underlined and the ratio γ-18:3 elongation product (also in mol %) is emphasized by numbers printed in bold (last line). The structure and the mass spectra of the DMOX derivative of cis-Δ6,9,12 C18:3 can be seen from FIG. 3a+b. The structure and the mass spectra of the DMOX derivative of Δ8,11,14 C20:3 can be seen from FIG. 4a+b.

The results demonstrate that γ-18:3 has been incorporated into all transgenic yeasts in large amounts. All four transgenic yeast clones which had been transformed with pY2PSE1 exhibit an additional peak in the gas chromatogram, which was identified as 20:3 Δ8,11,14 by a comparison of the retention times. A gas chromatography/mass spectroscopy can provide additional proof to confirm this identity. The percentage of elongated γ-18:3 was 23.7 to 40.5%, as shown in Table 1. Furthermore, no significant elongation of palmitic acid (16:0), palmitoleic acid (16:1), stearic acid (18:0) or oleic acid (18:1 Δ9) was observed.

The products identified demonstrate that the nucleotide sequence of PpPSE1 encodes a Δ6-selective fatty acid elongase from the moss *Physcomitrella patens*, which leads to the formation of novel fatty acids in transgenic yeasts.

The ratios of the fatty acid substrates which have been added and taken up can be determined as above, so that quantity and quality of the elongase reaction can be detected.

The structure and the mass spectra of DMOX derivatives also reveal the respective position of a double bond.

Further feeding experiments with a wide range of other fatty acids (for example arachidonic acid, eicosapentaenoic acid and the like) can be carried out for confirming the substrate selectivity of this elongase in greater detail.

Example 18

Isolation of the Desired Product from Transformed or Organisms in General

The desired product can be obtained from plant material or fungi, algae, ciliates, animal cells or from the supernatant of the above described cultures by various methods known in the art. If the desired product is not secreted from the cells, the cells can be harvested from the culture by slow centrifugation, and the cells can be lyzed by standard techniques, such as mechanical force or sonication. Plant organs can be separated mechanically from other tissue or other organs. After homogenization, the cell debris is removed by centrifugation, and the supernatant fraction, which contains the soluble proteins, is retained for further isolating the desired compound. If the product is secreted from desired cells, the cells are removed from the culture by slow centrifugation, and the supernatant fraction is retained for the further isolation.

The supernatant fraction from each isolation step is subjected to a chromatography with a suitable resin, the desired molecule either being retained on the chromatography resin while many contaminants in the sample are not, or the contaminants remaining on the resin while the sample does not. These chromatography steps can be repeated, if desired, using either the same or other chromatography resins. The skilled worker is familiar with selecting suitable chromatography resins and with their most effective use for a particular molecule to be isolated. The product isolated can be concentrated by filtration or ultrafiltration and stored at a temperature at which the stability of the product is highest.

A broad spectrum of isolation methods is known in the art, and the isolation method above is not intended to be limiting. These isolation methods are described, for example, in Bailey, J. E., & Ollis, D. F., Biochemical Engineering Fundamentals, McGraw Hill: New York (1986).

Identity and purity of the compounds isolated can be determined by standard techniques of the art. They include high performance liquid chromatography (HPLC), spectroscopic methods, staining methods, thin layer chromatography, NIRS, enzyme assays or microbiological methods. For a review of these analytical methods, see: Patek et al. (1994) Appl. Environ. Microbiol. 60:133-140; Malakhova et al. (1996) Biotekhnologiya 11:27-32; and Schmidt et al. (1998) Bioprocess Engineer. 19:67-70. Ulmann's Encyclopedia of Industrial Chemistry (1996) Vol. A27, VCH Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A., et al. (1987) Applications of HPLC in Biochemistry in: Laboratory Techniques in Biochemistry and Molecular Biology, Vol. 17.

EQUIVALENTS

The skilled worker knows, or can identify, a number of equivalents of the specific embodiments according to the invention which have been described herein by simply resorting to routine experiments. These equivalents are intended to be covered by the patent claims.

We claim:

1. A gene construct having a heterologous promoter or a vector comprising an isolated nucleic acid sequence encoding a polypeptide functionally linked to one or more regulatory signals, wherein the isolated nucleic acid sequence comprises a derivative of SEQ ID NO: 1, and the polypeptide elongates $C_{18}$-fatty acids with at least two double bonds in the fatty acid molecule, and wherein the polypeptide is selected from the group consisting of
   i) polypeptides having the amino acid sequence of SEQ ID NO:2, and
   ii) polypeptides having an amino acid sequence with at least 80% identity at the amino acid level with SEQ ID NO:2 having elongase activity.

2. The gene construct or vector of claim 1, wherein the isolated nucleic acid sequence is derived from *Physcomitrella*.

3. The gene construct or vector as claimed in claim 1, further comprising
   a nucleic acid sequence which encodes a fatty acid biosynthesis gene.

4. The gene construct or vector as claimed in claim 2, wherein the nucleic acid which encodes a fatty acid biosynthesis gene is selected from the group consisting of: Δ19-, Δ17-, Δ15-, Δ12-, Δ9-, Δ8-, Δ6-, Δ5-, Δ4-desaturase, hydroxylases, Δ12-acetylenase, acyl-ACP thioesterases, β-ketoacyl-ACP synthases and β-ketoacyl-ACP reductases.

5. An organism other than a human comprising the isolated nucleic acid sequence introduced by the gene construct or vector as claimed in claim 1.

6. The organism as claimed in claim 5, wherein the organism is a microorganism, yeast or a plant.

7. The organism as claimed in claim 5, wherein the organism is a transgenic plant.

8. A process for the preparation of a PUFA, which comprises culturing an organism comprising the isolated nucleic acid sequence introduced by the gene construct or vector of claim 1 under conditions under which PUFAs are formed in the organism.

9. The process as claimed in claim 8, wherein the PUFA is a $C_{18}$-fatty acid molecule with at least two double bonds in the fatty acid molecule.

10. The process as claimed in claim 9, wherein the $C_{18}$-fatty acid molecule is isolated from the organism in the form of an oil, lipid or a free fatty acid.

11. The process as claimed in claim 8, wherein the organism is a microorganism, an animal or a plant.

12. The process as claimed in claim 8, wherein the organism is a transgenic plant.

13. The process as claimed in claim 8, wherein the $C_{18}$-fatty acid is a fatty acid with three double bonds in the molecule.

14. A kit comprising the gene construct or vector comprising said isolated nucleic acid sequence of claim 1.

15. The gene construct or vector as claimed in claim 1 wherein the isolated nucleic acid sequence is derived from a plant.

16. A gene construct of claim 1, wherein gene expression is enhanced by said regulatory signals.

17. The gene construct or vector of claim 1, wherein the polypeptide having at least 80% identity at the amino acid level with SEQ ID NO:2 contains motifs FLHVYHH, corresponding to amino acids 158 to 164 of SEQ ID NO: 2 which is optionally substituted in the first, third, fourth and fifth positions position with T, Q, W, L respectively, LMYAYYF, corresponding to amino acids 196 to 202 of SEQ ID NO: 2 which is optionally substituted in the first, fourth, fifth, and sixth, position with I, M, H, F respectively, and FGNFYVQ, corresponding to amino acids 268 to 274 of SEQ ID NO: 2 which is optionally substituted in the second and seventh position with L.

18. The gene construct or vector of claim 1, wherein the polypeptide is selected from the groups consisting of
   i) polypeptides having the amino acid sequence of SEQ ID NO:2, and
   ii) polypeptides having an amino acid sequence with at least 95% identity at the amino acid level with SEQ ID NO:2 having elongase activity.

19. The gene construct or vector of claim 1, wherein the polypeptide elongates 6,9-octadecadienoic acid, linoleic acid, linolenic acid, α- or γ-linolenic acid, pinolenic acid or stearidonic acid.

* * * * *

SEQUENCE LISTING

<160> NUMBER OF SEQ ID NOS: 19

<210> SEQ ID NO 1
<211> LENGTH: 1192
<212> TYPE: DNA
<213> ORGANISM: Physcomitrella patens
<220> FEATURE:
<221> NAME/KEY: CDS
<222> LOCATION: (58)..(930)

<400> SEQUENCE: 1

```
ctgcttcgtc tcatcttggg ggtgtgattc gggagtgggt tgagttggtg gagcgca            57 atg gag gtc gtg gag aga ttc tac ggt gag ttg gat ggg aag gtc tcg          105
Met Glu Val Val Glu Arg Phe Tyr Gly Glu Leu Asp Gly Lys Val Ser
  1               5                  10                  15 cag ggc gtg aat gca ttg ctg ggt agt ttt ggg gtg gag ttg acg gat          153
Gln Gly Val Asn Ala Leu Leu Gly Ser Phe Gly Val Glu Leu Thr Asp
             20                  25                  30 acg ccc act acc aaa ggc ttg ccc ctc gtt gac agt ccc aca ccc atc          201
Thr Pro Thr Thr Lys Gly Leu Pro Leu Val Asp Ser Pro Thr Pro Ile
         35                  40                  45 gtc ctc ggt gtt tct gta tac ttg act att gtc att gga ggg ctt ttg          249
Val Leu Gly Val Ser Val Tyr Leu Thr Ile Val Ile Gly Gly Leu Leu
     50                  55                  60 tgg ata aag gcc agg gat ctg aaa ccg cgc gcc tcg gag cca ttt ttg          297
Trp Ile Lys Ala Arg Asp Leu Lys Pro Arg Ala Ser Glu Pro Phe Leu
 65                  70                  75                  80 ctc caa gct ttg gtg ctt gtg cac aac ctg ttc tgt ttt gcg ctc agt          345
Leu Gln Ala Leu Val Leu Val His Asn Leu Phe Cys Phe Ala Leu Ser
                 85                  90                  95 ctg tat atg tgc gtg ggc atc gct tat cag gct att acc tgg cgg tac          393
Leu Tyr Met Cys Val Gly Ile Ala Tyr Gln Ala Ile Thr Trp Arg Tyr
            100                 105                 110 tct ctc tgg ggc aat gca tac aat cct aaa cat aaa gag atg gcg att          441
Ser Leu Trp Gly Asn Ala Tyr Asn Pro Lys His Lys Glu Met Ala Ile
        115                 120                 125 ctg gta tac ttg ttc tac atg tct aag tac gtg gaa ttc atg gat acc          489
Leu Val Tyr Leu Phe Tyr Met Ser Lys Tyr Val Glu Phe Met Asp Thr
    130                 135                 140 gtt atc atg ata ctg aag cgc agc acc agg caa ata agc ttc ctc cac          537
Val Ile Met Ile Leu Lys Arg Ser Thr Arg Gln Ile Ser Phe Leu His
145                 150                 155                 160 gtt tat cat cat tct tca att tcc ctc att tgg tgg gct att gct cat          585
Val Tyr His His Ser Ser Ile Ser Leu Ile Trp Trp Ala Ile Ala His
                165                 170                 175 cac gct cct ggc ggt gaa gca tat tgg tct gcg gct ctg aac tca gga          633
His Ala Pro Gly Gly Glu Ala Tyr Trp Ser Ala Ala Leu Asn Ser Gly
            180                 185                 190 gtg cat gtt ctc atg tat gcg tat tac ttc ttg gct gcc tgc ctt cga          681
Val His Val Leu Met Tyr Ala Tyr Tyr Phe Leu Ala Ala Cys Leu Arg
        195                 200                 205 agt agc cca aag tta aaa aat aag tac ctt ttt tgg ggc agg tac ttg          729
Ser Ser Pro Lys Leu Lys Asn Lys Tyr Leu Phe Trp Gly Arg Tyr Leu
    210                 215                 220 aca caa ttc caa atg ttc cag ttt atg ctg aac tta gtg cag gct tac          777
Thr Gln Phe Gln Met Phe Gln Phe Met Leu Asn Leu Val Gln Ala Tyr
225                 230                 235                 240 tac gac atg aaa acg aat gcg cca tat cca caa tgg ctg atc aag att          825
Tyr Asp Met Lys Thr Asn Ala Pro Tyr Pro Gln Trp Leu Ile Lys Ile
                245                 250                 255
```

```
ttg ttc tac tac atg atc tcg ctg ttt ctt ttc ggc aat ttt tac       873
Leu Phe Tyr Tyr Met Ile Ser Leu Leu Phe Leu Phe Gly Asn Phe Tyr
            260                 265                 270 gta caa aaa tac atc aaa ccc tct gac gga aag caa aag gga gct aaa   921
Val Gln Lys Tyr Ile Lys Pro Ser Asp Gly Lys Gln Lys Gly Ala Lys
        275                 280                 285 act gag tga gctgtatcaa gccatagaaa ctctattatg ttagaacctg           970
Thr Glu
    290 aagttggtgc tttcttatct ccacttatct tttaagcagc atcagttttg aaatgatgtg  1030 tgggcgtggt ctgcaagtag tcatcaatat aatcggcctg agcacttcag atggattgtt  1090 agaacatgag taaaagcggt tattacggtg tttattttgt accaaatcac cgcacgggtg  1150 aattgaaata tttcagattt gatcaatttc atctgaaaaa aa                    1192

<210> SEQ ID NO 2
<211> LENGTH: 290
<212> TYPE: PRT
<213> ORGANISM: Physcomitrella patens

<400> SEQUENCE: 2
```

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

```
Val Gln Lys Tyr Ile Lys Pro Ser Asp Gly Lys Gln Lys Gly Ala Lys
            275                 280                 285

Thr Glu
    290

<210> SEQ ID NO 3
<211> LENGTH: 687
<212> TYPE: DNA
<213> ORGANISM: Thraustochytrium
<220> FEATURE:
<221> NAME/KEY: CDS
<222> LOCATION: (1)..(588)

<400> SEQUENCE: 3 cgc agc gtg cat aac ctc ggg ctc tgc ctc ttc tcg ggc gcc gtg tgg      48
Arg Ser Val His Asn Leu Gly Leu Cys Leu Phe Ser Gly Ala Val Trp
  1               5                  10                  15 atc tac acg agc tac ctc atg atc cag gat ggg cac ttt cgc agc ctc      96
Ile Tyr Thr Ser Tyr Leu Met Ile Gln Asp Gly His Phe Arg Ser Leu
                 20                  25                  30 gag gcg gca acg tgc gag ccg ctc aag cat ccg cac ttc cag ctc atc     144
Glu Ala Ala Thr Cys Glu Pro Leu Lys His Pro His Phe Gln Leu Ile
             35                  40                  45 agc ttg ctc ttt gcg ctg tcc aag atc tgg gag tgg ttc gac acg gtg     192
Ser Leu Leu Phe Ala Leu Ser Lys Ile Trp Glu Trp Phe Asp Thr Val
         50                  55                  60 ctc ctc atc gtc aag ggc aac aag ctc cgc ttc ctg cac gtc ttg cac     240
Leu Leu Ile Val Lys Gly Asn Lys Leu Arg Phe Leu His Val Leu His
 65                  70                  75                  80 cac gcc acg acc ttt tgg ctc tac gcc atc gac cac atc ttt ctc tcg     288
His Ala Thr Thr Phe Trp Leu Tyr Ala Ile Asp His Ile Phe Leu Ser
                 85                  90                  95 tcc atc aag tac ggc gtc gcg gtc aat gct ttc atc cac acc gtc atg     336
Ser Ile Lys Tyr Gly Val Ala Val Asn Ala Phe Ile His Thr Val Met
                100                 105                 110 tac gcg cac tac ttc cgc cca ttc ccg aag ggc ttg cgc ccg ctt att     384
Tyr Ala His Tyr Phe Arg Pro Phe Pro Lys Gly Leu Arg Pro Leu Ile
            115                 120                 125 acg cag ttg cag atc gtc cag ttc atc ttc agc atc ggc atc cat acc     432
Thr Gln Leu Gln Ile Val Gln Phe Ile Phe Ser Ile Gly Ile His Thr
        130                 135                 140 gcc atc tac tgg cac tac gac tgc gag ccg ctc gtg cat acc cac ttt     480
Ala Ile Tyr Trp His Tyr Asp Cys Glu Pro Leu Val His Thr His Phe
145                 150                 155                 160 tgg gaa tac gtc acg ccc tac ctc ttc gtc gtg ccc ttc ctc atc ctc     528
Trp Glu Tyr Val Thr Pro Tyr Leu Phe Val Val Pro Phe Leu Ile Leu
                165                 170                 175 ttt ctc aat ttc tac ctg cag cag tac gtc ctc gcg ccc gca aaa acc     576
Phe Leu Asn Phe Tyr Leu Gln Gln Tyr Val Leu Ala Pro Ala Lys Thr
                180                 185                 190 aag aag gca tag ccacgtaaca gtagaccagc agcgccgagg acgcgtgccg          628
Lys Lys Ala
        195 cgttatcgcg aagcacgaaa taagaagat catttgattc aaaaaaaaaa aaaaaaaa      687

<210> SEQ ID NO 4
<211> LENGTH: 195
<212> TYPE: PRT
<213> ORGANISM: Thraustochytrium

<400> SEQUENCE: 4
```

-continued

```
Arg Ser Val His Asn Leu Gly Leu Cys Leu Phe Ser Gly Ala Val Trp
 1               5                  10                  15

Ile Tyr Thr Ser Tyr Leu Met Ile Gln Asp Gly His Phe Arg Ser Leu
             20                  25                  30

Glu Ala Ala Thr Cys Glu Pro Leu Lys His Pro His Phe Gln Leu Ile
         35                  40                  45

Ser Leu Leu Phe Ala Leu Ser Lys Ile Trp Glu Trp Phe Asp Thr Val
     50                  55                  60

Leu Leu Ile Val Lys Gly Asn Lys Leu Arg Phe Leu His Val Leu His
 65                  70                  75                  80

His Ala Thr Thr Phe Trp Leu Tyr Ala Ile Asp His Ile Phe Leu Ser
                 85                  90                  95

Ser Ile Lys Tyr Gly Val Ala Val Asn Ala Phe Ile His Thr Val Met
            100                 105                 110

Tyr Ala His Tyr Phe Arg Pro Phe Pro Lys Gly Leu Arg Pro Leu Ile
        115                 120                 125

Thr Gln Leu Gln Ile Val Gln Phe Ile Phe Ser Ile Gly Ile His Thr
    130                 135                 140

Ala Ile Tyr Trp His Tyr Asp Cys Glu Pro Leu Val His Thr His Phe
145                 150                 155                 160

Trp Glu Tyr Val Thr Pro Tyr Leu Phe Val Val Pro Phe Leu Ile Leu
                165                 170                 175

Phe Leu Asn Phe Tyr Leu Gln Gln Tyr Val Leu Ala Pro Ala Lys Thr
            180                 185                 190

Lys Lys Ala
        195

<210> SEQ ID NO 5
<211> LENGTH: 955
<212> TYPE: DNA
<213> ORGANISM: Thaustochytrium
<220> FEATURE:
<221> NAME/KEY: CDS
<222> LOCATION: (1)..(894)

<400> SEQUENCE: 5 gtc att tcg ggc ctc gac ctt ctc ccc gtg ctc tcg tgg gag act atg      48
Val Ile Ser Gly Leu Asp Leu Leu Pro Val Leu Ser Trp Glu Thr Met
 1               5                  10                  15 aag ttc gac act gcc gaa gtt gtc tcg gtc tgg ctg cgc acg cac atg      96
Lys Phe Asp Thr Ala Glu Val Val Ser Val Trp Leu Arg Thr His Met
             20                  25                  30 tgg gtc ccc ttc ctg atg tgc ttc atc tac ctg gtc gtc atc ttc ggc     144
Trp Val Pro Phe Leu Met Cys Phe Ile Tyr Leu Val Val Ile Phe Gly
         35                  40                  45 atc cag tac tac atg gag gac cgc aag gag ttc gat ctg cgc aag ccg     192
Ile Gln Tyr Tyr Met Glu Asp Arg Lys Glu Phe Asp Leu Arg Lys Pro
     50                  55                  60 ctg gcc gcc tgg agc gcc ttc ttg gcc att ttc agc atc ggc gcc tcc     240
Leu Ala Ala Trp Ser Ala Phe Leu Ala Ile Phe Ser Ile Gly Ala Ser
 65                  70                  75                  80 atc cgc acc gtg ccc gtc ctg ctc aag atg ctc tac gaa aag ggc acg     288
Ile Arg Thr Val Pro Val Leu Leu Lys Met Leu Tyr Glu Lys Gly Thr
                 85                  90                  95 cac cac gtg ctc tgc ggc gac acg cgc aac gac tgg gtc att gac aac     336
His His Val Leu Cys Gly Asp Thr Arg Asn Asp Trp Val Ile Asp Asn
            100                 105                 110 ccg gcc ggc gtc tgg acc atg gcc ttt atc ttt tcc aag att ccc gag     384
Pro Ala Gly Val Trp Thr Met Ala Phe Ile Phe Ser Lys Ile Pro Glu
```

```
                                          -continued

Pro Ala Gly Val Trp Thr Met Ala Phe Ile Phe Ser Lys Ile Pro Glu
                115                 120                 125 ctc atc gac acc ctc ttt atc gtg ctc cgc aag cgc aag ctc atc acc    432
Leu Ile Asp Thr Leu Phe Ile Val Leu Arg Lys Arg Lys Leu Ile Thr
130                 135                 140 ctc cac tgg tac cac cac gtg acc gtg ctc ctg ttc tgc tgg cac gcc    480
Leu His Trp Tyr His His Val Thr Val Leu Leu Phe Cys Trp His Ala
145                 150                 155                 160 tgg gcc acc ttt gcg ctc acc ggc atc gtc ttt gcc gcc atc aac gcc    528
Trp Ala Thr Phe Ala Leu Thr Gly Ile Val Phe Ala Ala Ile Asn Ala
                165                 170                 175 tcg gtg cac gcc atc atg tac gcc tat tac gcc ttc acg gcc ctc ggc    576
Ser Val His Ala Ile Met Tyr Ala Tyr Tyr Ala Phe Thr Ala Leu Gly
                180                 185                 190 tac cga cca acc tcg tac gcc atc tac att acg ctc att cag atc atg    624
Tyr Arg Pro Thr Ser Tyr Ala Ile Tyr Ile Thr Leu Ile Gln Ile Met
            195                 200                 205 cag atg gtc gtc ggc acc gcc gtc acc ttt tac att ggc tac gac atg    672
Gln Met Val Val Gly Thr Ala Val Thr Phe Tyr Ile Gly Tyr Asp Met
210                 215                 220 gcc ttt gtc acg ccg cag ccc ttc cgc ctt gac atg aaa ctc aac tgg    720
Ala Phe Val Thr Pro Gln Pro Phe Arg Leu Asp Met Lys Leu Asn Trp
225                 230                 235                 240 gac ccg ctc agc aag ggc gag aac acc gag ccc acc tgc aag ggc gcc    768
Asp Pro Leu Ser Lys Gly Glu Asn Thr Glu Pro Thr Cys Lys Gly Ala
                245                 250                 255 aac tcc tcc aac gcc atc ttc ggc gtc atc atg tac gcc tcg tac ctc    816
Asn Ser Ser Asn Ala Ile Phe Gly Val Ile Met Tyr Ala Ser Tyr Leu
                260                 265                 270 tac ctc ttc tgc ctc ttc ttc tac atg gcc tac ctg cgc ccg aag aag    864
Tyr Leu Phe Cys Leu Phe Phe Tyr Met Ala Tyr Leu Arg Pro Lys Lys
            275                 280                 285 tcg acg ccc gcg gcc aag aag aca aac taa tcgcacacta ccaaacaatc      914
Ser Thr Pro Ala Ala Lys Lys Thr Asn
290                 295 ttccactcga cctagaaaaa aaaaaaaaaa aaaaactcga g                      955

<210> SEQ ID NO 6
<211> LENGTH: 297
<212> TYPE: PRT
<213> ORGANISM: Thaustochytrium

<400> SEQUENCE: 6

Val Ile Ser Gly Leu Asp Leu Leu Pro Val Leu Ser Trp Glu Thr Met
1               5                   10                  15

Lys Phe Asp Thr Ala Glu Val Val Ser Val Trp Leu Arg Thr His Met
                20                  25                  30

Trp Val Pro Phe Leu Met Cys Phe Ile Tyr Leu Val Val Ile Phe Gly
            35                  40                  45

Ile Gln Tyr Tyr Met Glu Asp Arg Lys Glu Phe Asp Leu Arg Lys Pro
        50                  55                  60

Leu Ala Ala Trp Ser Ala Phe Leu Ala Ile Phe Ser Ile Gly Ala Ser
65              70                  75                  80

Ile Arg Thr Val Pro Val Leu Leu Lys Met Leu Tyr Glu Lys Gly Thr
                85                  90                  95

His His Val Leu Cys Gly Asp Thr Arg Asn Asp Trp Val Ile Asp Asn
            100                 105                 110

Pro Ala Gly Val Trp Thr Met Ala Phe Ile Phe Ser Lys Ile Pro Glu
```

```
                115                 120                 125
Leu Ile Asp Thr Leu Phe Ile Val Leu Arg Lys Arg Lys Leu Ile Thr
        130                 135                 140

Leu His Trp Tyr His His Val Thr Val Leu Leu Phe Cys Trp His Ala
145                 150                 155                 160

Trp Ala Thr Phe Ala Leu Thr Gly Ile Val Phe Ala Ala Ile Asn Ala
                165                 170                 175

Ser Val His Ala Ile Met Tyr Ala Tyr Tyr Ala Phe Thr Ala Leu Gly
            180                 185                 190

Tyr Arg Pro Thr Ser Tyr Ala Ile Tyr Ile Thr Leu Ile Gln Ile Met
        195                 200                 205

Gln Met Val Val Gly Thr Ala Val Thr Phe Tyr Ile Gly Tyr Asp Met
    210                 215                 220

Ala Phe Val Thr Pro Gln Pro Phe Arg Leu Asp Met Lys Leu Asn Trp
225                 230                 235                 240

Asp Pro Leu Ser Lys Gly Glu Asn Thr Glu Pro Thr Cys Lys Gly Ala
                245                 250                 255

Asn Ser Ser Asn Ala Ile Phe Gly Val Ile Met Tyr Ala Ser Tyr Leu
            260                 265                 270

Tyr Leu Phe Cys Leu Phe Phe Tyr Met Ala Tyr Leu Arg Pro Lys Lys
        275                 280                 285

Ser Thr Pro Ala Ala Lys Lys Thr Asn
        290                 295

<210> SEQ ID NO 7
<211> LENGTH: 708
<212> TYPE: DNA
<213> ORGANISM: Crypthecodinium
<220> FEATURE:
<221> NAME/KEY: CDS
<222> LOCATION: (1)..(645)

<400> SEQUENCE: 7 cgg cac gag gta cac atg acc gag aag agg gga ctg cag ttc acg atc      48
Arg His Glu Val His Met Thr Glu Lys Arg Gly Leu Gln Phe Thr Ile
  1               5                  10                  15 tgc ggc tct act ggt gag ttg gtg cag aat ctc cag gat ggt ccc act      96
Cys Gly Ser Thr Gly Glu Leu Val Gln Asn Leu Gln Asp Gly Pro Thr
                 20                  25                  30 gcc ttg gcg ttg tgc ctc ttt tgc ttc agc aaa att ccc gag ttg atg     144
Ala Leu Ala Leu Cys Leu Phe Cys Phe Ser Lys Ile Pro Glu Leu Met
             35                  40                  45 gac acg gtc ttt ctc atc ttg aag ggc aag aag gtt cgc ttt ttg cag     192
Asp Thr Val Phe Leu Ile Leu Lys Gly Lys Lys Val Arg Phe Leu Gln
         50                  55                  60 tgg tac cac cac gct acc gtg atg ctc ttc tgc tgg ttg gca ctg gct     240
Trp Tyr His His Ala Thr Val Met Leu Phe Cys Trp Leu Ala Leu Ala
 65                  70                  75                  80 acg gag tac acc ccg ggc ctc tgg ttc gcg gcc act aac tac ttc gtg     288
Thr Glu Tyr Thr Pro Gly Leu Trp Phe Ala Ala Thr Asn Tyr Phe Val
                 85                  90                  95 cac tcc atc atg tac atg tac ttc ttg atg acc ttc aag acg gcc         336
His Ser Ile Met Tyr Met Tyr Phe Phe Leu Met Thr Phe Lys Thr Ala
                100                 105                 110 gca aag gtc gtg aag ccc att gcc cct ctc atc acc atc atc cag atc     384
Ala Lys Val Val Lys Pro Ile Ala Pro Leu Ile Thr Ile Ile Gln Ile
            115                 120                 125 gcc cag atg gtc tgg ggt ctc atc gtc aac ggc atc gcg atc acc act     432
```

```
Ala Gln Met Val Trp Gly Leu Ile Val Asn Gly Ile Ala Ile Thr Thr
        130                 135                 140 ttc ttc acc acg ggc gcc tgc cag atc cag tcc gtg acg gtc tac tcg      480
Phe Phe Thr Thr Gly Ala Cys Gln Ile Gln Ser Val Thr Val Tyr Ser
145                 150                 155                 160 gcc att gtg atg tac gct tcg tac ttc tac ctc ttc tcc cag ctc ttc      528
Ala Ile Val Met Tyr Ala Ser Tyr Phe Tyr Leu Phe Ser Gln Leu Phe
                    165                 170                 175 ctg gag gca tac gga tcc gct ggc aag aac aag aag aag ctc gcc cgc      576
Leu Glu Ala Tyr Gly Ser Ala Gly Lys Asn Lys Lys Lys Leu Ala Arg
                180                 185                 190 gag ctc tcc cga aag atc tcc gag gct ctc ctg aat agt ggc gac gag      624
Glu Leu Ser Arg Lys Ile Ser Glu Ala Leu Leu Asn Ser Gly Asp Glu
            195                 200                 205 gta gcc aag cac ctc aag tga actgagcgac ctcatcttgg tctggtccgc         675
Val Ala Lys His Leu Lys
            210 caaattgccg cgtgcatgtg catgagatgc tgt                                 708

<210> SEQ ID NO 8
<211> LENGTH: 214
<212> TYPE: PRT
<213> ORGANISM: Crypthecodinium

<400> SEQUENCE: 8

Arg His Glu Val His Met Thr Glu Lys Arg Gly Leu Gln Phe Thr Ile
  1               5                  10                  15

Cys Gly Ser Thr Gly Glu Leu Val Gln Asn Leu Gln Asp Gly Pro Thr
                 20                  25                  30

Ala Leu Ala Leu Cys Leu Phe Cys Phe Ser Lys Ile Pro Glu Leu Met
             35                  40                  45

Asp Thr Val Phe Leu Ile Leu Lys Gly Lys Lys Val Arg Phe Leu Gln
         50                  55                  60

Trp Tyr His His Ala Thr Val Met Leu Phe Cys Trp Leu Ala Leu Ala
     65                  70                  75                  80

Thr Glu Tyr Thr Pro Gly Leu Trp Phe Ala Ala Thr Asn Tyr Phe Val
                 85                  90                  95

His Ser Ile Met Tyr Met Tyr Phe Phe Leu Met Thr Phe Lys Thr Ala
            100                 105                 110

Ala Lys Val Val Lys Pro Ile Ala Pro Leu Ile Thr Ile Gln Ile
        115                 120                 125

Ala Gln Met Val Trp Gly Leu Ile Val Asn Gly Ile Ala Ile Thr Thr
    130                 135                 140

Phe Phe Thr Thr Gly Ala Cys Gln Ile Gln Ser Val Thr Val Tyr Ser
145                 150                 155                 160

Ala Ile Val Met Tyr Ala Ser Tyr Phe Tyr Leu Phe Ser Gln Leu Phe
                165                 170                 175

Leu Glu Ala Tyr Gly Ser Ala Gly Lys Asn Lys Lys Lys Leu Ala Arg
                180                 185                 190

Glu Leu Ser Arg Lys Ile Ser Glu Ala Leu Leu Asn Ser Gly Asp Glu
            195                 200                 205

Val Ala Lys His Leu Lys
            210

<210> SEQ ID NO 9
<211> LENGTH: 1054
<212> TYPE: DNA
```

<213> ORGANISM: Thraustochytrium
<220> FEATURE:
<221> NAME/KEY: CDS
<222> LOCATION: (43)..(858)

<400> SEQUENCE: 9

```
gaattcggca cgagagcgcg cggagcggag acctcggccg cg atg atg gag ccg        54
                                                Met Met Glu Pro
                                                1 ctc gac agg tac agg gcg ctg gcg gag ctc gcc gcg agg tac gcc agc      102
Leu Asp Arg Tyr Arg Ala Leu Ala Glu Leu Ala Ala Arg Tyr Ala Ser
 5                  10                  15                  20 tcg gcg gcc ttc aag tgg caa gtc acg tac gac gcc aag gac agc ttc      150
Ser Ala Ala Phe Lys Trp Gln Val Thr Tyr Asp Ala Lys Asp Ser Phe
                 25                  30                  35 gtc ggg ccc ctg gga atc cgg gag ccg ctc ggg ctc ctg gtg ggc tcc      198
Val Gly Pro Leu Gly Ile Arg Glu Pro Leu Gly Leu Leu Val Gly Ser
             40                  45                  50 gtg gtc ctc tac ctg agc ctg ctg gcc gtg gtc tac gcg ctg cgg aac      246
Val Val Leu Tyr Leu Ser Leu Leu Ala Val Val Tyr Ala Leu Arg Asn
         55                  60                  65 tac ctt ggc ggc ctc atg gcg ctc cgc agc gtg cat aac ctc ggg ctc      294
Tyr Leu Gly Gly Leu Met Ala Leu Arg Ser Val His Asn Leu Gly Leu
 70                  75                  80 tgc ctc ttc tcg ggc gcc gtg tgg atc tac acg agc tac ctc atg atc      342
Cys Leu Phe Ser Gly Ala Val Trp Ile Tyr Thr Ser Tyr Leu Met Ile
 85                  90                  95                 100 cag gat ggg cac ttt cgc agc ctc gag gcg gca acg tgc gag ccg ctc      390
Gln Asp Gly His Phe Arg Ser Leu Glu Ala Ala Thr Cys Glu Pro Leu
                105                 110                 115 aag cat ccg cac ttc cag ctc atc agc ttg ctc ttt gcg ctg tcc aag      438
Lys His Pro His Phe Gln Leu Ile Ser Leu Leu Phe Ala Leu Ser Lys
            120                 125                 130 atc tgg gag tgg ttc gac acg gtg ctc ctc atc gtc aag ggc aac aag      486
Ile Trp Glu Trp Phe Asp Thr Val Leu Leu Ile Val Lys Gly Asn Lys
        135                 140                 145 ctc cgc ttc ctg cac gtc ttg cac cac gcc acg acc ttt tgg ctc tac      534
Leu Arg Phe Leu His Val Leu His His Ala Thr Thr Phe Trp Leu Tyr
    150                 155                 160 gcc atc gac cac atc ttt ctc tcg tcc atc aag tac ggc gtc gcg gtc      582
Ala Ile Asp His Ile Phe Leu Ser Ser Ile Lys Tyr Gly Val Ala Val
165                 170                 175                 180 aat gct ttc atc cac acc gtc atg tac gcg cac tac ttc cgc cca ttc      630
Asn Ala Phe Ile His Thr Val Met Tyr Ala His Tyr Phe Arg Pro Phe
                185                 190                 195 ccg aag ggc ttg cgc ccg ctt att acg cag ttg cag atc gtc cag ttc      678
Pro Lys Gly Leu Arg Pro Leu Ile Thr Gln Leu Gln Ile Val Gln Phe
            200                 205                 210 att ttc agc atc ggc atc cat acc gcc att tac tgg cac tac gac tgc      726
Ile Phe Ser Ile Gly Ile His Thr Ala Ile Tyr Trp His Tyr Asp Cys
        215                 220                 225 gag ccg ctc gtg cat acc cac ttt tgg gaa tac gtc acg ccc tac ctt      774
Glu Pro Leu Val His Thr His Phe Trp Glu Tyr Val Thr Pro Tyr Leu
    230                 235                 240 ttc gtc gtg ccc ttc ctc atc ctc ttt ttc aat ttt tac ctg cag cag      822
Phe Val Val Pro Phe Leu Ile Leu Phe Phe Asn Phe Tyr Leu Gln Gln
245                 250                 255                 260 tac gtc ctc gcg ccc gca aaa acc aag aag gca tag ccacgtaaca           868
Tyr Val Leu Ala Pro Ala Lys Thr Lys Lys Ala
                265                 270
```

```
gtagaccagc agcgccgagg acgcgtgccg cgttatcgcg aagcacgaaa taaagaagat      928
catttgattc aacgaggcta cttgcggcca cgagaaaaaa aaaaaaaaaa aaaaaaaaaa      988
aaaaaaaaaa aaaaaaaaaa aaaaaaaaaa aaaaaaaaaa aaaaaaaaaa aaaaaaaaaa     1048
ctcgag                                                                1054
```

<210> SEQ ID NO 10
<211> LENGTH: 271
<212> TYPE: PRT
<213> ORGANISM: Thraustochytrium

<400> SEQUENCE: 10

```
Met Met Glu Pro Leu Asp Arg Tyr Arg Ala Leu Ala Glu Leu Ala Ala
 1               5                  10                  15

Arg Tyr Ala Ser Ser Ala Ala Phe Lys Trp Gln Val Thr Tyr Asp Ala
            20                  25                  30

Lys Asp Ser Phe Val Gly Pro Leu Gly Ile Arg Glu Pro Leu Gly Leu
        35                  40                  45

Leu Val Gly Ser Val Val Leu Tyr Leu Ser Leu Leu Ala Val Val Tyr
    50                  55                  60

Ala Leu Arg Asn Tyr Leu Gly Gly Leu Met Ala Leu Arg Ser Val His
65                  70                  75                  80

Asn Leu Gly Leu Cys Leu Phe Ser Gly Ala Val Trp Ile Tyr Thr Ser
                85                  90                  95

Tyr Leu Met Ile Gln Asp Gly His Phe Arg Ser Leu Glu Ala Ala Thr
            100                 105                 110

Cys Glu Pro Leu Lys His Pro His Phe Gln Leu Ile Ser Leu Leu Phe
        115                 120                 125

Ala Leu Ser Lys Ile Trp Glu Trp Phe Asp Thr Val Leu Leu Ile Val
    130                 135                 140

Lys Gly Asn Lys Leu Arg Phe Leu His Val Leu His His Ala Thr Thr
145                 150                 155                 160

Phe Trp Leu Tyr Ala Ile Asp His Ile Phe Leu Ser Ser Ile Lys Tyr
                165                 170                 175

Gly Val Ala Val Asn Ala Phe Ile His Thr Val Met Tyr Ala His Tyr
            180                 185                 190

Phe Arg Pro Phe Pro Lys Gly Leu Arg Pro Leu Ile Thr Gln Leu Gln
        195                 200                 205

Ile Val Gln Phe Ile Phe Ser Ile Gly Ile His Thr Ala Ile Tyr Trp
    210                 215                 220

His Tyr Asp Cys Glu Pro Leu Val His Thr His Phe Trp Glu Tyr Val
225                 230                 235                 240

Thr Pro Tyr Leu Phe Val Val Pro Phe Leu Ile Leu Phe Phe Asn Phe
                245                 250                 255

Tyr Leu Gln Gln Tyr Val Leu Ala Pro Ala Lys Thr Lys Lys Ala
            260                 265                 270
```

<210> SEQ ID NO 11
<211> LENGTH: 421
<212> TYPE: DNA
<213> ORGANISM: Phytophthora infestans
<220> FEATURE:
<221> NAME/KEY: CDS
<222> LOCATION: (1)..(279)

<400> SEQUENCE: 11

```
cac acc atc atg tac act tac tac ttc gtc agc gcc cac acg cgc aac       48
```

```
                His Thr Ile Met Tyr Thr Tyr Tyr Phe Val Ser Ala His Thr Arg Asn
                  1               5                  10                  15 att tgg tgg aag aag tac ctc acg cgc att cag ctt atc cag ttc gtg          96
Ile Trp Trp Lys Lys Tyr Leu Thr Arg Ile Gln Leu Ile Gln Phe Val
                 20                  25                  30 acc atg aac gtg cag ggc tac ctg acc tac tct cga cag tgc cca ggc         144
Thr Met Asn Val Gln Gly Tyr Leu Thr Tyr Ser Arg Gln Cys Pro Gly
             35                  40                  45 atg cct cct aag gtg ccg ctc atg tac ctt gtg tac gtg cag tca ctc         192
Met Pro Pro Lys Val Pro Leu Met Tyr Leu Val Tyr Val Gln Ser Leu
         50                  55                  60 ttc tgg ctc ttc atg aat ttc tac att cgc gcg tac gtg ttc ggc ccc         240
Phe Trp Leu Phe Met Asn Phe Tyr Ile Arg Ala Tyr Val Phe Gly Pro
 65                  70                  75                  80 aag aaa ccg gcc gtg gag gaa tcg aag aag aag ttg taa cggcgcttgt          289
Lys Lys Pro Ala Val Glu Glu Ser Lys Lys Lys Leu
                 85                  90 taaaaagtct aacctcgctg taacagctta aacacacac acacacaacg ctttgtagag        349
gaggtaagta gtggcaactc gtgtagaaat gcagcatgcc catcaaatac atcccgtatg       409
attcatacta ct                                                           421

<210> SEQ ID NO 12
<211> LENGTH: 92
<212> TYPE: PRT
<213> ORGANISM: Phytophthora infestans

<400> SEQUENCE: 12

His Thr Ile Met Tyr Thr Tyr Tyr Phe Val Ser Ala His Thr Arg Asn
  1               5                  10                  15

Ile Trp Trp Lys Lys Tyr Leu Thr Arg Ile Gln Leu Ile Gln Phe Val
                 20                  25                  30

Th

```
<210> SEQ ID NO 15
<211> LENGTH: 18
<212> TYPE: DNA
<213> ORGANISM: Artificial Sequence
<220> FEATURE:
<223> OTHER INFORMATION: Sequencing primer

<400> SEQUENCE: 15
tgtaaaacga cggccagt                                                 18

<210> SEQ ID NO 16
<211> LENGTH: 32
<212> TYPE: DNA
<213> ORGANISM: Artificial Sequence
<220> FEATURE:
<223> OTHER INFORMATION: primer for PCR

<400> SEQUENCE: 16
ggatccacat aatggaggtc gtggagagat tc                                 32

<210> SEQ ID NO 17
<211> LENGTH: 30
<212> TYPE: DNA
<213> ORGANISM: Artificial Sequence
<220> FEATURE:
<223> OTHER INFORMATION: primer for PCR

<400> SEQUENCE: 17
ggatcctcac tcagttttag ctccttttgc                                    30

<210> SEQ ID NO 18
<211> LENGTH: 75
<212> TYPE: DNA
<213> ORGANISM: Artificial Sequence
<220> FEATURE:
<223> OTHER INFORMATION: primer for PCR

<400> SEQUENCE: 18
aaaggatcca cataatggag gtcgtggaga gattctacgg tgagttggat gggaaggtca   60
tttcgggcct cgacc                                                    75

<210> SEQ ID NO 19
<211> LENGTH: 35
<212> TYPE: DNA
<213> ORGANISM: Artificial Sequence
<220> FEATURE:
<223> OTHER INFORMATION: primer for PCR

<400> SEQUENCE: 19
aaggatccct gagttttagc tccttttgc tttcc                               35
```